US011759508B2

(12) United States Patent
Chene et al.

(10) Patent No.: US 11,759,508 B2
(45) Date of Patent: Sep. 19, 2023

(54) ANTIGENIC PEPTIDES FOR TREATMENT OF B-CELL MALIGNANCY

(71) Applicant: ENTEROME S.A., Paris (FR)

(72) Inventors: Laurent Chene, Neuville Aux Bois (FR); Francesco Strozzi, Paris (FR); Joao Gamelas Magalhaes, Corbeil-Essonnes (FR); Guillaume Kulakowski, Le Kremlin Bicetre (FR)

(73) Assignee: ENTEROME S.A., Paris (FR)

( * ) Notice: Subject to any disclaimer, the term of this patent is extended or adjusted under 35 U.S.C. 154(b) by 0 days.

(21) Appl. No.: 17/734,694

(22) Filed: May 2, 2022

(65) Prior Publication Data

US 2022/0323561 A1 Oct. 13, 2022

Related U.S. Application Data

(63) Continuation of application No. PCT/EP2020/082101, filed on Nov. 13, 2020.

(30) Foreign Application Priority Data

Nov. 15, 2019 (EP) ..................................... 19306475
Oct. 16, 2020 (WO) ................. PCT/EP2020/079257

(51) Int. Cl.
*A61K 39/00* (2006.01)
*A61P 35/00* (2006.01)

(52) U.S. Cl.
CPC ................. *A61K 39/001112* (2018.08); *A61K 39/001113* (2018.08); *A61K 39/001117* (2018.08); *A61K 39/001124* (2018.08); *A61K 39/001129* (2018.08); *A61P 35/00* (2018.01); *A61K 2039/55516* (2013.01); *A61K 2039/55566* (2013.01)

(58) Field of Classification Search
CPC .......................... A61K 39/001112; A61P 35/00
See application file for complete search history.

(56) References Cited

FOREIGN PATENT DOCUMENTS

| CN | 106008695 A | 10/2016 |
|---|---|---|
| WO | WO-2005007673 A2 | 1/2005 |
| WO | WO-2013040142 A2 | 3/2013 |
| WO | WO-2017184590 A1 | 10/2017 |
| WO | WO-2019051001 A1 | 3/2019 |
| WO | WO-2019072871 A2 | 4/2019 |
| WO | WO-2019197567 A2 | 10/2019 |
| WO | WO-2020072700 A1 | 4/2020 |

OTHER PUBLICATIONS

International Search Report from corresponding PCT Application No. PCT/EP2020/082101 dated Aug. 30, 2021.
Written Opinion from corresponding PCT Application No. PCT/EP2020/082101 dated Aug. 30, 2021.
Database UniProt, "Database accession No. UniParc—UPI000197B4B6", XP002803181, Sep. 18, 2013.
Database UniProt, "Database accession No. UniParc—UPI0009BFB842", XP055810403, Dec. 5, 2018.

*Primary Examiner* — Elly-Gerald Stoica
(74) *Attorney, Agent, or Firm* — Harness Dickey & Pierce P.L.C.

(57) ABSTRACT

The present invention relates to antigen-based immunotherapy, in particular cancer immunotherapy. In particular, the present invention provides antigenic peptides, which are distinct from, but have amino acid similarity to, especially share the same core sequence with epitopes of human tumor antigens. The present invention further provides immunogenic compounds, nanoparticles, cells and pharmaceutical compositions comprising such antigenic peptides and nucleic acids encoding such antigenic peptides.

20 Claims, 15 Drawing Sheets

Specification includes a Sequence Listing.

SEQUENCE LISTING

<160> NUMBER OF SEQ ID NOS: 509

<210> SEQ ID NO 1
<211> LENGTH: 9
<212> TYPE: PRT
<213> ORGANISM: Artificial Sequence
<220> FEATURE:
<223> OTHER INFORMATION: peptide

<400> SEQUENCE: 1

Phe Leu Leu Phe Leu Thr Pro Ile Leu
1               5

```
<210> SEQ ID NO 2
<211> LENGTH: 9
<212> TYPE: PRT
<213> ORGANISM: Artificial
<220> FEATURE:
<223> OTHER INFORMATION: peptide

<400> SEQUENCE: 2

Phe Leu Leu Phe Leu Thr Pro Leu Leu
1               5

<210> SEQ ID NO 3
<211> LENGTH: 9
<212> TYPE: PRT
<213> ORGANISM: Artificial
<220> FEATURE:
<223> OTHER INFORMATION: peptide

<400> SEQUENCE: 3

Phe Met Leu Phe Leu Thr Pro Arg Ile
1               5

<210> SEQ ID NO 4
<211> LENGTH: 9
<212> TYPE: PRT
<213> ORGANISM: Artificial
<220> FEATURE:
<223> OTHER INFORMATION: peptide

<400> SEQUENCE: 4

Gly Leu Leu Phe Leu Thr Pro Leu Ala
1               5

<210> SEQ ID NO 5
<211> LENGTH: 9
<212> TYPE: PRT
<213> ORGANISM: Artificial
<220> FEATURE:
<223> OTHER INFORMATION: peptide

<400> SEQUENCE: 5

Gly Leu Leu Phe Leu Thr Pro Leu Leu
1               5

<210> SEQ ID NO 6
<211> LENGTH: 9
<212> TYPE: PRT
<213> ORGANISM: Artificial
<220> FEATURE:
<223> OTHER INFORMATION: peptide

<400> SEQUENCE: 6

Gly Leu Leu Phe Leu Thr Pro Leu Met
1               5

<210> SEQ ID NO 7
<211> LENGTH: 9
<212> TYPE: PRT
<213> ORGANISM: Artificial
<220> FEATURE:
<223> OTHER INFORMATION: peptide

<400> SEQUENCE: 7

Ile Leu Leu Phe Leu Thr Pro Leu Leu
1               5
```

```
<210> SEQ ID NO 8
<211> LENGTH: 9
<212> TYPE: PRT
<213> ORGANISM: Artificial
<220> FEATURE:
<223> OTHER INFORMATION: peptide

<400> SEQUENCE: 8

Ser Leu Leu Phe Leu Thr Pro Leu Leu
1               5

<210> SEQ ID NO 9
<211> LENGTH: 9
<212> TYPE: PRT
<213> ORGANISM: Artificial
<220> FEATURE:
<223> OTHER INFORMATION: peptide

<400> SEQUENCE: 9

Thr Leu Leu Phe Leu Thr Pro Leu Ile
1               5

<210> SEQ ID NO 10
<211> LENGTH: 9
<212> TYPE: PRT
<213> ORGANISM: Artificial
<220> FEATURE:
<223> OTHER INFORMATION: peptide

<400> SEQUENCE: 10

Thr Leu Leu Phe Leu Thr Pro Met Leu
1               5

<210> SEQ ID NO 11
<211> LENGTH: 9
<212> TYPE: PRT
<213> ORGANISM: Artificial
<220> FEATURE:
<223> OTHER INFORMATION: peptide

<400> SEQUENCE: 11

Val Leu Leu Phe Leu Thr Pro Met Leu
1               5

<210> SEQ ID NO 12
<211> LENGTH: 9
<212> TYPE: PRT
<213> ORGANISM: Artificial
<220> FEATURE:
<223> OTHER INFORMATION: peptide

<400> SEQUENCE: 12

Tyr Leu Leu Phe Leu Thr Pro Val Leu
1               5

<210> SEQ ID NO 13
<211> LENGTH: 9
<212> TYPE: PRT
<213> ORGANISM: Artificial
<220> FEATURE:
<223> OTHER INFORMATION: peptide

<400> SEQUENCE: 13

Ala Leu Ser Leu Gly Leu Pro Gly Leu
1               5

<210> SEQ ID NO 14
```

```
<211> LENGTH: 9
<212> TYPE: PRT
<213> ORGANISM: Artificial
<220> FEATURE:
<223> OTHER INFORMATION: peptide

<400> SEQUENCE: 14

Ala Leu Ser Leu Gly Leu Pro Leu Leu
1               5

<210> SEQ ID NO 15
<211> LENGTH: 9
<212> TYPE: PRT
<213> ORGANISM: Artificial
<220> FEATURE:
<223> OTHER INFORMATION: peptide

<400> SEQUENCE: 15

Ala Leu Ser Leu Gly Leu Pro Met Leu
1               5

<210> SEQ ID NO 16
<211> LENGTH: 9
<212> TYPE: PRT
<213> ORGANISM: Artificial
<220> FEATURE:
<223> OTHER INFORMATION: peptide

<400> SEQUENCE: 16

Ala Leu Ser Leu Gly Leu Pro Gln Leu
1               5

<210> SEQ ID NO 17
<211> LENGTH: 9
<212> TYPE: PRT
<213> ORGANISM: Artificial
<220> FEATURE:
<223> OTHER INFORMATION: peptide

<400> SEQUENCE: 17

Ala Leu Ser Leu Gly Leu Pro Arg Leu
1               5

<210> SEQ ID NO 18
<211> LENGTH: 9
<212> TYPE: PRT
<213> ORGANISM: Artificial
<220> FEATURE:
<223> OTHER INFORMATION: peptide

<400> SEQUENCE: 18

Ala Met Ser Leu Gly Leu Pro Cys Leu
1               5

<210> SEQ ID NO 19
<211> LENGTH: 9
<212> TYPE: PRT
<213> ORGANISM: Artificial
<220> FEATURE:
<223> OTHER INFORMATION: peptide

<400> SEQUENCE: 19

Ala Met Ser Leu Gly Leu Pro Met Leu
1               5

<210> SEQ ID NO 20
<211> LENGTH: 9
```

```
<212> TYPE: PRT
<213> ORGANISM: Artificial
<220> FEATURE:
<223> OTHER INFORMATION: peptide

<400> SEQUENCE: 20

Phe Leu Ser Leu Gly Leu Pro Ile Leu
1               5

<210> SEQ ID NO 21
<211> LENGTH: 9
<212> TYPE: PRT
<213> ORGANISM: Artificial
<220> FEATURE:
<223> OTHER INFORMATION: peptide

<400> SEQUENCE: 21

Phe Leu Ser Leu Gly Leu Pro Lys Leu
1               5

<210> SEQ ID NO 22
<211> LENGTH: 9
<212> TYPE: PRT
<213> ORGANISM: Artificial
<220> FEATURE:
<223> OTHER INFORMATION: peptide

<400> SEQUENCE: 22

Ile Leu Ser Leu Gly Leu Pro Ile Leu
1               5

<210> SEQ ID NO 23
<211> LENGTH: 9
<212> TYPE: PRT
<213> ORGANISM: Artificial
<220> FEATURE:
<223> OTHER INFORMATION: peptide

<400> SEQUENCE: 23

Lys Leu Ser Leu Gly Leu Pro Val Leu
1               5

<210> SEQ ID NO 24
<211> LENGTH: 9
<212> TYPE: PRT
<213> ORGANISM: Artificial
<220> FEATURE:
<223> OTHER INFORMATION: peptide

<400> SEQUENCE: 24

Leu Leu Ser Leu Gly Leu Pro Phe Leu
1               5

<210> SEQ ID NO 25
<211> LENGTH: 9
<212> TYPE: PRT
<213> ORGANISM: Artificial
<220> FEATURE:
<223> OTHER INFORMATION: peptide

<400> SEQUENCE: 25

Leu Leu Ser Leu Gly Leu Pro Gly Leu
1               5

<210> SEQ ID NO 26
<211> LENGTH: 9
<212> TYPE: PRT
```

```
<213> ORGANISM: Artificial
<220> FEATURE:
<223> OTHER INFORMATION: peptide

<400> SEQUENCE: 26

Met Leu Ser Leu Gly Leu Pro Ile Leu
1               5

<210> SEQ ID NO 27
<211> LENGTH: 9
<212> TYPE: PRT
<213> ORGANISM: Artificial
<220> FEATURE:
<223> OTHER INFORMATION: peptide

<400> SEQUENCE: 27

Arg Leu Ser Leu Gly Leu Pro Gly Leu
1               5

<210> SEQ ID NO 28
<211> LENGTH: 9
<212> TYPE: PRT
<213> ORGANISM: Artificial
<220> FEATURE:
<223> OTHER INFORMATION: peptide

<400> SEQUENCE: 28

Ser Leu Ser Leu Gly Leu Pro Ile Leu
1               5

<210> SEQ ID NO 29
<211> LENGTH: 9
<212> TYPE: PRT
<213> ORGANISM: Artificial
<220> FEATURE:
<223> OTHER INFORMATION: peptide

<400> SEQUENCE: 29

Ser Leu Ser Leu Gly Leu Pro Lys Leu
1               5

<210> SEQ ID NO 30
<211> LENGTH: 9
<212> TYPE: PRT
<213> ORGANISM: Artificial
<220> FEATURE:
<223> OTHER INFORMATION: peptide

<400> SEQUENCE: 30

Val Leu Ser Leu Gly Leu Pro Leu Leu
1               5

<210> SEQ ID NO 31
<211> LENGTH: 9
<212> TYPE: PRT
<213> ORGANISM: Artificial
<220> FEATURE:
<223> OTHER INFORMATION: peptide

<400> SEQUENCE: 31

Val Leu Ser Leu Gly Leu Pro Thr Ala
1               5

<210> SEQ ID NO 32
<211> LENGTH: 9
<212> TYPE: PRT
<213> ORGANISM: Artificial
```

```
<220> FEATURE:
<223> OTHER INFORMATION: peptide

<400> SEQUENCE: 32

Val Leu Ser Leu Gly Leu Pro Thr Val
1               5

<210> SEQ ID NO 33
<211> LENGTH: 9
<212> TYPE: PRT
<213> ORGANISM: Artificial
<220> FEATURE:
<223> OTHER INFORMATION: peptide

<400> SEQUENCE: 33

Tyr Leu Ser Leu Gly Leu Pro Ile Leu
1               5

<210> SEQ ID NO 34
<211> LENGTH: 9
<212> TYPE: PRT
<213> ORGANISM: Artificial
<220> FEATURE:
<223> OTHER INFORMATION: peptide

<400> SEQUENCE: 34

Leu Leu Val Gly Ile Leu His Leu Val
1               5

<210> SEQ ID NO 35
<211> LENGTH: 9
<212> TYPE: PRT
<213> ORGANISM: Artificial
<220> FEATURE:
<223> OTHER INFORMATION: peptide

<400> SEQUENCE: 35

Ser Leu Val Gly Ile Leu His Ile Ile
1               5

<210> SEQ ID NO 36
<211> LENGTH: 9
<212> TYPE: PRT
<213> ORGANISM: Artificial
<220> FEATURE:
<223> OTHER INFORMATION: peptide

<400> SEQUENCE: 36

Phe Leu Ala Tyr Leu Ile Phe Gly Leu
1               5

<210> SEQ ID NO 37
<211> LENGTH: 9
<212> TYPE: PRT
<213> ORGANISM: Artificial
<220> FEATURE:
<223> OTHER INFORMATION: peptide

<400> SEQUENCE: 37

Phe Leu Ala Tyr Leu Ile Phe Thr Leu
1               5

<210> SEQ ID NO 38
<211> LENGTH: 9
<212> TYPE: PRT
<213> ORGANISM: Artificial
<220> FEATURE:
```

```
<223> OTHER INFORMATION: peptide

<400> SEQUENCE: 38

Arg Leu Ala Tyr Leu Ile Phe Leu Leu
1               5

<210> SEQ ID NO 39
<211> LENGTH: 9
<212> TYPE: PRT
<213> ORGANISM: Artificial
<220> FEATURE:
<223> OTHER INFORMATION: peptide

<400> SEQUENCE: 39

Tyr Leu Ala Tyr Leu Ile Phe Glu Leu
1               5

<210> SEQ ID NO 40
<211> LENGTH: 9
<212> TYPE: PRT
<213> ORGANISM: Artificial
<220> FEATURE:
<223> OTHER INFORMATION: peptide

<400> SEQUENCE: 40

Leu Gln Met Gly Gly Phe Tyr Leu Leu
1               5

<210> SEQ ID NO 41
<211> LENGTH: 9
<212> TYPE: PRT
<213> ORGANISM: Artificial
<220> FEATURE:
<223> OTHER INFORMATION: peptide

<400> SEQUENCE: 41

Ala Ile Leu Gly Gly Leu Leu Leu Ile
1               5

<210> SEQ ID NO 42
<211> LENGTH: 9
<212> TYPE: PRT
<213> ORGANISM: Artificial
<220> FEATURE:
<223> OTHER INFORMATION: peptide

<400> SEQUENCE: 42

Ala Leu Leu Gly Gly Leu Leu Leu Ile
1               5

<210> SEQ ID NO 43
<211> LENGTH: 9
<212> TYPE: PRT
<213> ORGANISM: Artificial
<220> FEATURE:
<223> OTHER INFORMATION: peptide

<400> SEQUENCE: 43

Ala Leu Leu Gly Gly Leu Leu Met Leu
1               5

<210> SEQ ID NO 44
<211> LENGTH: 9
<212> TYPE: PRT
<213> ORGANISM: Artificial
<220> FEATURE:
<223> OTHER INFORMATION: peptide
```

```
<400> SEQUENCE: 44

Phe Ala Leu Gly Gly Leu Leu Thr Val
1               5

<210> SEQ ID NO 45
<211> LENGTH: 9
<212> TYPE: PRT
<213> ORGANISM: Artificial
<220> FEATURE:
<223> OTHER INFORMATION: peptide

<400> SEQUENCE: 45

Phe Leu Leu Gly Gly Leu Leu Leu Ile
1               5

<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Phe Leu Leu Gly Gly Leu Leu Met Val
1               5

<210> SEQ ID NO 47
<211> LENGTH: 9
<212> TYPE: PRT
<213> ORGANISM: Artificial
<220> FEATURE:
<223> OTHER INFORMATION: peptide

<400> SEQUENCE: 47

Gly Met Leu Gly Gly Leu Leu Leu Ile
1               5

<210> SEQ ID NO 48
<211> LENGTH: 9
<212> TYPE: PRT
<213> ORGANISM: Artificial
<220> FEATURE:
<223> OTHER INFORMATION: peptide

<400> SEQUENCE: 48

Gly Met Leu Gly Gly Leu Leu Met Leu
1               5

<210> SEQ ID NO 49
<211> LENGTH: 9
<212> TYPE: PRT
<213> ORGANISM: Artificial
<220> FEATURE:
<223> OTHER INFORMATION: peptide

<400> SEQUENCE: 49

His Ile Leu Gly Gly Leu Leu Met Val
1               5

<210> SEQ ID NO 50
<211> LENGTH: 9
<212> TYPE: PRT
<213> ORGANISM: Artificial
<220> FEATURE:
<223> OTHER INFORMATION: peptide
```

```
<400> SEQUENCE: 50

Ile Ile Leu Gly Gly Leu Leu Val Val
1               5

<210> SEQ ID NO 51
<211> LENGTH: 9
<212> TYPE: PRT
<213> ORGANISM: Artificial
<220> FEATURE:
<223> OTHER INFORMATION: peptide

<400> SEQUENCE: 51

Ile Leu Leu Gly Gly Leu Leu Leu Ile
1               5

<210> SEQ ID NO 52
<211> LENGTH: 9
<212> TYPE: PRT
<213> ORGANISM: Artificial
<220> FEATURE:
<223> OTHER INFORMATION: peptide

<400> SEQUENCE: 52

Leu Leu Leu Gly Gly Leu Leu Leu Ile
1               5

<210> SEQ ID NO 53
<211> LENGTH: 9
<212> TYPE: PRT
<213> ORGANISM: Artificial
<220> FEATURE:
<223> OTHER INFORMATION: peptide

<400> SEQUENCE: 53

Leu Leu Leu Gly Gly Leu Leu Met Ile
1               5

<210> SEQ ID NO 54
<211> LENGTH: 9
<212> TYPE: PRT
<213> ORGANISM: Artificial
<220> FEATURE:
<223> OTHER INFORMATION: peptide

<400> SEQUENCE: 54

Asn Leu Leu Gly Gly Leu Leu Leu Ile
1               5

<210> SEQ ID NO 55
<211> LENGTH: 9
<212> TYPE: PRT
<213> ORGANISM: Artificial
<220> FEATURE:
<223> OTHER INFORMATION: peptide

<400> SEQUENCE: 55

Ser Ile Leu Gly Gly Leu Leu Leu Ile
1               5

<210> SEQ ID NO 56
<211> LENGTH: 9
<212> TYPE: PRT
<213> ORGANISM: Artificial
<220> FEATURE:
<223> OTHER INFORMATION: peptide

<400> SEQUENCE: 56
```

Ser Leu Leu Gly Gly Leu Leu Leu Ile
1               5

<210> SEQ ID NO 57
<211> LENGTH: 9
<212> TYPE: PRT
<213> ORGANISM: Artificial
<220> FEATURE:
<223> OTHER INFORMATION: peptide

<400> SEQUENCE: 57

Ser Leu Leu Gly Gly Leu Leu Met Leu
1               5

<210> SEQ ID NO 58
<211> LENGTH: 9
<212> TYPE: PRT
<213> ORGANISM: Artificial
<220> FEATURE:
<223> OTHER INFORMATION: peptide

<400> SEQUENCE: 58

Ser Met Leu Gly Gly Leu Leu Leu Ile
1               5

<210> SEQ ID NO 59
<211> LENGTH: 9
<212> TYPE: PRT
<213> ORGANISM: Artificial
<220> FEATURE:
<223> OTHER INFORMATION: peptide

<400> SEQUENCE: 59

Thr Leu Leu Gly Gly Leu Leu Met Ile
1               5

<210> SEQ ID NO 60
<211> LENGTH: 9
<212> TYPE: PRT
<213> ORGANISM: Artificial
<220> FEATURE:
<223> OTHER INFORMATION: peptide

<400> SEQUENCE: 60

Tyr Ala Leu Gly Gly Leu Leu Glu Val
1               5

<210> SEQ ID NO 61
<211> LENGTH: 9
<212> TYPE: PRT
<213> ORGANISM: Artificial
<220> FEATURE:
<223> OTHER INFORMATION: peptide

<400> SEQUENCE: 61

Tyr Ile Leu Gly Gly Leu Leu Met Val
1               5

<210> SEQ ID NO 62
<211> LENGTH: 9
<212> TYPE: PRT
<213> ORGANISM: Artificial
<220> FEATURE:
<223> OTHER INFORMATION: peptide

<400> SEQUENCE: 62

Tyr Met Leu Gly Gly Leu Leu Leu Ile
1               5

<210> SEQ ID NO 63
<211> LENGTH: 9
<212> TYPE: PRT
<213> ORGANISM: Artificial
<220> FEATURE:
<223> OTHER INFORMATION: peptide

<400> SEQUENCE: 63

Tyr Val Leu Gly Gly Leu Leu Met Ile
1               5

<210> SEQ ID NO 64
<211> LENGTH: 9
<212> TYPE: PRT
<213> ORGANISM: Artificial
<220> FEATURE:
<223> OTHER INFORMATION: peptide

<400> SEQUENCE: 64

Tyr Val Leu Gly Gly Leu Leu Met Val
1               5

<210> SEQ ID NO 65
<211> LENGTH: 9
<212> TYPE: PRT
<213> ORGANISM: Artificial
<220> FEATURE:
<223> OTHER INFORMATION: peptide

<400> SEQUENCE: 65

Ala Met Asn Ser Leu Ser Leu Tyr Ile
1               5

<210> SEQ ID NO 66
<211> LENGTH: 9
<212> TYPE: PRT
<213> ORGANISM: Artificial
<220> FEATURE:
<223> OTHER INFORMATION: peptide

<400> SEQUENCE: 66

Ile Leu Asn Ser Leu Ser Leu Lys Ile
1               5

<210> SEQ ID NO 67
<211> LENGTH: 9
<212> TYPE: PRT
<213> ORGANISM: Artificial
<220> FEATURE:
<223> OTHER INFORMATION: peptide

<400> SEQUENCE: 67

Ile Leu Asn Ser Leu Ser Leu Lys Leu
1               5

<210> SEQ ID NO 68
<211> LENGTH: 9
<212> TYPE: PRT
<213> ORGANISM: Artificial
<220> FEATURE:
<223> OTHER INFORMATION: peptide

<400> SEQUENCE: 68

Ile Leu Asn Ser Leu Ser Leu Leu Leu

```
1               5
```

<210> SEQ ID NO 69
<211> LENGTH: 9
<212> TYPE: PRT
<213> ORGANISM: Artificial
<220> FEATURE:
<223> OTHER INFORMATION: Artificial

<400> SEQUENCE: 69

```
Leu Leu Asn Ser Leu Ser Leu Phe Leu
1               5
```

<210> SEQ ID NO 70
<211> LENGTH: 9
<212> TYPE: PRT
<213> ORGANISM: Artificial
<220> FEATURE:
<223> OTHER INFORMATION: peptide

<400> SEQUENCE: 70

```
Tyr Met Asn Ser Leu Ser Leu Ala Leu
1               5
```

<210> SEQ ID NO 71
<211> LENGTH: 9
<212> TYPE: PRT
<213> ORGANISM: Artificial
<220> FEATURE:
<223> OTHER INFORMATION: peptide

<400> SEQUENCE: 71

```
Phe Leu Ile Pro Ala Gly Ile Phe Leu
1               5
```

<210> SEQ ID NO 72
<211> LENGTH: 9
<212> TYPE: PRT
<213> ORGANISM: Artificial
<220> FEATURE:
<223> OTHER INFORMATION: peptide

<400> SEQUENCE: 72

```
Ile Leu Ile Pro Ala Gly Ile Tyr Leu
1               5
```

<210> SEQ ID NO 73
<211> LENGTH: 9
<212> TYPE: PRT
<213> ORGANISM: Artificial
<220> FEATURE:
<223> OTHER INFORMATION: peptide

<400> SEQUENCE: 73

```
Leu Leu Ile Pro Ala Gly Ile Ala Val
1               5
```

<210> SEQ ID NO 74
<211> LENGTH: 9
<212> TYPE: PRT
<213> ORGANISM: Artificial
<220> FEATURE:
<223> OTHER INFORMATION: peptide

<400> SEQUENCE: 74

```
Leu Leu Ile Pro Ala Gly Ile Glu Leu
1               5
```

```
<210> SEQ ID NO 75
<211> LENGTH: 9
<212> TYPE: PRT
<213> ORGANISM: Artificial
<220> FEATURE:
<223> OTHER INFORMATION: peptide

<400> SEQUENCE: 75

Leu Leu Ile Pro Ala Gly Ile Gly Leu
1               5

<210> SEQ ID NO 76
<211> LENGTH: 9
<212> TYPE: PRT
<213> ORGANISM: Artificial
<220> FEATURE:
<223> OTHER INFORMATION: peptide

<400> SEQUENCE: 76

Leu Leu Ile Pro Ala Gly Ile Leu Ile
1               5

<210> SEQ ID NO 77
<211> LENGTH: 9
<212> TYPE: PRT
<213> ORGANISM: Artificial
<220> FEATURE:
<223> OTHER INFORMATION: peptide

<400> SEQUENCE: 77

Leu Leu Ile Pro Ala Gly Ile Leu Leu
1               5

<210> SEQ ID NO 78
<211> LENGTH: 9
<212> TYPE: PRT
<213> ORGANISM: Artificial
<220> FEATURE:
<223> OTHER INFORMATION: peptide

<400> SEQUENCE: 78

Met Leu Ile Pro Ala Gly Ile Pro Ala
1               5

<210> SEQ ID NO 79
<211> LENGTH: 9
<212> TYPE: PRT
<213> ORGANISM: Artificial
<220> FEATURE:
<223> OTHER INFORMATION: peptide

<400> SEQUENCE: 79

Met Met Ile Pro Ala Gly Ile Ala Val
1               5

<210> SEQ ID NO 80
<211> LENGTH: 9
<212> TYPE: PRT
<213> ORGANISM: Artificial
<220> FEATURE:
<223> OTHER INFORMATION: peptide

<400> SEQUENCE: 80

Val Met Ile Pro Ala Gly Ile Phe Leu
1               5
```

```
<210> SEQ ID NO 81
<211> LENGTH: 9
<212> TYPE: PRT
<213> ORGANISM: Artificial
<220> FEATURE:
<223> OTHER INFORMATION: peptide

<400> SEQUENCE: 81

Phe Leu Phe Leu Gly Ile Leu Gly Leu
1               5

<210> SEQ ID NO 82
<211> LENGTH: 9
<212> TYPE: PRT
<213> ORGANISM: Artificial
<220> FEATURE:
<223> OTHER INFORMATION: peptide

<400> SEQUENCE: 82

Phe Leu Phe Leu Gly Ile Leu Pro Leu
1               5

<210> SEQ ID NO 83
<211> LENGTH: 9
<212> TYPE: PRT
<213> ORGANISM: Artificial
<220> FEATURE:
<223> OTHER INFORMATION: peptide

<400> SEQUENCE: 83

Met Leu Phe Leu Gly Ile Leu Ser Val
1               5

<210> SEQ ID NO 84
<211> LENGTH: 9
<212> TYPE: PRT
<213> ORGANISM: Artificial
<220> FEATURE:
<223> OTHER INFORMATION: peptide

<400> SEQUENCE: 84

Tyr Leu Phe Leu Gly Ile Leu Gly Ile
1               5

<210> SEQ ID NO 85
<211> LENGTH: 9
<212> TYPE: PRT
<213> ORGANISM: Artificial
<220> FEATURE:
<223> OTHER INFORMATION: peptide

<400> SEQUENCE: 85

Tyr Leu Phe Leu Gly Ile Leu Gly Leu
1               5

<210> SEQ ID NO 86
<211> LENGTH: 9
<212> TYPE: PRT
<213> ORGANISM: Artificial
<220> FEATURE:
<223> OTHER INFORMATION: peptide

<400> SEQUENCE: 86

Tyr Leu Phe Leu Gly Ile Leu Ser Leu
1               5
```

```
<210> SEQ ID NO 87
<211> LENGTH: 9
<212> TYPE: PRT
<213> ORGANISM: Artificial
<220> FEATURE:
<223> OTHER INFORMATION: peptide

<400> SEQUENCE: 87

Tyr Leu Phe Leu Gly Ile Leu Tyr Leu
1               5

<210> SEQ ID NO 88
<211> LENGTH: 9
<212> TYPE: PRT
<213> ORGANISM: Artificial
<220> FEATURE:
<223> OTHER INFORMATION: peptide

<400> SEQUENCE: 88

Phe Leu Ser Asn Asp Thr Val Leu Leu
1               5

<210> SEQ ID NO 89
<211> LENGTH: 9
<212> TYPE: PRT
<213> ORGANISM: Artificial
<220> FEATURE:
<223> OTHER INFORMATION: peptide

<400> SEQUENCE: 89

Phe Leu Ser Asn Asp Thr Val Pro Leu
1               5

<210> SEQ ID NO 90
<211> LENGTH: 9
<212> TYPE: PRT
<213> ORGANISM: Artificial
<220> FEATURE:
<223> OTHER INFORMATION: peptide

<400> SEQUENCE: 90

Phe Leu Ser Asn Asp Thr Val Ser Ala
1               5

<210> SEQ ID NO 91
<211> LENGTH: 9
<212> TYPE: PRT
<213> ORGANISM: Artificial
<220> FEATURE:
<223> OTHER INFORMATION: peptide

<400> SEQUENCE: 91

Phe Met Ser Asn Asp Thr Val Lys Val
1               5

<210> SEQ ID NO 92
<211> LENGTH: 9
<212> TYPE: PRT
<213> ORGANISM: Artificial
<220> FEATURE:
<223> OTHER INFORMATION: peptide

<400> SEQUENCE: 92

Ile Leu Ser Asn Asp Thr Val Trp Leu
1               5

<210> SEQ ID NO 93
```

```
<211> LENGTH: 9
<212> TYPE: PRT
<213> ORGANISM: Artificial
<220> FEATURE:
<223> OTHER INFORMATION: peptide

<400> SEQUENCE: 93

Lys Met Ser Asn Asp Thr Val Val Leu
1               5

<210> SEQ ID NO 94
<211> LENGTH: 9
<212> TYPE: PRT
<213> ORGANISM: Artificial
<220> FEATURE:
<223> OTHER INFORMATION: peptide

<400> SEQUENCE: 94

Arg Leu Ser Asn Asp Thr Val Gly Leu
1               5

<210> SEQ ID NO 95
<211> LENGTH: 9
<212> TYPE: PRT
<213> ORGANISM: Artificial
<220> FEATURE:
<223> OTHER INFORMATION: peptide

<400> SEQUENCE: 95

Arg Met Ser Asn Asp Thr Val Glu Ile
1               5

<210> SEQ ID NO 96
<211> LENGTH: 9
<212> TYPE: PRT
<213> ORGANISM: Artificial
<220> FEATURE:
<223> OTHER INFORMATION: peptide

<400> SEQUENCE: 96

Thr Leu Ser Asn Asp Thr Val Trp Leu
1               5

<210> SEQ ID NO 97
<211> LENGTH: 9
<212> TYPE: PRT
<213> ORGANISM: Artificial
<220> FEATURE:
<223> OTHER INFORMATION: peptide

<400> SEQUENCE: 97

Ala Leu Leu Gly Pro Trp Leu Ile Val
1               5

<210> SEQ ID NO 98
<211> LENGTH: 9
<212> TYPE: PRT
<213> ORGANISM: Artificial
<220> FEATURE:
<223> OTHER INFORMATION: peptide

<400> SEQUENCE: 98

Phe Leu Leu Gly Pro Trp Leu Cys Leu
1               5

<210> SEQ ID NO 99
<211> LENGTH: 9
```

```
<212> TYPE: PRT
<213> ORGANISM: Artificial
<220> FEATURE:
<223> OTHER INFORMATION: peptide

<400> SEQUENCE: 99

Lys Leu Leu Gly Pro Trp Leu Ser Val
1               5

<210> SEQ ID NO 100
<211> LENGTH: 9
<212> TYPE: PRT
<213> ORGANISM: Artificial
<220> FEATURE:
<223> OTHER INFORMATION: peptide

<400> SEQUENCE: 100

Leu Leu Leu Gly Pro Trp Leu Leu Leu
1               5

<210> SEQ ID NO 101
<211> LENGTH: 9
<212> TYPE: PRT
<213> ORGANISM: Artificial
<220> FEATURE:
<223> OTHER INFORMATION: peptide

<400> SEQUENCE: 101

Tyr Leu Leu Gly Pro Trp Leu Leu Val
1               5

<210> SEQ ID NO 102
<211> LENGTH: 9
<212> TYPE: PRT
<213> ORGANISM: Artificial
<220> FEATURE:
<223> OTHER INFORMATION: peptide

<400> SEQUENCE: 102

Ile Leu Ile Leu Ala Ile Cys Gly Val
1               5

<210> SEQ ID NO 103
<211> LENGTH: 9
<212> TYPE: PRT
<213> ORGANISM: Artificial
<220> FEATURE:
<223> OTHER INFORMATION: peptide

<400> SEQUENCE: 103

Ile Met Ile Leu Ala Ile Cys Leu Val
1               5

<210> SEQ ID NO 104
<211> LENGTH: 9
<212> TYPE: PRT
<213> ORGANISM: Artificial
<220> FEATURE:
<223> OTHER INFORMATION: peptide

<400> SEQUENCE: 104

Arg Leu Ile Leu Ala Ile Cys Gly Leu
1               5

<210> SEQ ID NO 105
<211> LENGTH: 9
<212> TYPE: PRT
```

```
<213> ORGANISM: Artificial
<220> FEATURE:
<223> OTHER INFORMATION: peptide

<400> SEQUENCE: 105

Tyr Leu Ile Leu Ala Ile Cys Gly Val
1               5

<210> SEQ ID NO 106
<211> LENGTH: 9
<212> TYPE: PRT
<213> ORGANISM: Artificial
<220> FEATURE:
<223> OTHER INFORMATION: peptide

<400> SEQUENCE: 106

Lys Ile Phe Glu His Pro Glu Leu Leu
1               5

<210> SEQ ID NO 107
<211> LENGTH: 9
<212> TYPE: PRT
<213> ORGANISM: Artificial
<220> FEATURE:
<223> OTHER INFORMATION: peptide

<400> SEQUENCE: 107

Leu Ile Phe Glu His Pro Glu Arg Val
1               5

<210> SEQ ID NO 108
<211> LENGTH: 9
<212> TYPE: PRT
<213> ORGANISM: Artificial
<220> FEATURE:
<223> OTHER INFORMATION: peptide

<400> SEQUENCE: 108

Arg Val Phe Glu His Pro Glu Leu Val
1               5

<210> SEQ ID NO 109
<211> LENGTH: 9
<212> TYPE: PRT
<213> ORGANISM: Artificial
<220> FEATURE:
<223> OTHER INFORMATION: peptide

<400> SEQUENCE: 109

Tyr Val Phe Glu His Pro Glu Leu Leu
1               5

<210> SEQ ID NO 110
<211> LENGTH: 9
<212> TYPE: PRT
<213> ORGANISM: Artificial
<220> FEATURE:
<223> OTHER INFORMATION: peptide

<400> SEQUENCE: 110

Tyr Ile Phe Glu His Pro Glu Thr Ala
1               5

<210> SEQ ID NO 111
<211> LENGTH: 9
<212> TYPE: PRT
<213> ORGANISM: Artificial
```

```
<220> FEATURE:
<223> OTHER INFORMATION: peptide

<400> SEQUENCE: 111

Ala Leu Ala Phe Val Pro Leu Ala Val
1               5

<210> SEQ ID NO 112
<211> LENGTH: 9
<212> TYPE: PRT
<213> ORGANISM: Artificial
<220> FEATURE:
<223> OTHER INFORMATION: peptide

<400> SEQUENCE: 112

Ala Leu Ala Phe Val Pro Leu Ser Val
1               5

<210> SEQ ID NO 113
<211> LENGTH: 9
<212> TYPE: PRT
<213> ORGANISM: Artificial
<220> FEATURE:
<223> OTHER INFORMATION: peptide

<400> SEQUENCE: 113

Phe Leu Ala Phe Val Pro Leu Ile Leu
1               5

<210> SEQ ID NO 114
<211> LENGTH: 9
<212> TYPE: PRT
<213> ORGANISM: Artificial
<220> FEATURE:
<223> OTHER INFORMATION: peptide

<400> SEQUENCE: 114

Phe Leu Ala Phe Val Pro Leu Gln Leu
1               5

<210> SEQ ID NO 115
<211> LENGTH: 9
<212> TYPE: PRT
<213> ORGANISM: Artificial
<220> FEATURE:
<223> OTHER INFORMATION: peptide

<400> SEQUENCE: 115

Phe Leu Ala Phe Val Pro Leu Val Leu
1               5

<210> SEQ ID NO 116
<211> LENGTH: 9
<212> TYPE: PRT
<213> ORGANISM: Artificial
<220> FEATURE:
<223> OTHER INFORMATION: peptide

<400> SEQUENCE: 116

Phe Met Ala Phe Val Pro Leu Gln Leu
1               5

<210> SEQ ID NO 117
<211> LENGTH: 9
<212> TYPE: PRT
<213> ORGANISM: Artificial
<220> FEATURE:
```

<223> OTHER INFORMATION: peptide

<400> SEQUENCE: 117

Gly Met Ala Phe Val Pro Leu Leu Leu
1               5

<210> SEQ ID NO 118
<211> LENGTH: 9
<212> TYPE: PRT
<213> ORGANISM: Artificial
<220> FEATURE:
<223> OTHER INFORMATION: peptide

<400> SEQUENCE: 118

His Leu Ala Phe Val Pro Leu Leu Val
1               5

<210> SEQ ID NO 119
<211> LENGTH: 9
<212> TYPE: PRT
<213> ORGANISM: Artificial
<220> FEATURE:
<223> OTHER INFORMATION: peptide

<400> SEQUENCE: 119

Ile Leu Ala Phe Val Pro Leu Tyr Leu
1               5

<210> SEQ ID NO 120
<211> LENGTH: 9
<212> TYPE: PRT
<213> ORGANISM: Artificial
<220> FEATURE:
<223> OTHER INFORMATION: peptide

<400> SEQUENCE: 120

Ile Met Ala Phe Val Pro Leu Ala Val
1               5

<210> SEQ ID NO 121
<211> LENGTH: 9
<212> TYPE: PRT
<213> ORGANISM: Artificial
<220> FEATURE:
<223> OTHER INFORMATION: peptide

<400> SEQUENCE: 121

Ile Met Ala Phe Val Pro Leu Ile Val
1               5

<210> SEQ ID NO 122
<211> LENGTH: 9
<212> TYPE: PRT
<213> ORGANISM: Artificial
<220> FEATURE:
<223> OTHER INFORMATION: peptide

<400> SEQUENCE: 122

Ile Met Ala Phe Val Pro Leu Val Val
1               5

<210> SEQ ID NO 123
<211> LENGTH: 9
<212> TYPE: PRT
<213> ORGANISM: Artificial
<220> FEATURE:
<223> OTHER INFORMATION: peptide

<400> SEQUENCE: 123

Leu Leu Ala Phe Val Pro Leu Ala Leu
1               5

<210> SEQ ID NO 124
<211> LENGTH: 9
<212> TYPE: PRT
<213> ORGANISM: Artificial
<220> FEATURE:
<223> OTHER INFORMATION: peptide

<400> SEQUENCE: 124

Leu Leu Ala Phe Val Pro Leu Asp Val
1               5

<210> SEQ ID NO 125
<211> LENGTH: 9
<212> TYPE: PRT
<213> ORGANISM: Artificial
<220> FEATURE:
<223> OTHER INFORMATION: peptide

<400> SEQUENCE: 125

Leu Leu Ala Phe Val Pro Leu Met Leu
1               5

<210> SEQ ID NO 126
<211> LENGTH: 9
<212> TYPE: PRT
<213> ORGANISM: Artificial
<220> FEATURE:
<223> OTHER INFORMATION: peptide

<400> SEQUENCE: 126

Leu Leu Ala Phe Val Pro Leu Ser Leu
1               5

<210> SEQ ID NO 127
<211> LENGTH: 9
<212> TYPE: PRT
<213> ORGANISM: Artificial
<220> FEATURE:
<223> OTHER INFORMATION: peptide

<400> SEQUENCE: 127

Leu Met Ala Phe Val Pro Leu Thr Leu
1               5

<210> SEQ ID NO 128
<211> LENGTH: 9
<212> TYPE: PRT
<213> ORGANISM: Artificial
<220> FEATURE:
<223> OTHER INFORMATION: peptide

<400> SEQUENCE: 128

Thr Leu Ala Phe Val Pro Leu Ala Val
1               5

<210> SEQ ID NO 129
<211> LENGTH: 9
<212> TYPE: PRT
<213> ORGANISM: Artificial
<220> FEATURE:
<223> OTHER INFORMATION: peptide

```
<400> SEQUENCE: 129

Val Leu Ala Phe Val Pro Leu Leu Val
1               5

<210> SEQ ID NO 130
<211> LENGTH: 9
<212> TYPE: PRT
<213> ORGANISM: Artificial
<220> FEATURE:
<223> OTHER INFORMATION: peptide

<400> SEQUENCE: 130

Val Met Ala Phe Val Pro Leu Val Val
1               5

<210> SEQ ID NO 131
<211> LENGTH: 9
<212> TYPE: PRT
<213> ORGANISM: Artificial
<220> FEATURE:
<223> OTHER INFORMATION: peptide

<400> SEQUENCE: 131

Phe Leu Tyr Phe Gly Met Leu Leu Leu
1               5

<210> SEQ ID NO 132
<211> LENGTH: 9
<212> TYPE: PRT
<213> ORGANISM: Artificial
<220> FEATURE:
<223> OTHER INFORMATION: peptide

<400> SEQUENCE: 132

Gly Leu Tyr Phe Gly Met Leu His Met
1               5

<210> SEQ ID NO 133
<211> LENGTH: 9
<212> TYPE: PRT
<213> ORGANISM: Artificial
<220> FEATURE:
<223> OTHER INFORMATION: peptide

<400> SEQUENCE: 133

Leu Leu Tyr Phe Gly Met Leu Gly Leu
1               5

<210> SEQ ID NO 134
<211> LENGTH: 9
<212> TYPE: PRT
<213> ORGANISM: Artificial
<220> FEATURE:
<223> OTHER INFORMATION: peptide

<400> SEQUENCE: 134

Leu Leu Tyr Phe Gly Met Leu Leu Leu
1               5

<210> SEQ ID NO 135
<211> LENGTH: 9
<212> TYPE: PRT
<213> ORGANISM: Artificial
<220> FEATURE:
<223> OTHER INFORMATION: peptide

<400> SEQUENCE: 135
```

```
Thr Met Tyr Phe Gly Met Leu Tyr Leu
1               5

<210> SEQ ID NO 136
<211> LENGTH: 9
<212> TYPE: PRT
<213> ORGANISM: Artificial
<220> FEATURE:
<223> OTHER INFORMATION: peptide

<400> SEQUENCE: 136

Val Leu Tyr Phe Gly Met Leu Leu Ile
1               5

<210> SEQ ID NO 137
<211> LENGTH: 9
<212> TYPE: PRT
<213> ORGANISM: Artificial
<220> FEATURE:
<223> OTHER INFORMATION: peptide

<400> SEQUENCE: 137

Cys Leu Ile Asp Lys Thr Ser Val Val
1               5

<210> SEQ ID NO 138
<211> LENGTH: 9
<212> TYPE: PRT
<213> ORGANISM: Artificial
<220> FEATURE:
<223> OTHER INFORMATION: peptide

<400> SEQUENCE: 138

Phe Leu Ile Asp Lys Thr Ser Ala Ala
1               5

<210> SEQ ID NO 139
<211> LENGTH: 9
<212> TYPE: PRT
<213> ORGANISM: Artificial
<220> FEATURE:
<223> OTHER INFORMATION: peptide

<400> SEQUENCE: 139

Ile Leu Ile Asp Lys Thr Ser Gly Ala
1               5

<210> SEQ ID NO 140
<211> LENGTH: 9
<212> TYPE: PRT
<213> ORGANISM: Artificial
<220> FEATURE:
<223> OTHER INFORMATION: peptide

<400> SEQUENCE: 140

Ile Leu Ile Asp Lys Thr Ser Gly Val
1               5

<210> SEQ ID NO 141
<211> LENGTH: 9
<212> TYPE: PRT
<213> ORGANISM: Artificial
<220> FEATURE:
<223> OTHER INFORMATION: peptide

<400> SEQUENCE: 141
```

```
Ile Met Ile Asp Lys Thr Ser Thr Val
1               5

<210> SEQ ID NO 142
<211> LENGTH: 9
<212> TYPE: PRT
<213> ORGANISM: Artificial
<220> FEATURE:
<223> OTHER INFORMATION: peptide

<400> SEQUENCE: 142

Val Ile Ile Asp Lys Thr Ser Ser Val
1               5

<210> SEQ ID NO 143
<211> LENGTH: 9
<212> TYPE: PRT
<213> ORGANISM: Artificial
<220> FEATURE:
<223> OTHER INFORMATION: peptide

<400> SEQUENCE: 143

Val Leu Ile Asp Lys Thr Ser Gln Leu
1               5

<210> SEQ ID NO 144
<211> LENGTH: 9
<212> TYPE: PRT
<213> ORGANISM: Artificial
<220> FEATURE:
<223> OTHER INFORMATION: peptide

<400> SEQUENCE: 144

Val Leu Ile Asp Lys Thr Ser Ser Val
1               5

<210> SEQ ID NO 145
<211> LENGTH: 9
<212> TYPE: PRT
<213> ORGANISM: Artificial
<220> FEATURE:
<223> OTHER INFORMATION: peptide

<400> SEQUENCE: 145

Tyr Leu Ile Asp Lys Thr Ser Asn Ile
1               5

<210> SEQ ID NO 146
<211> LENGTH: 9
<212> TYPE: PRT
<213> ORGANISM: Artificial
<220> FEATURE:
<223> OTHER INFORMATION: peptide

<400> SEQUENCE: 146

Tyr Leu Ile Asp Lys Thr Ser Asn Leu
1               5

<210> SEQ ID NO 147
<211> LENGTH: 9
<212> TYPE: PRT
<213> ORGANISM: Artificial
<220> FEATURE:
<223> OTHER INFORMATION: peptide

<400> SEQUENCE: 147

Tyr Leu Ile Asp Lys Thr Ser Thr Val
```

1               5

<210> SEQ ID NO 148
<211> LENGTH: 9
<212> TYPE: PRT
<213> ORGANISM: Artificial
<220> FEATURE:
<223> OTHER INFORMATION: peptide

<400> SEQUENCE: 148

Phe Ile Leu Leu Phe Ala Thr His Val
1               5

<210> SEQ ID NO 149
<211> LENGTH: 9
<212> TYPE: PRT
<213> ORGANISM: Artificial
<220> FEATURE:
<223> OTHER INFORMATION: peptide

<400> SEQUENCE: 149

Phe Leu Leu Leu Phe Ala Thr Ser Val
1               5

<210> SEQ ID NO 150
<211> LENGTH: 9
<212> TYPE: PRT
<213> ORGANISM: Artificial
<220> FEATURE:
<223> OTHER INFORMATION: peptide

<400> SEQUENCE: 150

Leu Leu Leu Leu Phe Ala Thr Ala Val
1               5

<210> SEQ ID NO 151
<211> LENGTH: 9
<212> TYPE: PRT
<213> ORGANISM: Artificial
<220> FEATURE:
<223> OTHER INFORMATION: peptide

<400> SEQUENCE: 151

Leu Leu Leu Leu Phe Ala Thr Ser Val
1               5

<210> SEQ ID NO 152
<211> LENGTH: 9
<212> TYPE: PRT
<213> ORGANISM: Artificial
<220> FEATURE:
<223> OTHER INFORMATION: peptide

<400> SEQUENCE: 152

Leu Met Leu Leu Phe Ala Thr Ser Val
1               5

<210> SEQ ID NO 153
<211> LENGTH: 9
<212> TYPE: PRT
<213> ORGANISM: Artificial
<220> FEATURE:
<223> OTHER INFORMATION: peptide

<400> SEQUENCE: 153

Met Met Leu Leu Phe Ala Thr Leu Leu
1               5

```
<210> SEQ ID NO 154
<211> LENGTH: 9
<212> TYPE: PRT
<213> ORGANISM: Artificial
<220> FEATURE:
<223> OTHER INFORMATION: peptide

<400> SEQUENCE: 154

Tyr Leu Leu Leu Phe Ala Thr Asn Val
1               5

<210> SEQ ID NO 155
<211> LENGTH: 9
<212> TYPE: PRT
<213> ORGANISM: Artificial
<220> FEATURE:
<223> OTHER INFORMATION: peptide

<400> SEQUENCE: 155

Tyr Leu Leu Leu Phe Ala Thr Tyr Leu
1               5

<210> SEQ ID NO 156
<211> LENGTH: 9
<212> TYPE: PRT
<213> ORGANISM: Artificial
<220> FEATURE:
<223> OTHER INFORMATION: peptide

<400> SEQUENCE: 156

Ile Leu Val Gly Ile Cys Leu Gly Val
1               5

<210> SEQ ID NO 157
<211> LENGTH: 9
<212> TYPE: PRT
<213> ORGANISM: Artificial
<220> FEATURE:
<223> OTHER INFORMATION: peptide

<400> SEQUENCE: 157

Ser Ile Val Gly Ile Cys Leu Asn Val
1               5

<210> SEQ ID NO 158
<211> LENGTH: 9
<212> TYPE: PRT
<213> ORGANISM: Artificial
<220> FEATURE:
<223> OTHER INFORMATION: peptide

<400> SEQUENCE: 158

Lys Leu Ile Lys Tyr Phe Leu Lys Val
1               5

<210> SEQ ID NO 159
<211> LENGTH: 9
<212> TYPE: PRT
<213> ORGANISM: Artificial
<220> FEATURE:
<223> OTHER INFORMATION: peptide

<400> SEQUENCE: 159

Lys Leu Ile Lys Tyr Phe Leu Val Val
1               5
```

```
<210> SEQ ID NO 160
<211> LENGTH: 9
<212> TYPE: PRT
<213> ORGANISM: Artificial
<220> FEATURE:
<223> OTHER INFORMATION: peptide

<400> SEQUENCE: 160

Met Met Ile Lys Tyr Phe Leu Cys Val
1               5

<210> SEQ ID NO 161
<211> LENGTH: 9
<212> TYPE: PRT
<213> ORGANISM: Artificial
<220> FEATURE:
<223> OTHER INFORMATION: peptide

<400> SEQUENCE: 161

Asn Leu Ile Lys Tyr Phe Leu Tyr Val
1               5

<210> SEQ ID NO 162
<211> LENGTH: 9
<212> TYPE: PRT
<213> ORGANISM: Artificial
<220> FEATURE:
<223> OTHER INFORMATION: peptide

<400> SEQUENCE: 162

Ser Leu Ile Lys Tyr Phe Leu Ser Ile
1               5

<210> SEQ ID NO 163
<211> LENGTH: 9
<212> TYPE: PRT
<213> ORGANISM: Artificial
<220> FEATURE:
<223> OTHER INFORMATION: peptide

<400> SEQUENCE: 163

Ala Leu Val Leu Ala Leu Val Gly Val
1               5

<210> SEQ ID NO 164
<211> LENGTH: 9
<212> TYPE: PRT
<213> ORGANISM: Artificial
<220> FEATURE:
<223> OTHER INFORMATION: peptide

<400> SEQUENCE: 164

Ala Leu Val Leu Ala Leu Val Pro Val
1               5

<210> SEQ ID NO 165
<211> LENGTH: 9
<212> TYPE: PRT
<213> ORGANISM: Artificial
<220> FEATURE:
<223> OTHER INFORMATION: peptide

<400> SEQUENCE: 165

Gly Leu Val Leu Ala Leu Val Gly Val
1               5
```

```
<210> SEQ ID NO 166
<211> LENGTH: 9
<212> TYPE: PRT
<213> ORGANISM: Artificial
<220> FEATURE:
<223> OTHER INFORMATION: peptide

<400> SEQUENCE: 166

Asn Leu Val Leu Ala Leu Val Glu Val
1               5

<210> SEQ ID NO 167
<211> LENGTH: 9
<212> TYPE: PRT
<213> ORGANISM: Artificial
<220> FEATURE:
<223> OTHER INFORMATION: peptide

<400> SEQUENCE: 167

Ser Leu Val Leu Ala Leu Val Gly Val
1               5

<210> SEQ ID NO 168
<211> LENGTH: 9
<212> TYPE: PRT
<213> ORGANISM: Artificial
<220> FEATURE:
<223> OTHER INFORMATION: peptide

<400> SEQUENCE: 168

Ser Leu Val Leu Ala Leu Val Ser Val
1               5

<210> SEQ ID NO 169
<211> LENGTH: 9
<212> TYPE: PRT
<213> ORGANISM: Artificial
<220> FEATURE:
<223> OTHER INFORMATION: peptide

<400> SEQUENCE: 169

Ser Leu Val Leu Ala Leu Val Tyr Val
1               5

<210> SEQ ID NO 170
<211> LENGTH: 9
<212> TYPE: PRT
<213> ORGANISM: Artificial
<220> FEATURE:
<223> OTHER INFORMATION: peptide

<400> SEQUENCE: 170

Thr Leu Val Leu Ala Leu Val Ser Val
1               5

<210> SEQ ID NO 171
<211> LENGTH: 9
<212> TYPE: PRT
<213> ORGANISM: Artificial
<220> FEATURE:
<223> OTHER INFORMATION: peptide

<400> SEQUENCE: 171

Ala Leu Ala Leu Val Leu Ala Leu Leu
1               5

<210> SEQ ID NO 172
```

```
<211> LENGTH: 9
<212> TYPE: PRT
<213> ORGANISM: Artificial
<220> FEATURE:
<223> OTHER INFORMATION: peptide

<400> SEQUENCE: 172

Ala Leu Ala Leu Val Leu Ala Met Leu
1               5

<210> SEQ ID NO 173
<211> LENGTH: 9
<212> TYPE: PRT
<213> ORGANISM: Artificial
<220> FEATURE:
<223> OTHER INFORMATION: peptide

<400> SEQUENCE: 173

Ala Leu Ala Leu Val Leu Ala Thr Val
1               5

<210> SEQ ID NO 174
<211> LENGTH: 9
<212> TYPE: PRT
<213> ORGANISM: Artificial
<220> FEATURE:
<223> OTHER INFORMATION: peptide

<400> SEQUENCE: 174

Phe Leu Ala Leu Val Leu Ala Ala Ala
1               5

<210> SEQ ID NO 175
<211> LENGTH: 9
<212> TYPE: PRT
<213> ORGANISM: Artificial
<220> FEATURE:
<223> OTHER INFORMATION: peptide

<400> SEQUENCE: 175

Phe Leu Ala Leu Val Leu Ala Ala Leu
1               5

<210> SEQ ID NO 176
<211> LENGTH: 9
<212> TYPE: PRT
<213> ORGANISM: Artificial
<220> FEATURE:
<223> OTHER INFORMATION: peptide

<400> SEQUENCE: 176

Phe Leu Ala Leu Val Leu Ala Gly Leu
1               5

<210> SEQ ID NO 177
<211> LENGTH: 9
<212> TYPE: PRT
<213> ORGANISM: Artificial
<220> FEATURE:
<223> OTHER INFORMATION: peptide

<400> SEQUENCE: 177

Phe Leu Ala Leu Val Leu Ala Gly Val
1               5

<210> SEQ ID NO 178
<211> LENGTH: 9
```

```
<212> TYPE: PRT
<213> ORGANISM: Artificial
<220> FEATURE:
<223> OTHER INFORMATION: peptide

<400> SEQUENCE: 178

Phe Leu Ala Leu Val Leu Ala Leu Leu
1               5

<210> SEQ ID NO 179
<211> LENGTH: 9
<212> TYPE: PRT
<213> ORGANISM: Artificial
<220> FEATURE:
<223> OTHER INFORMATION: peptide

<400> SEQUENCE: 179

Phe Leu Ala Leu Val Leu Ala Met Leu
1               5

<210> SEQ ID NO 180
<211> LENGTH: 9
<212> TYPE: PRT
<213> ORGANISM: Artificial
<220> FEATURE:
<223> OTHER INFORMATION: peptide

<400> SEQUENCE: 180

Phe Leu Ala Leu Val Leu Ala Thr Leu
1               5

<210> SEQ ID NO 181
<211> LENGTH: 9
<212> TYPE: PRT
<213> ORGANISM: Artificial
<220> FEATURE:
<223> OTHER INFORMATION: peptide

<400> SEQUENCE: 181

Gly Leu Ala Leu Val Leu Ala Ala Ile
1               5

<210> SEQ ID NO 182
<211> LENGTH: 9
<212> TYPE: PRT
<213> ORGANISM: Artificial
<220> FEATURE:
<223> OTHER INFORMATION: peptide

<400> SEQUENCE: 182

Gly Leu Ala Leu Val Leu Ala Ala Leu
1               5

<210> SEQ ID NO 183
<211> LENGTH: 9
<212> TYPE: PRT
<213> ORGANISM: Artificial
<220> FEATURE:
<223> OTHER INFORMATION: peptide

<400> SEQUENCE: 183

Gly Leu Ala Leu Val Leu Ala Ala Val
1               5

<210> SEQ ID NO 184
<211> LENGTH: 9
<212> TYPE: PRT
```

```
<213> ORGANISM: Artificial
<220> FEATURE:
<223> OTHER INFORMATION: peptide

<400> SEQUENCE: 184

Gly Leu Ala Leu Val Leu Ala Leu Leu
1               5

<210> SEQ ID NO 185
<211> LENGTH: 9
<212> TYPE: PRT
<213> ORGANISM: Artificial
<220> FEATURE:
<223> OTHER INFORMATION: peptide

<400> SEQUENCE: 185

Gly Leu Ala Leu Val Leu Ala Leu Val
1               5

<210> SEQ ID NO 186
<211> LENGTH: 9
<212> TYPE: PRT
<213> ORGANISM: Artificial
<220> FEATURE:
<223> OTHER INFORMATION: peptide

<400> SEQUENCE: 186

Gly Leu Ala Leu Val Leu Ala Asn Ile
1               5

<210> SEQ ID NO 187
<211> LENGTH: 9
<212> TYPE: PRT
<213> ORGANISM: Artificial
<220> FEATURE:
<223> OTHER INFORMATION: peptide

<400> SEQUENCE: 187

Gly Leu Ala Leu Val Leu Ala Thr Leu
1               5

<210> SEQ ID NO 188
<211> LENGTH: 9
<212> TYPE: PRT
<213> ORGANISM: Artificial
<220> FEATURE:
<223> OTHER INFORMATION: peptide

<400> SEQUENCE: 188

Gly Leu Ala Leu Val Leu Ala Thr Val
1               5

<210> SEQ ID NO 189
<211> LENGTH: 9
<212> TYPE: PRT
<213> ORGANISM: Artificial
<220> FEATURE:
<223> OTHER INFORMATION: peptide

<400> SEQUENCE: 189

Gly Leu Ala Leu Val Leu Ala Val Val
1               5

<210> SEQ ID NO 190
<211> LENGTH: 9
<212> TYPE: PRT
<213> ORGANISM: Artificial
```

```
<220> FEATURE:
<223> OTHER INFORMATION: peptide

<400> SEQUENCE: 190

Gly Met Ala Leu Val Leu Ala Ala Val
1               5

<210> SEQ ID NO 191
<211> LENGTH: 9
<212> TYPE: PRT
<213> ORGANISM: Artificial
<220> FEATURE:
<223> OTHER INFORMATION: peptide

<400> SEQUENCE: 191

Ile Leu Ala Leu Val Leu Ala Met Val
1               5

<210> SEQ ID NO 192
<211> LENGTH: 9
<212> TYPE: PRT
<213> ORGANISM: Artificial
<220> FEATURE:
<223> OTHER INFORMATION: peptide

<400> SEQUENCE: 192

Ile Leu Ala Leu Val Leu Ala Arg Val
1               5

<210> SEQ ID NO 193
<211> LENGTH: 9
<212> TYPE: PRT
<213> ORGANISM: Artificial
<220> FEATURE:
<223> OTHER INFORMATION: peptide

<400> SEQUENCE: 193

Ile Leu Ala Leu Val Leu Ala Tyr Leu
1               5

<210> SEQ ID NO 194
<211> LENGTH: 9
<212> TYPE: PRT
<213> ORGANISM: Artificial
<220> FEATURE:
<223> OTHER INFORMATION: peptide

<400> SEQUENCE: 194

Lys Leu Ala Leu Val Leu Ala Met Leu
1               5

<210> SEQ ID NO 195
<211> LENGTH: 9
<212> TYPE: PRT
<213> ORGANISM: Artificial
<220> FEATURE:
<223> OTHER INFORMATION: peptide

<400> SEQUENCE: 195

Leu Leu Ala Leu Val Leu Ala Glu Val
1               5

<210> SEQ ID NO 196
<211> LENGTH: 9
<212> TYPE: PRT
<213> ORGANISM: Artificial
<220> FEATURE:
```

```
<223> OTHER INFORMATION: peptide

<400> SEQUENCE: 196

Met Leu Ala Leu Val Leu Ala Gly Leu
1               5

<210> SEQ ID NO 197
<211> LENGTH: 9
<212> TYPE: PRT
<213> ORGANISM: Artificial
<220> FEATURE:
<223> OTHER INFORMATION: peptide

<400> SEQUENCE: 197

Ser Leu Ala Leu Val Leu Ala Leu Leu
1               5

<210> SEQ ID NO 198
<211> LENGTH: 9
<212> TYPE: PRT
<213> ORGANISM: Artificial
<220> FEATURE:
<223> OTHER INFORMATION: peptide

<400> SEQUENCE: 198

Ser Leu Ala Leu Val Leu Ala Leu Val
1               5

<210> SEQ ID NO 199
<211> LENGTH: 9
<212> TYPE: PRT
<213> ORGANISM: Artificial
<220> FEATURE:
<223> OTHER INFORMATION: peptide

<400> SEQUENCE: 199

Ser Leu Ala Leu Val Leu Ala Met Leu
1               5

<210> SEQ ID NO 200
<211> LENGTH: 9
<212> TYPE: PRT
<213> ORGANISM: Artificial
<220> FEATURE:
<223> OTHER INFORMATION: peptide

<400> SEQUENCE: 200

Val Leu Ala Leu Val Leu Ala Glu Leu
1               5

<210> SEQ ID NO 201
<211> LENGTH: 9
<212> TYPE: PRT
<213> ORGANISM: Artificial
<220> FEATURE:
<223> OTHER INFORMATION: peptide

<400> SEQUENCE: 201

Val Leu Ala Leu Val Leu Ala Glu Val
1               5

<210> SEQ ID NO 202
<211> LENGTH: 9
<212> TYPE: PRT
<213> ORGANISM: Artificial
<220> FEATURE:
<223> OTHER INFORMATION: peptide
```

```
<400> SEQUENCE: 202

Val Leu Ala Leu Val Leu Ala Gly Val
1               5

<210> SEQ ID NO 203
<211> LENGTH: 9
<212> TYPE: PRT
<213> ORGANISM: Artificial
<220> FEATURE:
<223> OTHER INFORMATION: peptide

<400> SEQUENCE: 203

Val Leu Ala Leu Val Leu Ala Leu Val
1               5

<210> SEQ ID NO 204
<211> LENGTH: 9
<212> TYPE: PRT
<213> ORGANISM: Artificial
<220> FEATURE:
<223> OTHER INFORMATION: peptide

<400> SEQUENCE: 204

Val Leu Ala Leu Val Leu Ala Met Val
1               5

<210> SEQ ID NO 205
<211> LENGTH: 9
<212> TYPE: PRT
<213> ORGANISM: Artificial
<220> FEATURE:
<223> OTHER INFORMATION: peptide

<400> SEQUENCE: 205

Val Leu Ala Leu Val Leu Ala Thr Val
1               5

<210> SEQ ID NO 206
<211> LENGTH: 9
<212> TYPE: PRT
<213> ORGANISM: Artificial
<220> FEATURE:
<223> OTHER INFORMATION: peptide

<400> SEQUENCE: 206

Tyr Leu Ala Leu Val Leu Ala Phe Leu
1               5

<210> SEQ ID NO 207
<211> LENGTH: 9
<212> TYPE: PRT
<213> ORGANISM: Artificial
<220> FEATURE:
<223> OTHER INFORMATION: peptide

<400> SEQUENCE: 207

Tyr Leu Ala Leu Val Leu Ala Leu Ile
1               5

<210> SEQ ID NO 208
<211> LENGTH: 9
<212> TYPE: PRT
<213> ORGANISM: Artificial
<220> FEATURE:
<223> OTHER INFORMATION: peptide
```

```
<400> SEQUENCE: 208

Tyr Leu Ala Leu Val Leu Ala Leu Leu
1               5

<210> SEQ ID NO 209
<211> LENGTH: 9
<212> TYPE: PRT
<213> ORGANISM: Artificial
<220> FEATURE:
<223> OTHER INFORMATION: peptide

<400> SEQUENCE: 209

Tyr Leu Ala Leu Val Leu Ala Met Leu
1               5

<210> SEQ ID NO 210
<211> LENGTH: 9
<212> TYPE: PRT
<213> ORGANISM: Artificial
<220> FEATURE:
<223> OTHER INFORMATION: peptide

<400> SEQUENCE: 210

Ala Leu Phe Gly Ala Pro Ala Ala Val
1               5

<210> SEQ ID NO 211
<211> LENGTH: 9
<212> TYPE: PRT
<213> ORGANISM: Artificial
<220> FEATURE:
<223> OTHER INFORMATION: peptide

<400> SEQUENCE: 211

Ala Leu Phe Gly Ala Pro Ala Lys Leu
1               5

<210> SEQ ID NO 212
<211> LENGTH: 9
<212> TYPE: PRT
<213> ORGANISM: Artificial
<220> FEATURE:
<223> OTHER INFORMATION: peptide

<400> SEQUENCE: 212

Phe Leu Phe Gly Ala Pro Ala Ser Ala
1               5

<210> SEQ ID NO 213
<211> LENGTH: 9
<212> TYPE: PRT
<213> ORGANISM: Artificial
<220> FEATURE:
<223> OTHER INFORMATION: peptide

<400> SEQUENCE: 213

Gly Leu Phe Gly Ala Pro Ala Phe Ile
1               5

<210> SEQ ID NO 214
<211> LENGTH: 9
<212> TYPE: PRT
<213> ORGANISM: Artificial
<220> FEATURE:
<223> OTHER INFORMATION: peptide

<400> SEQUENCE: 214
```

```
Leu Leu Phe Gly Ala Pro Ala Ala Leu
1               5

<210> SEQ ID NO 215
<211> LENGTH: 9
<212> TYPE: PRT
<213> ORGANISM: Artificial
<220> FEATURE:
<223> OTHER INFORMATION: peptide

<400> SEQUENCE: 215

Leu Leu Phe Gly Ala Pro Ala Gly Ile
1               5

<210> SEQ ID NO 216
<211> LENGTH: 9
<212> TYPE: PRT
<213> ORGANISM: Artificial
<220> FEATURE:
<223> OTHER INFORMATION: peptide

<400> SEQUENCE: 216

Leu Leu Phe Gly Ala Pro Ala Gly Leu
1               5

<210> SEQ ID NO 217
<211> LENGTH: 9
<212> TYPE: PRT
<213> ORGANISM: Artificial
<220> FEATURE:
<223> OTHER INFORMATION: peptide

<400> SEQUENCE: 217

Leu Leu Phe Gly Ala Pro Ala Gly Val
1               5

<210> SEQ ID NO 218
<211> LENGTH: 9
<212> TYPE: PRT
<213> ORGANISM: Artificial
<220> FEATURE:
<223> OTHER INFORMATION: peptide

<400> SEQUENCE: 218

Leu Leu Phe Gly Ala Pro Ala Leu Leu
1               5

<210> SEQ ID NO 219
<211> LENGTH: 9
<212> TYPE: PRT
<213> ORGANISM: Artificial
<220> FEATURE:
<223> OTHER INFORMATION: peptide

<400> SEQUENCE: 219

Leu Met Phe Gly Ala Pro Ala Phe Val
1               5

<210> SEQ ID NO 220
<211> LENGTH: 9
<212> TYPE: PRT
<213> ORGANISM: Artificial
<220> FEATURE:
<223> OTHER INFORMATION: peptide

<400> SEQUENCE: 220
```

```
Leu Met Phe Gly Ala Pro Ala Leu Val
1               5

<210> SEQ ID NO 221
<211> LENGTH: 9
<212> TYPE: PRT
<213> ORGANISM: Artificial
<220> FEATURE:
<223> OTHER INFORMATION: peptide

<400> SEQUENCE: 221

Met Leu Phe Gly Ala Pro Ala Glu Ala
1               5

<210> SEQ ID NO 222
<211> LENGTH: 9
<212> TYPE: PRT
<213> ORGANISM: Artificial
<220> FEATURE:
<223> OTHER INFORMATION: peptide

<400> SEQUENCE: 222

Ser Met Phe Gly Ala Pro Ala His Val
1               5

<210> SEQ ID NO 223
<211> LENGTH: 9
<212> TYPE: PRT
<213> ORGANISM: Artificial
<220> FEATURE:
<223> OTHER INFORMATION: peptide

<400> SEQUENCE: 223

Val Leu Phe Gly Ala Pro Ala Asn Leu
1               5

<210> SEQ ID NO 224
<211> LENGTH: 9
<212> TYPE: PRT
<213> ORGANISM: Artificial
<220> FEATURE:
<223> OTHER INFORMATION: peptide

<400> SEQUENCE: 224

Val Leu Phe Gly Ala Pro Ala Tyr Leu
1               5

<210> SEQ ID NO 225
<211> LENGTH: 9
<212> TYPE: PRT
<213> ORGANISM: Artificial
<220> FEATURE:
<223> OTHER INFORMATION: peptide

<400> SEQUENCE: 225

Tyr Leu Phe Gly Ala Pro Ala Ala Ala
1               5

<210> SEQ ID NO 226
<211> LENGTH: 9
<212> TYPE: PRT
<213> ORGANISM: Artificial
<220> FEATURE:
<223> OTHER INFORMATION: peptide

<400> SEQUENCE: 226

Phe Leu Pro Gly Leu Leu Phe Ser Val
```

```
1               5
```

<210> SEQ ID NO 227
<211> LENGTH: 9
<212> TYPE: PRT
<213> ORGANISM: Artificial
<220> FEATURE:
<223> OTHER INFORMATION: peptide

<400> SEQUENCE: 227

```
Phe Met Pro Gly Leu Leu Phe Gly Ala
1               5
```

<210> SEQ ID NO 228
<211> LENGTH: 9
<212> TYPE: PRT
<213> ORGANISM: Artificial
<220> FEATURE:
<223> OTHER INFORMATION: peptide

<400> SEQUENCE: 228

```
Phe Val Pro Gly Leu Leu Phe Gly Val
1               5
```

<210> SEQ ID NO 229
<211> LENGTH: 9
<212> TYPE: PRT
<213> ORGANISM: Artificial
<220> FEATURE:
<223> OTHER INFORMATION: peptide

<400> SEQUENCE: 229

```
Gly Leu Pro Gly Leu Leu Phe Glu Leu
1               5
```

<210> SEQ ID NO 230
<211> LENGTH: 9
<212> TYPE: PRT
<213> ORGANISM: Artificial
<220> FEATURE:
<223> OTHER INFORMATION: peptide

<400> SEQUENCE: 230

```
Ile Leu Pro Gly Leu Leu Phe Ala Ile
1               5
```

<210> SEQ ID NO 231
<211> LENGTH: 9
<212> TYPE: PRT
<213> ORGANISM: Artificial
<220> FEATURE:
<223> OTHER INFORMATION: peptide

<400> SEQUENCE: 231

```
Ile Leu Pro Gly Leu Leu Phe Gly Leu
1               5
```

<210> SEQ ID NO 232
<211> LENGTH: 9
<212> TYPE: PRT
<213> ORGANISM: Artificial
<220> FEATURE:
<223> OTHER INFORMATION: peptide

<400> SEQUENCE: 232

```
Ile Leu Pro Gly Leu Leu Phe Leu Ile
1               5
```

```
<210> SEQ ID NO 233
<211> LENGTH: 9
<212> TYPE: PRT
<213> ORGANISM: Artificial
<220> FEATURE:
<223> OTHER INFORMATION: peptide

<400> SEQUENCE: 233

Ile Leu Pro Gly Leu Leu Phe Ser Leu
1               5

<210> SEQ ID NO 234
<211> LENGTH: 9
<212> TYPE: PRT
<213> ORGANISM: Artificial
<220> FEATURE:
<223> OTHER INFORMATION: peptide

<400> SEQUENCE: 234

Ile Leu Pro Gly Leu Leu Phe Tyr Ile
1               5

<210> SEQ ID NO 235
<211> LENGTH: 9
<212> TYPE: PRT
<213> ORGANISM: Artificial
<220> FEATURE:
<223> OTHER INFORMATION: peptide

<400> SEQUENCE: 235

Ile Leu Pro Gly Leu Leu Phe Tyr Met
1               5

<210> SEQ ID NO 236
<211> LENGTH: 9
<212> TYPE: PRT
<213> ORGANISM: Artificial
<220> FEATURE:
<223> OTHER INFORMATION: peptide

<400> SEQUENCE: 236

Ile Met Pro Gly Leu Leu Phe His Ile
1               5

<210> SEQ ID NO 237
<211> LENGTH: 9
<212> TYPE: PRT
<213> ORGANISM: Artificial
<220> FEATURE:
<223> OTHER INFORMATION: peptide

<400> SEQUENCE: 237

Ile Met Pro Gly Leu Leu Phe Gln Val
1               5

<210> SEQ ID NO 238
<211> LENGTH: 9
<212> TYPE: PRT
<213> ORGANISM: Artificial
<220> FEATURE:
<223> OTHER INFORMATION: peptide

<400> SEQUENCE: 238

Ile Met Pro Gly Leu Leu Phe Tyr Val
1               5
```

<210> SEQ ID NO 239
<211> LENGTH: 9
<212> TYPE: PRT
<213> ORGANISM: Artificial
<220> FEATURE:
<223> OTHER INFORMATION: peptide

<400> SEQUENCE: 239

Lys Leu Pro Gly Leu Leu Phe His Ala
1               5

<210> SEQ ID NO 240
<211> LENGTH: 9
<212> TYPE: PRT
<213> ORGANISM: Artificial
<220> FEATURE:
<223> OTHER INFORMATION: peptide

<400> SEQUENCE: 240

Lys Leu Pro Gly Leu Leu Phe Ser Val
1               5

<210> SEQ ID NO 241
<211> LENGTH: 9
<212> TYPE: PRT
<213> ORGANISM: Artificial
<220> FEATURE:
<223> OTHER INFORMATION: peptide

<400> SEQUENCE: 241

Leu Leu Pro Gly Leu Leu Phe Gly Leu
1               5

<210> SEQ ID NO 242
<211> LENGTH: 9
<212> TYPE: PRT
<213> ORGANISM: Artificial
<220> FEATURE:
<223> OTHER INFORMATION: peptide

<400> SEQUENCE: 242

Leu Leu Pro Gly Leu Leu Phe Thr Leu
1               5

<210> SEQ ID NO 243
<211> LENGTH: 9
<212> TYPE: PRT
<213> ORGANISM: Artificial
<220> FEATURE:
<223> OTHER INFORMATION: peptide

<400> SEQUENCE: 243

Leu Leu Pro Gly Leu Leu Phe Val Val
1               5

<210> SEQ ID NO 244
<211> LENGTH: 9
<212> TYPE: PRT
<213> ORGANISM: Artificial
<220> FEATURE:
<223> OTHER INFORMATION: peptide

<400> SEQUENCE: 244

Met Leu Pro Gly Leu Leu Phe Ala Leu
1               5

```
<210> SEQ ID NO 245
<211> LENGTH: 9
<212> TYPE: PRT
<213> ORGANISM: Artificial
<220> FEATURE:
<223> OTHER INFORMATION: peptide

<400> SEQUENCE: 245

Met Leu Pro Gly Leu Leu Phe Gly Leu
1               5

<210> SEQ ID NO 246
<211> LENGTH: 9
<212> TYPE: PRT
<213> ORGANISM: Artificial
<220> FEATURE:
<223> OTHER INFORMATION: peptide

<400> SEQUENCE: 246

Met Leu Pro Gly Leu Leu Phe Lys Val
1               5

<210> SEQ ID NO 247
<211> LENGTH: 9
<212> TYPE: PRT
<213> ORGANISM: Artificial
<220> FEATURE:
<223> OTHER INFORMATION: peptide

<400> SEQUENCE: 247

Met Leu Pro Gly Leu Leu Phe Val Val
1               5

<210> SEQ ID NO 248
<211> LENGTH: 9
<212> TYPE: PRT
<213> ORGANISM: Artificial
<220> FEATURE:
<223> OTHER INFORMATION: peptide

<400> SEQUENCE: 248

Pro Leu Pro Gly Leu Leu Phe Ser Val
1               5

<210> SEQ ID NO 249
<211> LENGTH: 9
<212> TYPE: PRT
<213> ORGANISM: Artificial
<220> FEATURE:
<223> OTHER INFORMATION: peptide

<400> SEQUENCE: 249

Arg Met Pro Gly Leu Leu Phe Lys Val
1               5

<210> SEQ ID NO 250
<211> LENGTH: 9
<212> TYPE: PRT
<213> ORGANISM: Artificial
<220> FEATURE:
<223> OTHER INFORMATION: peptide

<400> SEQUENCE: 250

Ser Leu Pro Gly Leu Leu Phe Phe Leu
1               5

<210> SEQ ID NO 251
```

```
<211> LENGTH: 9
<212> TYPE: PRT
<213> ORGANISM: Artificial
<220> FEATURE:
<223> OTHER INFORMATION: peptide

<400> SEQUENCE: 251

Ser Leu Pro Gly Leu Leu Phe Thr Leu
1               5

<210> SEQ ID NO 252
<211> LENGTH: 9
<212> TYPE: PRT
<213> ORGANISM: Artificial
<220> FEATURE:
<223> OTHER INFORMATION: peptide

<400> SEQUENCE: 252

Ser Leu Pro Gly Leu Leu Phe Val Val
1               5

<210> SEQ ID NO 253
<211> LENGTH: 9
<212> TYPE: PRT
<213> ORGANISM: Artificial
<220> FEATURE:
<223> OTHER INFORMATION: peptide

<400> SEQUENCE: 253

Thr Leu Pro Gly Leu Leu Phe Pro Ala
1               5

<210> SEQ ID NO 254
<211> LENGTH: 9
<212> TYPE: PRT
<213> ORGANISM: Artificial
<220> FEATURE:
<223> OTHER INFORMATION: peptide

<400> SEQUENCE: 254

Thr Leu Pro Gly Leu Leu Phe Pro Val
1               5

<210> SEQ ID NO 255
<211> LENGTH: 9
<212> TYPE: PRT
<213> ORGANISM: Artificial
<220> FEATURE:
<223> OTHER INFORMATION: peptide

<400> SEQUENCE: 255

Val Leu Pro Gly Leu Leu Phe Gly Val
1               5

<210> SEQ ID NO 256
<211> LENGTH: 9
<212> TYPE: PRT
<213> ORGANISM: Artificial
<220> FEATURE:
<223> OTHER INFORMATION: peptide

<400> SEQUENCE: 256

Val Leu Pro Gly Leu Leu Phe Tyr Val
1               5

<210> SEQ ID NO 257
<211> LENGTH: 9
```

```
<212> TYPE: PRT
<213> ORGANISM: Artificial
<220> FEATURE:
<223> OTHER INFORMATION: peptide

<400> SEQUENCE: 257

Tyr Leu Pro Gly Leu Leu Phe Leu Met
1               5

<210> SEQ ID NO 258
<211> LENGTH: 9
<212> TYPE: PRT
<213> ORGANISM: Homo sapiens

<400> SEQUENCE: 258

Phe Leu Leu Phe Leu Thr Pro Met Glu
1               5

<210> SEQ ID NO 259
<211> LENGTH: 9
<212> TYPE: PRT
<213> ORGANISM: Homo sapiens

<400> SEQUENCE: 259

Lys Leu Ser Leu Gly Leu Pro Gly Leu
1               5

<210> SEQ ID NO 260
<211> LENGTH: 9
<212> TYPE: PRT
<213> ORGANISM: Homo sapiens

<400> SEQUENCE: 260

Ser Leu Val Gly Ile Leu His Leu Gln
1               5

<210> SEQ ID NO 261
<211> LENGTH: 9
<212> TYPE: PRT
<213> ORGANISM: Homo sapiens

<400> SEQUENCE: 261

Thr Leu Ala Tyr Leu Ile Phe Cys Leu
1               5

<210> SEQ ID NO 262
<211> LENGTH: 9
<212> TYPE: PRT
<213> ORGANISM: Homo sapiens

<400> SEQUENCE: 262

Gln Gln Met Gly Gly Phe Tyr Leu Cys
1               5

<210> SEQ ID NO 263
<211> LENGTH: 9
<212> TYPE: PRT
<213> ORGANISM: Homo sapiens

<400> SEQUENCE: 263

Ile Ala Leu Gly Gly Leu Leu Met Ile
1               5

<210> SEQ ID NO 264
<211> LENGTH: 9
```

```
<212> TYPE: PRT
<213> ORGANISM: Homo sapiens

<400> SEQUENCE: 264

Ile Met Asn Ser Leu Ser Leu Phe Ala
1               5

<210> SEQ ID NO 265
<211> LENGTH: 9
<212> TYPE: PRT
<213> ORGANISM: Homo sapiens

<400> SEQUENCE: 265

Leu Met Ile Pro Ala Gly Ile Tyr Ala
1               5

<210> SEQ ID NO 266
<211> LENGTH: 9
<212> TYPE: PRT
<213> ORGANISM: Homo sapiens

<400> SEQUENCE: 266

Ser Leu Phe Leu Gly Ile Leu Ser Val
1               5

<210> SEQ ID NO 267
<211> LENGTH: 9
<212> TYPE: PRT
<213> ORGANISM: Homo sapiens

<400> SEQUENCE: 267

Phe Leu Ser Asn Asp Thr Val Gln Leu
1               5

<210> SEQ ID NO 268
<211> LENGTH: 9
<212> TYPE: PRT
<213> ORGANISM: Homo sapiens

<400> SEQUENCE: 268

His Leu Leu Gly Pro Trp Leu Leu Leu
1               5

<210> SEQ ID NO 269
<211> LENGTH: 9
<212> TYPE: PRT
<213> ORGANISM: Homo sapiens

<400> SEQUENCE: 269

Ile Leu Ile Leu Ala Ile Cys Gly Leu
1               5

<210> SEQ ID NO 270
<211> LENGTH: 9
<212> TYPE: PRT
<213> ORGANISM: Homo sapiens

<400> SEQUENCE: 270

Trp Val Phe Glu His Pro Glu Thr Leu
1               5

<210> SEQ ID NO 271
<211> LENGTH: 9
<212> TYPE: PRT
<213> ORGANISM: Homo sapiens
```

<400> SEQUENCE: 271

Gly Leu Ala Phe Val Pro Leu Gln Ile
1               5

<210> SEQ ID NO 272
<211> LENGTH: 9
<212> TYPE: PRT
<213> ORGANISM: Homo sapiens

<400> SEQUENCE: 272

Gly Leu Tyr Phe Gly Met Leu Leu Leu
1               5

<210> SEQ ID NO 273
<211> LENGTH: 9
<212> TYPE: PRT
<213> ORGANISM: Homo sapiens

<400> SEQUENCE: 273

Ile Leu Ile Asp Lys Thr Ser Phe Val
1               5

<210> SEQ ID NO 274
<211> LENGTH: 9
<212> TYPE: PRT
<213> ORGANISM: Homo sapiens

<400> SEQUENCE: 274

Leu Leu Leu Leu Phe Ala Thr Gln Ile
1               5

<210> SEQ ID NO 275
<211> LENGTH: 9
<212> TYPE: PRT
<213> ORGANISM: Homo sapiens

<400> SEQUENCE: 275

Ser Ile Val Gly Ile Cys Leu Gly Val
1               5

<210> SEQ ID NO 276
<211> LENGTH: 9
<212> TYPE: PRT
<213> ORGANISM: Homo sapiens

<400> SEQUENCE: 276

Ser Ile Val Gly Ile Cys Leu Gly Val
1               5

<210> SEQ ID NO 277
<211> LENGTH: 9
<212> TYPE: PRT
<213> ORGANISM: Homo sapiens

<400> SEQUENCE: 277

Ala Leu Val Leu Ala Leu Val Leu Val
1               5

<210> SEQ ID NO 278
<211> LENGTH: 9
<212> TYPE: PRT
<213> ORGANISM: Homo sapiens

<400> SEQUENCE: 278

Gly Leu Ala Leu Val Leu Ala Leu Val
1               5

<210> SEQ ID NO 279
<211> LENGTH: 9
<212> TYPE: PRT
<213> ORGANISM: Homo sapiens

<400> SEQUENCE: 279

Leu Leu Phe Gly Ala Pro Ala Leu Leu
1               5

<210> SEQ ID NO 280
<211> LENGTH: 9
<212> TYPE: PRT
<213> ORGANISM: Homo sapiens

<400> SEQUENCE: 280

Pro Leu Pro Gly Leu Leu Phe Gly Ala
1               5

<210> SEQ ID NO 281
<211> LENGTH: 5
<212> TYPE: PRT
<213> ORGANISM: Homo sapiens

<400> SEQUENCE: 281

Leu Phe Leu Thr Pro
1               5

<210> SEQ ID NO 282
<211> LENGTH: 5
<212> TYPE: PRT
<213> ORGANISM: Homo sapiens

<400> SEQUENCE: 282

Ser Leu Gly Leu Pro
1               5

<210> SEQ ID NO 283
<211> LENGTH: 5
<212> TYPE: PRT
<213> ORGANISM: Homo sapiens

<400> SEQUENCE: 283

Val Gly Ile Leu His
1               5

<210> SEQ ID NO 284
<211> LENGTH: 5
<212> TYPE: PRT
<213> ORGANISM: Homo sapiens

<400> SEQUENCE: 284

Ala Tyr Leu Ile Phe
1               5

<210> SEQ ID NO 285
<211> LENGTH: 5
<212> TYPE: PRT
<213> ORGANISM: Homo sapiens

<400> SEQUENCE: 285

Met Gly Gly Phe Tyr

```
1               5

<210> SEQ ID NO 286
<211> LENGTH: 5
<212> TYPE: PRT
<213> ORGANISM: Homo sapiens

<400> SEQUENCE: 286

Leu Gly Gly Leu Leu
1               5

<210> SEQ ID NO 287
<211> LENGTH: 5
<212> TYPE: PRT
<213> ORGANISM: Homo sapiens

<400> SEQUENCE: 287

Asn Ser Leu Ser Leu
1               5

<210> SEQ ID NO 288
<211> LENGTH: 5
<212> TYPE: PRT
<213> ORGANISM: Homo sapiens

<400> SEQUENCE: 288

Ile Pro Ala Gly Ile
1               5

<210> SEQ ID NO 289
<211> LENGTH: 5
<212> TYPE: PRT
<213> ORGANISM: Homo sapiens

<400> SEQUENCE: 289

Phe Leu Gly Ile Leu
1               5

<210> SEQ ID NO 290
<211> LENGTH: 5
<212> TYPE: PRT
<213> ORGANISM: Homo sapiens

<400> SEQUENCE: 290

Ser Asn Asp Thr Val
1               5

<210> SEQ ID NO 291
<211> LENGTH: 5
<212> TYPE: PRT
<213> ORGANISM: Homo sapiens

<400> SEQUENCE: 291

Leu Gly Pro Trp Leu
1               5

<210> SEQ ID NO 292
<211> LENGTH: 5
<212> TYPE: PRT
<213> ORGANISM: Homo sapiens

<400> SEQUENCE: 292

Ile Leu Ala Ile Cys
1               5
```

```
<210> SEQ ID NO 293
<211> LENGTH: 5
<212> TYPE: PRT
<213> ORGANISM: Homo sapiens

<400> SEQUENCE: 293

Phe Glu His Pro Glu
1               5

<210> SEQ ID NO 294
<211> LENGTH: 5
<212> TYPE: PRT
<213> ORGANISM: Homo sapiens

<400> SEQUENCE: 294

Ala Phe Val Pro Leu
1               5

<210> SEQ ID NO 295
<211> LENGTH: 5
<212> TYPE: PRT
<213> ORGANISM: Homo sapiens

<400> SEQUENCE: 295

Tyr Phe Gly Met Leu
1               5

<210> SEQ ID NO 296
<211> LENGTH: 5
<212> TYPE: PRT
<213> ORGANISM: Homo sapiens

<400> SEQUENCE: 296

Ile Asp Lys Thr Ser
1               5

<210> SEQ ID NO 297
<211> LENGTH: 5
<212> TYPE: PRT
<213> ORGANISM: Homo sapiens

<400> SEQUENCE: 297

Leu Leu Phe Ala Thr
1               5

<210> SEQ ID NO 298
<211> LENGTH: 5
<212> TYPE: PRT
<213> ORGANISM: Homo sapiens

<400> SEQUENCE: 298

Val Gly Ile Cys Leu
1               5

<210> SEQ ID NO 299
<211> LENGTH: 5
<212> TYPE: PRT
<213> ORGANISM: Homo sapiens

<400> SEQUENCE: 299

Ile Lys Tyr Phe Leu
1               5

<210> SEQ ID NO 300
```

```
<211> LENGTH: 5
<212> TYPE: PRT
<213> ORGANISM: Homo sapiens

<400> SEQUENCE: 300

Val Leu Ala Leu Val
1               5

<210> SEQ ID NO 301
<211> LENGTH: 5
<212> TYPE: PRT
<213> ORGANISM: Homo sapiens

<400> SEQUENCE: 301

Ala Leu Val Leu Ala
1               5

<210> SEQ ID NO 302
<211> LENGTH: 5
<212> TYPE: PRT
<213> ORGANISM: Homo sapiens

<400> SEQUENCE: 302

Phe Gly Ala Pro Ala
1               5

<210> SEQ ID NO 303
<211> LENGTH: 5
<212> TYPE: PRT
<213> ORGANISM: Homo sapiens

<400> SEQUENCE: 303

Pro Gly Leu Leu Phe
1               5

<210> SEQ ID NO 304
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 304

Xaa Xaa Leu Phe Leu Thr Pro Xaa Xaa
1               5

<210> SEQ ID NO 305
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
```

```
<400> SEQUENCE: 305

Xaa Xaa Ser Leu Gly Leu Pro Xaa Xaa
1               5

<210> SEQ ID NO 306
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 306

Xaa Xaa Val Gly Ile Leu His Xaa Xaa
1               5

<210> SEQ ID NO 307
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 307

Xaa Xaa Ala Tyr Leu Ile Phe Xaa Xaa
1               5

<210> SEQ ID NO 308
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 308

Xaa Xaa Met Gly Gly Phe Tyr Xaa Xaa
1               5

<210> SEQ ID NO 309
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
```

```
<220> FEATURE:
<221> NAME/KEY: misc_feature
<222> LOCATION: (8)..(9)
<223> OTHER INFORMATION: Xaa can be any naturally occurring amino acid

<400> SEQUENCE: 309

Xaa Xaa Leu Gly Gly Leu Leu Xaa Xaa
1               5

<210> SEQ ID NO 310
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 310

Xaa Xaa Asn Ser Leu Ser Leu Xaa Xaa
1               5

<210> SEQ ID NO 311
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 311

Xaa Xaa Ile Pro Ala Gly Ile Xaa Xaa
1               5

<210> SEQ ID NO 312
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 312

Xaa Xaa Phe Leu Gly Ile Leu Xaa Xaa
1               5

<210> SEQ ID NO 313
<211> LENGTH: 9
<212> TYPE: PRT
<213> ORGANISM: Artificial
<220> FEATURE:
```

```
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 313

Xaa Xaa Ser Asn Asp Thr Val Xaa Xaa
1               5

<210> SEQ ID NO 314
<211> LENGTH: 9
<212> TYPE: PRT
<213> ORGANISM: Artificial
<220> FEATURE:
<223> OTHER INFORMATION: XXLGPWLXX
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 314

Xaa Xaa Leu Gly Pro Trp Leu Xaa Xaa
1               5

<210> SEQ ID NO 315
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 315

Xaa Xaa Ile Leu Ala Ile Cys Xaa Xaa
1               5

<210> SEQ ID NO 316
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 316

Xaa Xaa Phe Glu His Pro Glu Xaa Xaa
1               5
```

-continued

```
<210> SEQ ID NO 317
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 317

Xaa Xaa Ala Phe Val Pro Leu Xaa Xaa
1               5

<210> SEQ ID NO 318
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 318

Xaa Xaa Tyr Phe Gly Met Leu Xaa Xaa
1               5

<210> SEQ ID NO 319
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 319

Xaa Xaa Ile Asp Lys Thr Ser Xaa Xaa
1               5

<210> SEQ ID NO 320
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 320
```

```
Xaa Xaa Leu Leu Phe Ala Thr Xaa Xaa
1               5
```

<210> SEQ ID NO 321
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 321

```
Xaa Xaa Val Gly Ile Cys Leu Xaa Xaa
1               5
```

<210> SEQ ID NO 322
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 322

```
Xaa Xaa Ile Lys Tyr Phe Leu Xaa Xaa
1               5
```

<210> SEQ ID NO 323
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 323

```
Xaa Xaa Val Leu Ala Leu Val Xaa Xaa
1               5
```

<210> SEQ ID NO 324
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:

```
<221> NAME/KEY: misc_feature
<222> LOCATION: (8)..(9)
<223> OTHER INFORMATION: Xaa can be any naturally occurring amino acid

<400> SEQUENCE: 324

Xaa Xaa Ala Leu Val Leu Ala Xaa Xaa
1               5

<210> SEQ ID NO 325
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 325

Xaa Xaa Phe Gly Ala Pro Ala Xaa Xaa
1               5

<210> SEQ ID NO 326
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 326

Xaa Xaa Pro Gly Leu Leu Phe Xaa Xaa
1               5

<210> SEQ ID NO 327
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 327

Phe Leu Leu Phe Leu Thr Pro Xaa Leu
1               5

<210> SEQ ID NO 328
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (8)..(9)
<223> OTHER INFORMATION: Xaa can be any naturally occurring amino acid

<400> SEQUENCE: 328

Phe Xaa Leu Phe Leu Thr Pro Xaa Xaa
1               5

<210> SEQ ID NO 329
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 329

Gly Leu Leu Phe Leu Thr Pro Xaa Xaa
1               5

<210> SEQ ID NO 330
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 330

Thr Leu Leu Phe Leu Thr Pro Xaa Xaa
1               5

<210> SEQ ID NO 331
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 331

Xaa Leu Leu Phe Leu Thr Pro Leu Leu
1               5

<210> SEQ ID NO 332
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 332

Xaa Leu Leu Phe Leu Thr Pro Met Leu
1               5
```

```
<210> SEQ ID NO 333
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 333

Xaa Leu Leu Phe Leu Thr Pro Xaa Leu
1               5

<210> SEQ ID NO 334
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 334

Ala Leu Ser Leu Gly Leu Pro Xaa Leu
1               5

<210> SEQ ID NO 335
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 335

Ala Met Ser Leu Gly Leu Pro Xaa Leu
1               5

<210> SEQ ID NO 336
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 336

Phe Leu Ser Leu Gly Leu Pro Xaa Leu
1               5

<210> SEQ ID NO 337
<211> LENGTH: 9
<212> TYPE: PRT
<213> ORGANISM: Artificial
<220> FEATURE:
<223> OTHER INFORMATION: peptide
<220> FEATURE:
```

```
<221> NAME/KEY: misc_feature
<222> LOCATION: (8)..(8)
<223> OTHER INFORMATION: Xaa can be any naturally occurring amino acid

<400> SEQUENCE: 337

Leu Leu Ser Leu Gly Leu Pro Xaa Leu
1               5

<210> SEQ ID NO 338
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 338

Ser Leu Ser Leu Gly Leu Pro Xaa Leu
1               5

<210> SEQ ID NO 339
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 339

Val Leu Ser Leu Gly Leu Pro Xaa Xaa
1               5

<210> SEQ ID NO 340
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 340

Xaa Leu Ser Leu Gly Leu Pro Gly Leu
1               5

<210> SEQ ID NO 341
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 341

Xaa Leu Ser Leu Gly Leu Pro Ile Leu
1               5

<210> SEQ ID NO 342
```

```
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 342

Xaa Leu Ser Leu Gly Leu Pro Lys Leu
1               5

<210> SEQ ID NO 343
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 343

Xaa Leu Ser Leu Gly Leu Pro Xaa Leu
1               5

<210> SEQ ID NO 344
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 344

Xaa Leu Val Gly Ile Leu His Xaa Xaa
1               5

<210> SEQ ID NO 345
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 345

Phe Leu Ala Tyr Leu Ile Phe Xaa Leu
1               5

<210> SEQ ID NO 346
<211> LENGTH: 9
<212> TYPE: PRT
<213> ORGANISM: Artificial
```

```
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 346

Xaa Leu Ala Tyr Leu Ile Phe Xaa Leu
1               5

<210> SEQ ID NO 347
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 347

Ala Leu Leu Gly Gly Leu Leu Xaa Xaa
1               5

<210> SEQ ID NO 348
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 348

Ala Xaa Leu Gly Gly Leu Leu Leu Ile
1               5

<210> SEQ ID NO 349
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 349

Phe Xaa Leu Gly Gly Leu Leu Xaa Val
1               5

<210> SEQ ID NO 350
<211> LENGTH: 9
<212> TYPE: PRT
<213> ORGANISM: Artificial
<220> FEATURE:
<223> OTHER INFORMATION: peptide
<220> FEATURE:
```

```
<221> NAME/KEY: misc_feature
<222> LOCATION: (8)..(9)
<223> OTHER INFORMATION: Xaa can be any naturally occurring amino acid

<400> SEQUENCE: 350

Gly Met Leu Gly Gly Leu Leu Xaa Xaa
1               5

<210> SEQ ID NO 351
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 351

Xaa Leu Leu Gly Gly Leu Leu Xaa Ile
1               5

<210> SEQ ID NO 352
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 352

Ser Leu Leu Gly Gly Leu Leu Xaa Xaa
1               5

<210> SEQ ID NO 353
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 353

Ser Xaa Leu Gly Gly Leu Leu Leu Ile
1               5

<210> SEQ ID NO 354
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 354

Tyr Xaa Leu Gly Gly Leu Leu Met Val
```

```
1               5

<210> SEQ ID NO 355
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 355

Tyr Xaa Leu Gly Gly Leu Leu Xaa Val
1               5

<210> SEQ ID NO 356
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 356

Xaa Leu Leu Gly Gly Leu Leu Leu Ile
1               5

<210> SEQ ID NO 357
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 357

Xaa Met Leu Gly Gly Leu Leu Leu Ile
1               5

<210> SEQ ID NO 358
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 358

Xaa Xaa Leu Gly Gly Leu Leu Met Ile
1               5

<210> SEQ ID NO 359
<211> LENGTH: 9
<212> TYPE: PRT
<213> ORGANISM: Artificial
```

```
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 359

Xaa Xaa Leu Gly Gly Leu Leu Met Leu
1               5

<210> SEQ ID NO 360
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 360

Xaa Xaa Leu Gly Gly Leu Leu Met Val
1               5

<210> SEQ ID NO 361
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 361

Ile Leu Asn Ser Leu Ser Leu Xaa Xaa
1               5

<210> SEQ ID NO 362
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 362

Xaa Leu Asn Ser Leu Ser Leu Xaa Leu
1               5

<210> SEQ ID NO 363
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
```

```
<221> NAME/KEY: misc_feature
<222> LOCATION: (8)..(9)
<223> OTHER INFORMATION: Xaa can be any naturally occurring amino acid

<400> SEQUENCE: 363

Xaa Met Asn Ser Leu Ser Leu Xaa Xaa
1               5

<210> SEQ ID NO 364
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 364

Xaa Xaa Asn Ser Leu Ser Leu Xaa Ile
1               5

<210> SEQ ID NO 365
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 365

Leu Leu Ile Pro Ala Gly Ile Xaa Xaa
1               5

<210> SEQ ID NO 366
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 366

Met Xaa Ile Pro Ala Gly Ile Xaa Xaa
1               5

<210> SEQ ID NO 367
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
```

```
<220> FEATURE:
<221> NAME/KEY: misc_feature
<222> LOCATION: (8)..(8)
<223> OTHER INFORMATION: Xaa can be any naturally occurring amino acid

<400> SEQUENCE: 367

Xaa Leu Ile Pro Ala Gly Ile Xaa Leu
1               5

<210> SEQ ID NO 368
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 368

Xaa Met Ile Pro Ala Gly Ile Xaa Xaa
1               5

<210> SEQ ID NO 369
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 369

Xaa Xaa Ile Pro Ala Gly Ile Ala Val
1               5

<210> SEQ ID NO 370
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 370

Phe Leu Phe Leu Gly Ile Leu Xaa Leu
1               5

<210> SEQ ID NO 371
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 371
```

```
Tyr Leu Phe Leu Gly Ile Leu Xaa Leu
1               5
```

<210> SEQ ID NO 372
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 372

```
Tyr Leu Phe Leu Gly Ile Leu Xaa Xaa
1               5
```

<210> SEQ ID NO 373
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 373

```
Xaa Leu Phe Leu Gly Ile Leu Gly Leu
1               5
```

<210> SEQ ID NO 374
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 374

```
Xaa Leu Phe Leu Gly Ile Leu Ser Xaa
1               5
```

<210> SEQ ID NO 375
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 375

```
Phe Leu Ser Asn Asp Thr Val Xaa Leu
1               5
```

<210> SEQ ID NO 376
<211> LENGTH: 9
<212> TYPE: PRT

```
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 376

Phe Leu Ser Asn Asp Thr Val Xaa Xaa
1               5

<210> SEQ ID NO 377
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 377

Phe Xaa Ser Asn Asp Thr Val Xaa Xaa
1               5

<210> SEQ ID NO 378
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 378

Xaa Met Ser Asn Asp Thr Val Xaa Xaa
1               5

<210> SEQ ID NO 379
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 379

Xaa Leu Ser Asn Asp Thr Val Trp Leu
1               5

<210> SEQ ID NO 380
<211> LENGTH: 9
<212> TYPE: PRT
<213> ORGANISM: Artificial
<220> FEATURE:
<223> OTHER INFORMATION: peptide
```

```
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 380

Xaa Leu Ser Asn Asp Thr Val Xaa Leu
1               5

<210> SEQ ID NO 381
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 381

Xaa Leu Leu Gly Pro Trp Leu Xaa Leu
1               5

<210> SEQ ID NO 382
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 382

Xaa Leu Leu Gly Pro Trp Leu Xaa Val
1               5

<210> SEQ ID NO 383
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 383

Xaa Leu Leu Gly Pro Trp Leu Xaa Xaa
1               5

<210> SEQ ID NO 384
```

```
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 384

Ile Xaa Ile Leu Ala Ile Cys Xaa Val
1               5

<210> SEQ ID NO 385
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 385

Xaa Leu Ile Leu Ala Ile Cys Gly Val
1               5

<210> SEQ ID NO 386
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 386

Xaa Leu Ile Leu Ala Ile Cys Gly Xaa
1               5

<210> SEQ ID NO 387
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 387

Xaa Ile Phe Glu His Pro Glu Xaa Xaa
1               5
```

```
<210> SEQ ID NO 388
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 388

Xaa Xaa Phe Glu His Pro Glu Leu Leu
1               5

<210> SEQ ID NO 389
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 389

Xaa Xaa Phe Glu His Pro Glu Leu Xaa
1               5

<210> SEQ ID NO 390
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 390

Xaa Xaa Phe Glu His Pro Glu Xaa Xaa
1               5

<210> SEQ ID NO 391
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 391

Ala Leu Ala Phe Val Pro Leu Xaa Val
1               5

<210> SEQ ID NO 392
<211> LENGTH: 9
<212> TYPE: PRT
```

```
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 392

Phe Leu Ala Phe Val Pro Leu Xaa Leu
1               5

<210> SEQ ID NO 393
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 393

Phe Xaa Ala Phe Val Pro Leu Gln Leu
1               5

<210> SEQ ID NO 394
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 394

Ile Met Ala Phe Val Pro Leu Xaa Val
1               5

<210> SEQ ID NO 395
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 395

Leu Leu Ala Phe Val Pro Leu Xaa Leu
1               5

<210> SEQ ID NO 396
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 396

Leu Leu Ala Phe Val Pro Leu Xaa Xaa
```

```
1               5

<210> SEQ ID NO 397
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 397

Xaa Met Ala Phe Val Pro Leu Xaa Val
1               5

<210> SEQ ID NO 398
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 398

Xaa Met Ala Phe Val Pro Leu Xaa Leu
1               5

<210> SEQ ID NO 399
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 399

Xaa Leu Ala Phe Val Pro Leu Ala Val
1               5

<210> SEQ ID NO 400
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 400
```

```
Xaa Leu Ala Phe Val Pro Leu Xaa Val
1               5
```

<210> SEQ ID NO 401
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 401

```
Xaa Xaa Ala Phe Val Pro Leu Ala Val
1               5
```

<210> SEQ ID NO 402
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 402

```
Xaa Xaa Ala Phe Val Pro Leu Xaa Leu
1               5
```

<210> SEQ ID NO 403
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 403

```
Leu Leu Tyr Phe Gly Met Leu Xaa Leu
1               5
```

<210> SEQ ID NO 404
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 404

```
Xaa Leu Tyr Phe Gly Met Leu Xaa Leu
1               5
```

```
<210> SEQ ID NO 405
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 405

Xaa Leu Tyr Phe Gly Met Leu Xaa Xaa
1               5

<210> SEQ ID NO 406
<211> LENGTH: 10
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 406

Xaa Xaa Leu Tyr Phe Gly Met Leu Xaa Leu
1               5                   10

<210> SEQ ID NO 407
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 407

Ile Leu Ile Asp Lys Thr Ser Gly Xaa
1               5

<210> SEQ ID NO 408
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 408

Ile Xaa Ile Asp Lys Thr Ser Xaa Val
1               5
```

```
<210> SEQ ID NO 409
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 409

Val Leu Ile Asp Lys Thr Ser Xaa Xaa
1               5

<210> SEQ ID NO 410
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 410

Val Xaa Ile Asp Lys Thr Ser Ser Val
1               5

<210> SEQ ID NO 411
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 411

Tyr Leu Ile Asp Lys Thr Ser Xaa Xaa
1               5

<210> SEQ ID NO 412
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 412

Xaa Leu Ile Asp Lys Thr Ser Xaa Ala
1               5

<210> SEQ ID NO 413
<211> LENGTH: 9
<212> TYPE: PRT
<213> ORGANISM: Artificial
<220> FEATURE:
```

```
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 413

Xaa Leu Ile Asp Lys Thr Ser Xaa Val
1               5

<210> SEQ ID NO 414
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 414

Xaa Leu Ile Asp Lys Thr Ser Xaa Xaa
1               5

<210> SEQ ID NO 415
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 415

Phe Xaa Leu Leu Phe Ala Thr Xaa Val
1               5

<210> SEQ ID NO 416
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 416

Leu Leu Leu Leu Phe Ala Thr Xaa Val
1               5

<210> SEQ ID NO 417
<211> LENGTH: 9
<212> TYPE: PRT
<213> ORGANISM: Artificial
```

```
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 417

Leu Xaa Leu Leu Phe Ala Thr Xaa Val
1               5

<210> SEQ ID NO 418
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 418

Tyr Leu Leu Leu Phe Ala Thr Xaa Xaa
1               5

<210> SEQ ID NO 419
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 419

Xaa Xaa Leu Leu Phe Ala Thr Ser Val
1               5

<210> SEQ ID NO 420
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 420

Xaa Met Leu Leu Phe Ala Thr Xaa Xaa
1               5

<210> SEQ ID NO 421
<211> LENGTH: 9
<212> TYPE: PRT
<213> ORGANISM: Artificial
<220> FEATURE:
<223> OTHER INFORMATION: peptide
<220> FEATURE:
```

```
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 421

Xaa Xaa Val Gly Ile Cys Leu Xaa Val
1               5

<210> SEQ ID NO 422
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 422

Lys Leu Ile Lys Tyr Phe Leu Xaa Val
1               5

<210> SEQ ID NO 423
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 423

Xaa Leu Ile Lys Tyr Phe Leu Xaa Val
1               5

<210> SEQ ID NO 424
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 424

Xaa Leu Ile Lys Tyr Phe Leu Xaa Xaa
1               5

<210> SEQ ID NO 425
<211> LENGTH: 9
<212> TYPE: PRT
<213> ORGANISM: Artificial
<220> FEATURE:
<223> OTHER INFORMATION: peptide
```

```
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 425

Xaa Xaa Ile Lys Tyr Phe Leu Xaa Val
1               5

<210> SEQ ID NO 426
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 426

Ala Leu Val Leu Ala Leu Val Xaa Val
1               5

<210> SEQ ID NO 427
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 427

Ser Leu Val Leu Ala Leu Val Xaa Val
1               5

<210> SEQ ID NO 428
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 428

Xaa Leu Val Leu Ala Leu Val Xaa Val
1               5

<210> SEQ ID NO 429
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
```

```
<223> OTHER INFORMATION: Xaa can be any naturally occurring amino acid

<400> SEQUENCE: 429

Ala Leu Ala Leu Val Leu Ala Xaa Leu
1               5

<210> SEQ ID NO 430
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 430

Ala Leu Ala Leu Val Leu Ala Xaa Xaa
1               5

<210> SEQ ID NO 431
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 431

Phe Leu Ala Leu Val Leu Ala Ala Xaa
1               5

<210> SEQ ID NO 432
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 432

Phe Leu Ala Leu Val Leu Ala Xaa Leu
1               5

<210> SEQ ID NO 433
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 433

Gly Leu Ala Leu Val Leu Ala Xaa Ile
1               5

<210> SEQ ID NO 434
<211> LENGTH: 9
<212> TYPE: PRT
```

```
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 434

Gly Leu Ala Leu Val Leu Ala Xaa Leu
1               5

<210> SEQ ID NO 435
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 435

Gly Leu Ala Leu Val Leu Ala Xaa Val
1               5

<210> SEQ ID NO 436
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 436

Gly Xaa Ala Leu Val Leu Ala Val Val
1               5

<210> SEQ ID NO 437
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 437

Ser Leu Ala Leu Val Leu Ala Leu Xaa
1               5

<210> SEQ ID NO 438
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 438

Val Leu Ala Leu Val Leu Ala Glu Xaa
```

1               5

<210> SEQ ID NO 439
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 439

Val Leu Ala Leu Val Leu Ala Xaa Val
1               5

<210> SEQ ID NO 440
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 440

Tyr Leu Ala Leu Val Leu Ala Xaa Leu
1               5

<210> SEQ ID NO 441
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 441

Xaa Leu Ala Leu Val Leu Ala Glu Val
1               5

<210> SEQ ID NO 442
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 442

Xaa Leu Ala Leu Val Leu Ala Leu Leu
1               5

<210> SEQ ID NO 443
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature

```
<222> LOCATION: (1)..(1)
<223> OTHER INFORMATION: Xaa can be any naturally occurring amino acid

<400> SEQUENCE: 443

Xaa Leu Ala Leu Val Leu Ala Met Leu
1               5

<210> SEQ ID NO 444
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 444

Xaa Leu Ala Leu Val Leu Ala Xaa Leu
1               5

<210> SEQ ID NO 445
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 445

Xaa Leu Ala Leu Val Leu Ala Xaa Ile
1               5

<210> SEQ ID NO 446
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 446

Xaa Leu Ala Leu Val Leu Ala Xaa Val
1               5

<210> SEQ ID NO 447
<211> LENGTH: 9
<212> TYPE: PRT
<213> ORGANISM: Artificial
<220> FEATURE:
<223> OTHER INFORMATION: peptide
<220> FEATURE:
```

```
<221> NAME/KEY: misc_feature
<222> LOCATION: (8)..(9)
<223> OTHER INFORMATION: Xaa can be any naturally occurring amino acid

<400> SEQUENCE: 447

Ala Leu Phe Gly Ala Pro Ala Xaa Xaa
1               5

<210> SEQ ID NO 448
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 448

Leu Leu Phe Gly Ala Pro Ala Xaa Leu
1               5

<210> SEQ ID NO 449
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 449

Leu Leu Phe Gly Ala Pro Ala Gly Xaa
1               5

<210> SEQ ID NO 450
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 450

Leu Met Phe Gly Ala Pro Ala Xaa Val
1               5

<210> SEQ ID NO 451
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 451

Val Leu Phe Gly Ala Pro Ala Xaa Leu
1               5

<210> SEQ ID NO 452
```

```
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 452

Xaa Leu Phe Gly Ala Pro Ala Xaa Ala
1               5

<210> SEQ ID NO 453
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 453

Xaa Leu Phe Gly Ala Pro Ala Xaa Ile
1               5

<210> SEQ ID NO 454
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 454

Xaa Met Phe Gly Ala Pro Ala Xaa Val
1               5

<210> SEQ ID NO 455
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 455
```

```
Xaa Xaa Phe Gly Ala Pro Ala Xaa Val
1               5
```

<210> SEQ ID NO 456
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 456

```
Phe Xaa Pro Gly Leu Leu Phe Xaa Val
1               5
```

<210> SEQ ID NO 457
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 457

```
Ile Leu Pro Gly Leu Leu Phe Tyr Xaa
1               5
```

<210> SEQ ID NO 458
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 458

```
Ile Leu Pro Gly Leu Leu Phe Xaa Ile
1               5
```

<210> SEQ ID NO 459
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 459

```
Ile Leu Pro Gly Leu Leu Phe Xaa Leu
1               5
```

<210> SEQ ID NO 460
<211> LENGTH: 9
<212> TYPE: PRT

<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 460

Ile Met Pro Gly Leu Leu Phe Xaa Xaa
1               5

<210> SEQ ID NO 461
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 461

Lys Leu Pro Gly Leu Leu Phe Xaa Xaa
1               5

<210> SEQ ID NO 462
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 462

Leu Leu Pro Gly Leu Leu Phe Xaa Xaa
1               5

<210> SEQ ID NO 463
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 463

Met Leu Pro Gly Leu Leu Phe Xaa Xaa
1               5

<210> SEQ ID NO 464
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 464

Ser Leu Pro Gly Leu Leu Phe Xaa Xaa 1               5

<210> SEQ ID NO 465
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 465

Thr Leu Pro Gly Leu Leu Phe Pro Xaa
1               5

<210> SEQ ID NO 466
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 466

Val Leu Pro Gly Leu Leu Phe Xaa Val
1               5

<210> SEQ ID NO 467
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 467

Xaa Met Pro Gly Leu Leu Phe Xaa Xaa
1               5

<210> SEQ ID NO 468
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 468

Xaa Leu Pro Gly Leu Leu Phe Ser Val
1               5

<210> SEQ ID NO 469
<211> LENGTH: 9
<212> TYPE: PRT
<213> ORGANISM: Artificial

-continued

```
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 469

Xaa Leu Pro Gly Leu Leu Phe Val Val
1               5

<210> SEQ ID NO 470
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 470

Xaa Leu Pro Gly Leu Leu Phe Xaa Met
1               5

<210> SEQ ID NO 471
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 471

Xaa Leu Pro Gly Leu Leu Phe Xaa Leu
1               5

<210> SEQ ID NO 472
<211> LENGTH: 9
<212> TYPE: PRT
<213> ORGANISM: Artificial
<220> FEATURE:
<223> OTHER INFORMATION: peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 472

Xaa Leu Pro Gly Leu Leu Phe Xaa Val
1               5

<210> SEQ ID NO 473
<211> LENGTH: 20
<212> TYPE: PRT
```

```
<213> ORGANISM: Artificial
<220> FEATURE:
<223> OTHER INFORMATION: peptide

<400> SEQUENCE: 473

Met Ala Lys Thr Ile Ala Tyr Asp Glu Glu Ala Arg Arg Gly Leu Glu
1               5                   10                  15

Arg Gly Leu Asn
            20

<210> SEQ ID NO 474
<211> LENGTH: 13
<212> TYPE: PRT
<213> ORGANISM: Artificial
<220> FEATURE:
<223> OTHER INFORMATION: peptide

<400> SEQUENCE: 474

Thr Pro Pro Ala Tyr Arg Pro Pro Asn Ala Pro Ile Leu
1               5                   10

<210> SEQ ID NO 475
<211> LENGTH: 15
<212> TYPE: PRT
<213> ORGANISM: Artificial
<220> FEATURE:
<223> OTHER INFORMATION: peptide

<400> SEQUENCE: 475

Lys Ser Val Trp Ser Lys Leu Gln Ser Ile Gly Ile Arg Gln His
1               5                   10                  15

<210> SEQ ID NO 476
<211> LENGTH: 9
<212> TYPE: PRT
<213> ORGANISM: Artificial Sequence
<220> FEATURE:
<223> OTHER INFORMATION: peptide

<400> SEQUENCE: 476

Ala Met Asn Ser Leu Ser Leu Leu Leu
1               5

<210> SEQ ID NO 477
<211> LENGTH: 9
<212> TYPE: PRT
<213> ORGANISM: Artificial Sequence
<220> FEATURE:
<223> OTHER INFORMATION: peptide

<400> SEQUENCE: 477

Ala Met Asn Ser Leu Ser Leu Thr Val
1               5

<210> SEQ ID NO 478
<211> LENGTH: 9
<212> TYPE: PRT
<213> ORGANISM: Artificial Sequence
<220> FEATURE:
<223> OTHER INFORMATION: peptide

<400> SEQUENCE: 478

Gly Met Asn Ser Leu Ser Leu Leu Val
1               5

<210> SEQ ID NO 479
```

```
<211> LENGTH: 9
<212> TYPE: PRT
<213> ORGANISM: Artificial Sequence
<220> FEATURE:
<223> OTHER INFORMATION: peptide

<400> SEQUENCE: 479

Ile Leu Asn Ser Leu Ser Leu Asp Ile
1               5

<210> SEQ ID NO 480
<211> LENGTH: 9
<212> TYPE: PRT
<213> ORGANISM: Artificial Sequence
<220> FEATURE:
<223> OTHER INFORMATION: peptide

<400> SEQUENCE: 480

Ile Leu Asn Ser Leu Ser Leu Thr Ala
1               5

<210> SEQ ID NO 481
<211> LENGTH: 9
<212> TYPE: PRT
<213> ORGANISM: Artificial Sequence
<220> FEATURE:
<223> OTHER INFORMATION: peptide

<400> SEQUENCE: 481

Gln Met Asn Ser Leu Ser Leu Phe Leu
1               5

<210> SEQ ID NO 482
<211> LENGTH: 9
<212> TYPE: PRT
<213> ORGANISM: Artificial Sequence
<220> FEATURE:
<223> OTHER INFORMATION: peptide

<400> SEQUENCE: 482

Val Leu Asn Ser Leu Ser Leu Tyr Ala
1               5

<210> SEQ ID NO 483
<211> LENGTH: 9
<212> TYPE: PRT
<213> ORGANISM: Artificial Sequence
<220> FEATURE:
<223> OTHER INFORMATION: peptide

<400> SEQUENCE: 483

Val Met Asn Ser Leu Ser Leu Leu Ile
1               5

<210> SEQ ID NO 484
<211> LENGTH: 9
<212> TYPE: PRT
<213> ORGANISM: Artificial Sequence
<220> FEATURE:
<223> OTHER INFORMATION: peptide

<400> SEQUENCE: 484

Tyr Ile Asn Ser Leu Ser Leu Phe Ile
1               5

<210> SEQ ID NO 485
<211> LENGTH: 9
```

```
<212> TYPE: PRT
<213> ORGANISM: Artificial Sequence
<220> FEATURE:
<223> OTHER INFORMATION: peptide

<400> SEQUENCE: 485

Phe Leu Phe Glu His Pro Glu Thr Phe
1               5

<210> SEQ ID NO 486
<211> LENGTH: 9
<212> TYPE: PRT
<213> ORGANISM: Artificial Sequence
<220> FEATURE:
<223> OTHER INFORMATION: peptide

<400> SEQUENCE: 486

His Ile Phe Glu His Pro Glu His Leu
1               5

<210> SEQ ID NO 487
<211> LENGTH: 9
<212> TYPE: PRT
<213> ORGANISM: Artificial Sequence
<220> FEATURE:
<223> OTHER INFORMATION: peptide

<400> SEQUENCE: 487

Arg Val Phe Glu His Pro Glu Arg Val
1               5

<210> SEQ ID NO 488
<211> LENGTH: 9
<212> TYPE: PRT
<213> ORGANISM: Artificial Sequence
<220> FEATURE:
<223> OTHER INFORMATION: peptide

<400> SEQUENCE: 488

Tyr Thr Phe Glu His Pro Glu Thr Ile
1               5

<210> SEQ ID NO 489
<211> LENGTH: 9
<212> TYPE: PRT
<213> ORGANISM: Artificial Sequence
<220> FEATURE:
<223> OTHER INFORMATION: peptide

<400> SEQUENCE: 489

Ala Leu Ala Phe Val Pro Leu Trp Leu
1               5

<210> SEQ ID NO 490
<211> LENGTH: 9
<212> TYPE: PRT
<213> ORGANISM: Artificial Sequence
<220> FEATURE:
<223> OTHER INFORMATION: peptide

<400> SEQUENCE: 490

Ala Met Ala Phe Val Pro Leu Ala Leu
1               5

<210> SEQ ID NO 491
<211> LENGTH: 9
<212> TYPE: PRT
```

```
<213> ORGANISM: Artificial Sequence
<220> FEATURE:
<223> OTHER INFORMATION: peptide

<400> SEQUENCE: 491

Phe Leu Ala Phe Val Pro Leu Asp Val
1               5

<210> SEQ ID NO 492
<211> LENGTH: 9
<212> TYPE: PRT
<213> ORGANISM: Artificial Sequence
<220> FEATURE:
<223> OTHER INFORMATION: peptide

<400> SEQUENCE: 492

Leu Leu Ala Phe Val Pro Leu Pro Leu
1               5

<210> SEQ ID NO 493
<211> LENGTH: 9
<212> TYPE: PRT
<213> ORGANISM: Artificial Sequence
<220> FEATURE:
<223> OTHER INFORMATION: peptide

<400> SEQUENCE: 493

Val Leu Ala Phe Val Pro Leu Gly Val
1               5

<210> SEQ ID NO 494
<211> LENGTH: 9
<212> TYPE: PRT
<213> ORGANISM: Artificial Sequence
<220> FEATURE:
<223> OTHER INFORMATION: peptide

<400> SEQUENCE: 494

Ala Leu Phe Gly Ala Pro Ala Ala Ala
1               5

<210> SEQ ID NO 495
<211> LENGTH: 9
<212> TYPE: PRT
<213> ORGANISM: Artificial Sequence
<220> FEATURE:
<223> OTHER INFORMATION: peptide

<400> SEQUENCE: 495

Ile Leu Phe Gly Ala Pro Ala Gly Ala
1               5

<210> SEQ ID NO 496
<211> LENGTH: 9
<212> TYPE: PRT
<213> ORGANISM: Artificial Sequence
<220> FEATURE:
<223> OTHER INFORMATION: peptide

<400> SEQUENCE: 496

Asn Met Phe Gly Ala Pro Ala Gln Val
1               5

<210> SEQ ID NO 497
<211> LENGTH: 9
<212> TYPE: PRT
<213> ORGANISM: Artificial Sequence
```

```
<220> FEATURE:
<223> OTHER INFORMATION: peptide

<400> SEQUENCE: 497

Ser Leu Phe Gly Ala Pro Ala Thr Ala
1               5

<210> SEQ ID NO 498
<211> LENGTH: 9
<212> TYPE: PRT
<213> ORGANISM: Artificial Sequence
<220> FEATURE:
<223> OTHER INFORMATION: peptide

<400> SEQUENCE: 498

Thr Leu Phe Gly Ala Pro Ala Ala Ala
1               5

<210> SEQ ID NO 499
<211> LENGTH: 9
<212> TYPE: PRT
<213> ORGANISM: Artificial Sequence
<220> FEATURE:
<223> OTHER INFORMATION: peptide

<400> SEQUENCE: 499

Val Ile Phe Gly Ala Pro Ala Leu Val
1               5

<210> SEQ ID NO 500
<211> LENGTH: 9
<212> TYPE: PRT
<213> ORGANISM: Artificial Sequence
<220> FEATURE:
<223> OTHER INFORMATION: peptide

<400> SEQUENCE: 500

Val Leu Phe Gly Ala Pro Ala Gly Ile
1               5

<210> SEQ ID NO 501
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 501

Ala Met Asn Ser Leu Ser Leu Xaa Xaa
1               5

<210> SEQ ID NO 502
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
```

```
<400> SEQUENCE: 502

Xaa Met Asn Ser Leu Ser Leu Leu Xaa
1               5

<210> SEQ ID NO 503
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 503

Xaa Met Asn Ser Leu Ser Leu Xaa Ile
1               5

<210> SEQ ID NO 504
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 504

Xaa Met Asn Ser Leu Ser Leu Xaa Leu
1               5

<210> SEQ ID NO 505
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid

<400> SEQUENCE: 505

Tyr Xaa Phe Glu His Pro Glu Thr Xaa
1               5

<210> SEQ ID NO 506
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (9)..(9)
```

```
<223> OTHER INFORMATION: Xaa can be any naturally occurring amino acid

<400> SEQUENCE: 506

Ala Leu Phe Gly Ala Pro Ala Ala Xaa
1               5

<210> SEQ ID NO 507
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 507

Val Leu Phe Gly Ala Pro Ala Xaa Xaa
1               5

<210> SEQ ID NO 508
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 508

Xaa Leu Phe Gly Ala Pro Ala Ala Ala
1               5

<210> SEQ ID NO 509
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 509

Xaa Met Phe Gly Ala Pro Ala Leu Val
1               5
```

ANTIGENIC PEPTIDES FOR TREATMENT OF B-CELL MALIGNANCY

This application is a continuation of International Patent Application No. PCT/EP2020/082101 which has an international filing date of 13 Nov. 2020 and claims foreign priority to International Patent Application No. PCT/EP2020/079257 filed on 16 Oct. 2020 and European Patent Application No. 19306475.5 filed on 15 Nov. 2019. Each patent application recited above is hereby incorporated by reference in its entirety.

This application contains references to amino acid sequences and/or nucleic acid sequences as an ASC II text file. The name of the ASC II text file is "EB01P016WO1UST1_sequencelisting_ST25". It was created on 3 Jun. 2022 and is 111 KB. The aforementioned sequence listing is hereby incorporated by reference in its entirety pursuant to 37 C.F.R. § 1.52(e).

The present invention relates to the field of cancer therapy, more particularly by immunotherapeutic methods. In particular, the present invention provides various peptides, which are useful in cancer immunotherapy, especially for preventing and treating B-cell malignancy.

Amongst all B-cell malignancies, such as B-cell lymphomas, non-Hodgkin's lymphoma (NHL) is the seventh leading cause of new cancer cases and accounts for approximately 3% of cancer-related deaths in the United States. Among all NHLs, diffuse large B-cell lymphoma (DLBCL) is the most common lymphoma subtype comprising 32.5% of all newly diagnosed cases, followed by follicular lymphoma (FL) with 17.1%, and mantle-cell lymphoma (MCL) representing 3-5%. Over 25,000 new cases of DLBCL are diagnosed annually in the United States, representing an incidence rate of 6.9 per 100,000. Addition of the anti-CD20 monoclonal antibody, namely rituximab, to the standard chemotherapy, R-CHOP, resulted in significant improvement in complete response (CR) rates, event-free (EFS) and overall (OS) survival in DLBCL. Unfortunately, approximately 30-40% of cases relapse or progress after R-CHOP. There are specific subgroups of patients who will have poor responses and outcomes to standard R-CHOP such as MYC-rearranged DLBCL, high-grade B-cell lymphomas with MYC, BCL2 or BCL rearrangements, activated B-cell (ABC) DLBCL that could benefit from novel approaches (Chavez et al., CAR T-cell therapy for B-cell lymphomas: clinical trial results of available products; Ther Adv Hematol. 2019).

Amongst new approaches, chimeric antigen receptor (CAR) T-cells, such as CD19-targeted CAR T-cells, represent the new standard of care for patients with DLBCL that are refractory to at least two prior lines of therapy. Two CAR T-cell products [axicabtagene ciloleucel (axi-cel) (KTE-019) and tisagenlecleucel (CTL019) have obtained US Food and Drug Administration approval for the treatment of refractory DLBCL after two lines of therapy. While this represents a significant addition to the treatment armamentarium of DLBCL, approximately 50% of cases will continue to succumb to their disease. As a result, future research must focus on identifying disease-, treatment- or patient-related factors that can help successfully predict treatment outcomes.

Tumor antigen-based vaccination thus represents a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Human cancer regression antigens. Curr Opin Immunol. 2013 April; 25(2):284-90), and neo-antigens, resulting from point mutations of cellular proteins. However, most of the tumor-associated antigens (TAAs) and tumor-specific antigens (TSAs) are (existing) human proteins and are, thus, considered as self-antigens. During thymic selection process, T cells that recognize peptide/self MHC complexes with sufficient affinity are clonally depleted. By offering a protection against auto-immune disease, this mechanism of T cell repertoire selection also reduce the possibility to develop immunity against TAAs and TSAs. This is exemplified by the fact that cancer-reactive TCRs are generally of weak affinity. Furthermore, until now, most of the vaccine trials performed with selected TAAs and TSAs with high binding affinity for MHC have not been shown to elicit strong immunity, probably reflecting the consequence of thymic selection. A potent anti-tumoral response will thus depend on the presentation of immunoreactive peptides and the presence of a sufficient number of reactive cells "trained" to recognize these antigens. There is thus a need in the art to identify alternative antigenic peptides, which can overcome the limitations encountered in this field.

The invention has for objective to meet the aforementioned needs. This object is achieved by means of the subject-matter set out below, in particular in the items provided by the present invention and in the appended claims.

The invention is described in more detail below.

Definitions

Unless otherwise defined herein, scientific and technical terms used in the present application shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as Owen et al. (Kuby Immunology, 7$^{th}$, edition, 2013—W. H. Freeman) and Sambrook et al. (Molecular cloning: A laboratory manual 4th edition, Cold Spring Harbor Laboratory Press—Cold Spring Harbor, N.Y., USA, 2012).

Nevertheless, with respect to the use of different terms throughout the current specification, the following definitions more particularly apply.

The terms "peptide", "polypeptide", "protein" and variations of these terms refer to peptides, oligopeptides, polypeptides, or proteins comprising at least two amino acids joined to each other preferably by a normal peptide bond, or, alternatively, by a modified peptide bond, such as for example in the cases of isosteric peptides. The term "(poly) peptide" refers to a peptide and/or to a polypeptide. In particular, the terms "peptide", "polypeptide" and "protein" refer to a sequential chain of amino acids of any length linked together via peptide bonds (—NHCO—). Peptides, polypeptides and proteins can play a structural and/or functional role in a cell in vitro and/or in vivo. The terms "peptide", "polypeptide", "protein" preferably encompass amino acids chains in size ranging from 2 to at least about 1000 amino acid residues. The term "peptide" preferably encompasses herein amino acid chains in size of less than about 30 amino acids, while the terms "polypeptide" and "protein" preferably encompass amino acid chains in size of at least 30 amino acids. The terms "polypeptide" and "protein" are used herein interchangeably. In a preferred embodiment, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In a preferred embodiment, a (poly)peptide or protein is a "classical" (poly)peptide or protein, whereby a "classical" (poly)peptide or protein is typically composed of amino acids selected from the 20 amino acids defined by the genetic code, linked to each other by a normal peptide bond.

As well-known in the art, peptides, polypeptides and proteins can be encoded by nucleic acids. The terms "nucleic acid", "nucleic acid molecule", "nucleic acid sequence", "polynucleotide", "nucleotide sequence" are used herein interchangeable and refer to a precise succession of natural nucleotides (e.g., A, T, G, C and U), or synthetic nucleotides, i.e. to a chain of at least two nucleotides. In particular, the terms "nucleic acid", "nucleic acid molecule", "nucleic acid sequence", "polynucleotide", "nucleotide sequence" refer to DNA or RNA. Nucleic acids preferably comprise single stranded, double stranded or partially double stranded DNA or RNA, preferably selected from genomic DNA (gDNA), complementary DNA (cDNA), ribosomal DNA (rDNA), and the transcription product of said DNA, such as RNA. Preferred examples of nucleic acids include ribosomal RNA (rRNA), messenger RNA (mRNA); antisense DNA, antisense RNA; complementary RNA and/or DNA sequences, ribozyme, (complementary) RNA/DNA sequences with or without expression elements, a vector; a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a transfer RNA (tRNA), or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof. It is within the skill of the person in the art to determine nucleotide sequences which can encode a specific amino acid sequence.

The (poly)peptides and/or nucleic acids according to the invention may be prepared by any known method in the art including, but not limited to, any synthetic method, any recombinant method, any ex vivo generation method and the like, and any combination thereof. Such techniques are fully explained in the literature as mentioned above.

The term "antigenic peptide" as used herein refers to a peptide, which is prone to induce/elicit, increase, prolong or maintain an immune response in a subject to whom it is administered. In particular, the antigenic peptide is a sequence variant of (a fragment/epitope of) a (human) tumor antigen. In other words, the antigenic peptide is preferably distinct from (a fragment/epitope of) a (human) tumor antigen, but it has preferably amino acid similarity with (a fragment/epitope of) the (human) tumor antigen. Importantly, the antigenic peptide shares the same core sequence with the respective (fragment/epitope of) a (human) tumor antigen. Preferably, the immune response induced/elicited, increased, prolonged or maintained by the antigenic peptide (also) targets the respective (fragment/epitope of) a (human) tumor antigen.

As used herein, the term "tumor antigen" comprises tumor-specific antigens (TSAs) and tumor-associated antigens (TAAs). In general, the term "tumor antigen" or "tumor protein" designates herein an antigenic substance produced in tumor cells, and sometimes also in normal cells, and which can trigger an immune response upon administration in a subject. In humans, those have been classified according to their expression pattern, function or genetic origin, and include without limitation, overexpressed self-antigens (such as BIRC5); cancer-testis (CT) antigens (such as MAGE-1); mutational antigens, also known as neo-antigens (such as mutants from p53); tissue-specific differentiation antigens (such as the melanoma antigens Melan A/MART-1); viral antigens which are expressed by oncoviruses (such as HPV, EBV); oncofetal antigens (such as alpha-fetoprotein AFP and carcinoembryonic antigen CEA); and universal antigens (telomerase).

The term "B-cell tumor antigen", as used herein, refers to an antigen associated with and/or involved in the etiology of the B-cell malignancy, e.g. is involved in or expressed in the B-cell malignancy. In other words, the antigen is expressed by or on B cells, including human B cells, such as any of a number of known B cell marker. Preferably, the B-cell tumor antigen is highly expressed (overexpressed) in B-cell lymphomas such as CD19, CD20, CD22, CD37 or TNFRSF13C. An antigenic peptide "derived from" a B-cell tumor antigen usually shares the same core sequence as an epitope (the "reference epitope") of said B-cell tumor antigen.

The term "core sequence", as used herein, refers to the amino acids in the middle of the sequence (also referred as the "central amino acids" of the sequence), e.g. in the middle of an antigenic peptide and/or a (reference) epitope. Accordingly, the core sequence consists of all amino acids except the two most N-terminal and the two most C-terminal amino acids. For example, in a peptide of nine amino acids (e.g. an antigenic peptide according to the present invention or the respective (fragment/epitope of) a (human) tumor antigen), the five middle amino acids represent the core sequence and alterations may only occur at any of the two N-terminal and the two C-terminal amino acid positions. Accordingly, a "shared core sequence" (or a "maintained" core sequence) usually means that mutations/differences are allowed only in the two most N-terminal and in the two most C-terminal amino acids of the (reference) epitope/sequence.

The term "prevalence", as used herein, refers to the cumulative frequency of each protein of the human microbiota wherein the core sequence shared with the respective (fragment/epitope of) a (human) tumor antigen is found and present in an antigenic peptide. Indeed, a core sequence of interest may be present in one or several distinct antigenic peptides, each of such antigenic peptides may be present in one or distinct proteins expressed in the human microbiota. Accordingly, a global prevalence of a core sequence is derived from the frequency of each protein of the human microbiota wherein the core sequence shared with the respective (fragment/epitope of) a (human) tumor antigen) is found and by considering the frequencies of each protein of the human microbiota where similar peptides (i.e. distinct antigenic peptides) sharing the same core sequence were found.

The term "microbiota", as used herein, refers to commensal microorganisms found in and on all multicellular organisms studied to date from plants to animals. In particular, microbiota have been found to be crucial for immunologic, hormonal and metabolic homeostasis of their host. Microbiota include bacteria, archaea, protists, fungi and viruses. Accordingly, a "microbiota sequence variant" (or "microbiota variant") is a sequence variant of a (human) reference sequence (in particular an epitope/a fragment of a human tumor antigen), which occurs in microbiota, such as bacteria (e.g., it may be contained in a microbiota protein, such as a bacterial protein). Preferably, the antigenic peptide of the invention is a microbiota sequence variant (of a reference epitope/fragment of a human B-cell tumor antigen). Accordingly, the antigenic peptide is preferably present (e.g. comprised in) in at least one protein expressed by the human microbiota.

A "sequence variant" typically shares, in particular over the whole length of the sequence, at least 50% sequence identity with a reference sequence, namely, a fragment/epitope of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment/epitope of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. The microbiota sequence variant is preferably selected from the group consisting of bacterial sequence variants, archaea sequence variants, protist sequence variants, fungi sequence variants and viral sequence variants. More preferably, the microbiota sequence variant is a bacterial sequence variant.

Anatomically, microbiota reside on or within any of a number of tissues and biofluids, including the skin, conjunctiva, mammary glands, vagina, placenta, seminal fluid, uterus, ovarian follicles, lung, saliva, oral cavity (in particular oral mucosa), and the gastrointestinal tract, in particular the gut. In the context of the present invention the microbiota sequence variant is preferably a sequence variant of microbiota of the gastrointestinal tract (microorganisms residing in the gastrointestinal tract), more preferably a sequence variant of microbiota of the gut (microorganisms residing in the gut). Accordingly, it is most preferred that the microbiota sequence variant is a (human) gut bacterial sequence variant (i.e. a sequence variant of bacteria residing in the (human) gut).

While microbiota can be found in and on many multicellular organisms (all multicellular organisms studied to date from plants to animals), microbiota found in and on human are preferred. Such microbiota are referred to herein as "human microbiota" (wherein the term human refers specifically to the localization/residence of the microbiota). Within the context of the present invention, the microbiota sequence variant is a human microbiota sequence variant.

The term "immunogenic compound" refers to a compound comprising an antigenic peptide according to the present invention. An "immunogenic compound" is able to induce/elicit, increase, prolong or maintain an immune response against said antigenic peptide in a subject to whom it is administered. In some embodiments, immunogenic compounds comprise at least one antigenic peptide, or alternatively at least one compound comprising such an antigenic peptide, linked to a protein, such as a carrier protein.

A "carrier protein" is usually a protein, which is able to transport a cargo, such as the antigenic peptide according to the present invention. For example, the carrier protein may transport its cargo across a membrane. In the context of the present invention, a carrier protein in particular (also) encompasses a peptide or a polypeptide that is able to elicit an immune response against the antigenic peptide that is linked thereto. Carrier proteins are known in the art.

Alternatively, such carrier peptide or polypeptide may be co-administered in the form of immune adjuvant.

Preferably, the antigenic peptide as described herein may be co-administered or linked, for example by covalent or non-covalent bond, to a protein/peptide having immunoadjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be distinct from the antigenic peptide according to the present invention. Preferably, the adjuvant peptide/protein is capable of recalling immune memory or provides a non-specific help or could be a specific helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. The HHD-DR3 peptide of sequence MAKTIAYDEEARRGLERGLN (SEQ ID NO: 473). This peptide represents another example of a helper peptide (having immuno-adjuvant properties), which is preferred in the context of the present invention. Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred helper peptides include the UCP2 peptide (for example as described in WO 2013/135553 A1 or in Dosset M, Godet Y, Vauchy C, Beziaud L, Lone Y C, Sedlik C, Liard C, Levionnois E, Clerc B, Sandoval F, Daguindau E, Wain-Hobson S, Tartour E, Langlade-Demoyen P, Borg C, Adotévi O: Universal cancer peptide-based therapeutic vaccine breaks tolerance against telomerase and eradicates established tumor. Clin Cancer Res. 2012 Nov. 15; 18(22): 6284-95. doi: 10.1158/1078-0432.CCR-12-0896. Epub 2012 Oct. 2) and the BIRC5 peptide (for example as described in EP2119726 A1 or in Widenmeyer M, Griesemann H, Stevanović S, Feyerabend S, Klein R, Attig S, Hennenlotter J, Wernet D, Kuprash D V, Sazykin A Y, Pascolo S, Stenzl A, Gouttefangeas C, Rammensee H G: Promiscuous survivin peptide induces robust CD4+ T-cell responses in the majority of vaccinated cancer patients. Int J Cancer. 2012 Jul. 1; 131(1):140-9. doi: 10.1002/ijc.26365. Epub 2011 Sep. 14). The most preferred helper peptide is the UCP2 peptide (amino acid sequence: KSVWSKLQSIGIRQH; SEQ ID NO: 475, for example as described in WO 2013/135553 A1 or in Dosset et al., Clin Cancer Res. 2012 Nov. 15; 18(22):6284-95. In particular, the antigenic peptide as described herein, or a polypeptide comprising the said antigenic peptide, may be linked, for example by covalent or non-covalent bond, to the helper peptide.

As used herein, the term "immunogenic composition" refers to a composition that is able to elicit, induce, increase, prolong or maintain an immune response, in particular which elicits, induces, increases, prolongs or maintains an immune response, when it is administered to a mammal, and especially when it is administered to a human individual. Preferably, an immunogenic composition further comprises one or more immuno-adjuvant substances.

By "pharmaceutically acceptable excipient or carrier", it is meant herein a compound of pharmaceutical grade which improves the delivery, stability or bioavailability of an active agent, and can be metabolized by, and is non-toxic to, a subject to whom it is administered. Preferred excipients and carriers according to the invention include any of the excipients or carriers commonly used in pharmaceutical products, such as, for example, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable excipients or carriers may further comprise minor amounts of auxiliary substances such as wetting or emulsifying agents, or preservatives.

By "vaccine", it is meant herein a composition capable of stimulating the immune system of a living organism so that protection against a harmful antigen is provided, either through prophylaxis or through therapy. Prophylactic vaccines are preferred. Preferably, a vaccine or a vaccine composition further comprises one or more immuno-adjuvant substances.

According to the different aspects and embodiments of the invention described herein, a "subject" or "host" preferably refers to a mammal, and most preferably to a human being. Said subject may have, been suspected of having, or be at risk of developing B-cell malignancy.

The term "B cell malignancy" refers to diseases associated with transformation of B cells. It encompasses, among others, B-cell lymphomas, acute lymphocytic (or lymphoblastic) leukemia (ALL), chronic lymphocytic leukemia (CLL, Richter's). In the context of the present invention, B-cell lymphomas are preferred such as non-Hodgkin lymphoma (NHL). For instance, NHL is selected from the group consisting of indolent (slow-growing) NHL, aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

As used herein, the terms "preventing", "prevention", "prophylaxis" or "prevent" generally mean to avoid or minimize the onset or development of a disease or condition before its onset, while the terms "treating, "treatment" or "treat" encompass reducing, ameliorating or curing a disease or condition (or symptoms of a disease or condition) after its onset. The term "preventing" encompasses "reducing the likelihood of occurrence of" or "reducing the likelihood of reoccurrence".

An "effective amount" or "effective dose" as used herein is an amount which provides the desired effect. For therapeutic purposes, an effective amount is an amount sufficient to provide a beneficial or desired clinical result. The preferred effective amount for a given application can be easily determined by the skilled person taking into consideration, for example, the size, age, weight of the subject, the type of disease/disorder to be prevented or treated, and the amount of time since the disease/disorder began. In the context of the present invention, in terms of prevention or treatment, an effective amount of the composition is an amount that is sufficient to induce a humoral and/or cell-mediated immune response directed against the disease/disorder.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Additional definitions are provided throughout the specification.

The present invention may be understood more readily by reference to the following detailed description, including preferred embodiments of the invention, and examples included herein.

DETAILED DESCRIPTION

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Antigenic Peptides According to the Present Invention

In a first aspect, the present invention provides an antigenic peptide derived from a tumor antigen, especially a B-cell tumor antigen, wherein the antigenic peptide shares the same core sequence with the reference epitope of a tumor antigen, and wherein the shared core sequence has a high prevalence in the human microbiota.

The present invention also provides an antigenic peptide comprising or consisting of an amino acid sequence as set forth in any one of SEQ ID NOs 316, 304-315, 317-472, and 501-509. Preferably, the antigenic peptide may comprise or consist of an amino acid sequence as set forth in any one of SEQ ID NOs 316, 304-315 and 317-326.

Furthermore, the present invention provides an antigenic peptide comprising or consisting of an amino acid sequence as set forth in any one of SEQ ID NOs 1-257 and 476-500, wherein, optionally, one or two amino acid residues may be substituted, deleted or added. Preferably, the core sequence (of SEQ ID NOs 1-257 and 476-500) is maintained, if one or two amino acid residues are substituted, deleted or added. More preferably, the antigenic peptide comprises or consists of an amino acid sequence as set forth in any one of SEQ ID NOs 1-257 and 476-500 (without mutations). Amino acid sequences according to SEQ ID NOs 1-257 and 476-500 are microbiota sequence variants (microbiota variants, in particular bacterial sequence variants) of human tumor epitopes, in particular of reference epitopes/fragments of human B-cell tumor antigens. In other words, amino acid sequences according to SEQ ID NOs 1-257 and 476-500 can be found in bacterial proteins and show sequence similarity to reference epitopes/fragments of human B-cell tumor antigens, as illustrated in detail in Table 1A.

The present inventors have identified a set of antigenic peptides that can be used to induce a specific immune response against tumor cells. Those antigenic peptides are distinct from, but have amino acid similarity to, (fragments of) human tumor antigens, especially tumor antigens highly expressed in B-cell lymphomas such as CD19, CD20, CD22, CD37 or TNFRSF13C, as shown in Table 1A, Table 1B and Table 1C. Importantly, the antigenic peptides according to the present invention have a core sequence identical with the core sequence of the sequence of the epitope (fragment) of the reference tumor antigen. Moreover, the core sequence displays a high prevalence based on the frequency of the proteins present in the human microbiota where the core sequence is found.

In particular, the antigenic peptides according to the present invention are comprised in polypeptides and proteins produced by commensal bacteria from the human gut. Accordingly, the antigenic peptides according to the present invention are not human sequences, but bacterial sequences. Without wishing to be bound by any particular theory, the inventors believe that the human immune repertoire contains T-cell clones that are reactive against bacterial peptides (comprised in proteins produced by commensal bacteria from the gut), which have amino acid similarity to fragments of human tumor antigens. In particular, the antigenic peptides according to the present invention can elicit a stronger immune response than the corresponding human peptides, since T cells able to recognize strictly human peptides have been depleted as recognizing self-antigens during maturation, which is not the case for the antigenic peptides according to the present invention. This may explain why the antigenic peptides described herein are able to induce an immune response, and especially a T-cell response, when these peptides are administered to a (human) individual.

Accordingly, without being bound to any theory the inventors assume that proteins produced by commensal bacteria from the gut are able to "mimic" tumor antigens, and can be used for triggering a specific immune response against tumor cells. These findings provide further evidence that commensal bacteria may contribute to tumor cells eradication.

The antigenic peptides disclosed herein can be prepared using well known techniques. For example, the peptides can be prepared synthetically, by recombinant DNA technology or chemical synthesis. Peptides disclosed herein can be synthesized individually or as longer polypeptides comprising two or more peptides (e.g., two or more peptides or a peptide and a non-peptide). The antigenic peptides can be isolated i.e., purified to be substantially free of other naturally occurring host cell proteins and fragments thereof, e.g., at least about 70%, 80% or 90% purified. Preferably, the antigenic peptides according to the present invention are isolated antigenic peptides.

Therefore, the core sequence represents a major feature of the antigenic peptides according to the present invention. The inventors have thus identified core sequences of highly interest with high prevalence since they are present in several sequence variants of a fragment of a (reference) tumor antigen and/or in several human microbiota proteins with high frequency in a significant portion of the general human population. The inventors have selected the antigenic peptides of the invention liable to trigger the best cross-reactive tumor-specific cytotoxic T cell immune response in order to prevent and treat B-cell malignancy.

In general, the shared core sequence has a high prevalence in the human microbiota, when the prevalence is higher than 30%, preferably higher than 40%, preferably higher than 50%, more preferably higher than 60%, even more preferably higher than 70%, still more preferably higher than 80%, particularly preferably higher than 90%, and most preferably higher than 95%.

The prevalence of a core sequence is derived from the frequency of each protein of the human microbiota wherein the core sequence shared with the respective (fragment/epitope of) a (human) tumor antigen) is found and by considering the frequencies of each protein of the human microbiota where similar peptides (i.e. distinct antigenic peptides) sharing the same core sequence were found. For example, to assess whether a core sequence has high prevalence, the frequency of each protein present in the human microbiota wherein said core sequence is found is calculated from a microbiota sequence database. The prevalence is then derived from the cumulative frequency calculated for each protein of the human microbiota where the core sequence of interest is found and present in an antigenic peptide. Such database may preferably comprise microbiota (sequence) data of multiple individuals (subjects). An example of such a database is the "Integrated reference catalog of the human gut microbiome" (version 1.0, March 2014; Li et al. Meta-HIT Consortium. An integrated catalog of reference genes in the human gut microbiome. Nat Biotechnol. 2014 August; 32(8):834-41 URL: http://meta.genomics.cn/meta/home), which includes data from the major human microbiome profiling efforts, the American National Institutes of Health Human Microbiome Project (NIH-HMP) and the European Metagenomics of the Human Intestinal Tract Initiative (MetaHIT).

Accordingly, the invention relates to antigenic peptides having amino acid similarity with a tumor antigen since they are derived from this tumor antigen (or tumor epitope). The expression "having amino acid similarity with a tumor antigen" as used herein, refers in particular to a sequence variant of fragments of a (reference) human tumor antigen, such as CD22 or the other exemplified human tumor antigens described below in Tables 1A, 1B and 1C. A "sequence variant" typically shares, in particular over the whole length of the sequence, at least 50% sequence identity with a reference sequence, namely, a fragment of a (reference) tumor antigen. Preferably, the sequence variant shares at least 55%, preferably at least 60%, preferably 66%, preferably at least 70%, preferably at least 77%, more preferably at least 80%, even more preferably at least 88%, still more preferably at least 90% sequence identity with the reference sequence, namely, a fragment of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. In particular, an amino acid sequence variant has an altered sequence in which one or more of the amino acids in the reference sequence is mutated, e.g. deleted or substituted, or one or more amino acids are inserted into the sequence of the reference amino acid sequence. For example, variant sequences which are at least 90% identical have no more than 10 alterations, i.e. any combination of deletions, insertions or substitutions, per 100 amino acids of the reference sequence.

Methods for comparing the identity (similarity) of two or more sequences are well known in the art. The percentage to which two sequences are identical can, e.g., be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U. S. A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may also be used to determine the % identity between two polynucleotides and the % identity between two (poly)peptide sequences. BESTFIT uses the "local homology" algorithm of Smith and Waterman (1981), J. Mol. Biol. 147, 195-197 and finds the best single region of similarity between two sequences.

In general, the antigenic peptide according to the present invention binds to MHC class I (major histocompatibility complex class I, MHC I) molecules.

MHC class I molecules present epitopes to killer T cells, also called cytotoxic T lymphocytes (CTLs). A CTL expresses CD8 receptors, in addition to TCRs (T-cell receptors). When a CTL's CD8 receptor docks to a MHC class I molecule, if the CTL's TCR fits the epitope within the MHC class I molecule, the CTL triggers the cell to undergo programmed cell death by apoptosis. This route is particularly useful in prevention and/or treatment of cancer, since cancer cells are directly attacked. In humans, MHC class I comprises HLA-A, HLA-B, and HLA-C molecules. Typically, peptides (epitopes) having a length of 8-10, amino acids are presented by MHC I.

In general, the antigenic peptide according to the present invention may be of any length. Preferably, the length of the antigenic peptide according to the present invention does not exceed 350 amino acids. For example, the maximum length of the antigenic peptide according to the present invention may be 300 or 250 amino acids. More preferably, the maximum length of the antigenic peptide according to the present invention does not exceed 200 amino acids, e.g., not more than 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14 or 13 amino acids. In particular, the length of the antigenic peptides according to the present invention is preferably at most 30 or 25 amino acids, more preferably at most 20 or 15 amino acids, even more preferably at most 10 amino acids. Particularly preferably, the antigenic peptide according to the present invention comprises at least 8 or 9 amino acids, such as 10 amino acids. Still more preferably, the antigenic peptide has a length of 9 or 10 amino acids. In particular, the antigenic peptides are not the full-length proteins produced by human microbiota (from which the antigenic peptides may be derived from). In other words, the antigenic peptide of the invention is preferably a fragment of a full-length protein (produced by human microbiota).

Similarly, the "fragment/epitope" of the (reference) tumor antigen, which typically serves as reference sequence, preferably comprises consecutive 9 amino acids of the tumor antigen and eventually 10 amino acids. It is understood that the "fragment/epitope" of the (reference) tumor antigen is not the full-length tumor antigen (protein).

A "fragment" (of a protein or nucleic acid (sequence)), as used herein, has preferably a maximum length of 95%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2% or 1% of the full-length (reference) protein/nucleic acid/sequence. In some embodiments, the length of the fragment does not exceed 50% of the length of the (full-length) (reference) protein/nucleic acid. In other embodiments, the length of the fragment of the (reference) protein/nucleic acid does not exceed 20% or 10% of the length of the (full-length) (reference) protein/nucleic acid.

In more general, the present invention provides an antigenic peptide, which comprises or consists of a sequence variant of a fragment/epitope of a human (reference) tumor antigen, especially a microbiota sequence variant of a fragment/epitope of a human tumor antigen. The human tumor antigen may be selected from the group consisting of CD19, CD20, CD22, CD37 and TNFRSF13C. The fragment/epitope of the human (reference) tumor antigen may be selected from the group consisting of any one of SEQ ID 258-280.

Preferably, the antigenic peptide comprises or consists of a microbiota variant of a human reference peptide according to any one of SEQ ID NOs 258-280. In particular, SEQ ID NOs 258-280 refer to human tumor epitopes, in particular reference epitopes/fragments of human B-cell tumor antigens. Examples of microbiota variants of human reference peptides according to any one of SEQ ID NOs 258-280 are peptides according to SEQ ID NOs 1-257 and 476-500 (as illustrated in Table 1A below). Preferred microbiota sequence variants (microbiota variants) are bacterial sequence variants. In other words, amino acid sequences according to SEQ ID NOs 1-257 and 476-500 can be found in bacterial proteins and show sequence similarity to reference epitopes/fragments of human B-cell tumor antigens, as illustrated in detail in Table 1A. More preferably, the antigenic peptide comprises or consists of a microbiota variant of a human reference peptide according to any one of SEQ ID NOs 258, 260-266, 270, 271, 279 and 280. Even more preferably, the antigenic peptide comprises or consists of a microbiota variant of a human reference peptide according to any one of SEQ ID NOs 260, 264, 270, 271, 279 and 280. Still more preferably, the antigenic peptide comprises or consists of a microbiota variant of a human reference peptide according to any one of SEQ ID NOs 264, 270, 271 and 279.

Accordingly, the present invention also provides an antigenic peptide comprising or consisting of a microbiota variant of a human reference peptide according to any one of SEQ ID NOs 258-280; preferably according to any one of SEQ ID NOs 258, 260-266, 270, 271, 279 and 280; more preferably according to any one of SEQ ID NOs 260, 264, 270, 271, 279 and 280; even more preferably according to any one of SEQ ID NOs 264, 270, 271 and 279.

In a particular embodiment, the present invention provides an antigenic peptide derived from CD19, CD20, CD22, CD37 or TNFRSF13C, wherein the antigenic peptide shares the same core sequence with a fragment/epitope of a (reference) tumor antigen; and wherein the shared core sequence has a high prevalence in the human microbiota. Such prevalence is derived from the frequency of the at least one protein present in the human microbiota wherein said core sequence is found. Preferably, the antigenic peptide according to the invention comprises or consists of any one of SEQ ID Nos 304-326 (MHC I Consensus Sequences).

In one embodiment, the antigenic peptide binds moderately, strongly or very strongly to MHC class I (major histocompatibility complex class I, MHC I) molecules.

Binding of the at least one antigenic peptide to MHC class I (major histocompatibility complex class I) molecules, may be tested by the MHC I in silico or in vitro binding tests as described herein. Accordingly, strong and very strong binders may be selected as described above. Preferably, binding to MHC I is tested (in silico and/or in vitro as described herein) for the at least one antigenic peptide to MHC I molecules and, additionally, for the (respective reference) tumor antigen (the fragment/epitope of a (reference) tumor antigen) to MHC I molecules, and binding affinities are preferably obtained for both (the fragment/epitope of tumor antigen and the antigenic peptide).

After the binding test, preferably only such antigenic peptides are selected, which bind moderately, strongly or very strongly to MHC I. More preferably only strong and very strong binders are selected and most preferably, only such antigenic peptides are selected, which bind very strongly to MHC I. More preferably, only such antigenic peptides are selected, which bind strongly or very strongly to MHC I molecule, and wherein the epitope/fragment of a (reference) tumor antigen (the "corresponding" tumor antigenic epitope sequence) binds weaker (e.g. weakly or moderately) to MHC I molecule. Even more preferably, only such microbiota sequence variants are selected, which bind very strongly to MHC I, and wherein the epitope/fragment of a (reference) tumor antigen binds weakly MHC I.

Accordingly, the antigenic peptide of the invention binds preferably stronger (i.e., has a higher binding affinity) to an MHC I molecule than the respective human reference epitope of the B-cell tumor antigen (which shares the same core sequence). In other words, the reference epitope of the human B-cell tumor antigen, which shares the same core sequence, binds preferably weaker to MHC I molecules (i.e., has lower binding affinity) than the respective antigenic peptide.

Prediction of MHC class I binding (MHC in silico binding test) may be performed using publicly available tools, such as "NetMHCpan", for example the "NetMHCpan 3.0 Server" or the "NetMHCpan 4.0 Server" (Center for biological sequence analysis, Technical University of Denmark DTU; URL: http://www.cbs.dtu.dk/services/NetMHCpan/). The NetMHCpan method, in particular NetMHCpan 3.0 or a higher version, is trained on more than 180000 quantitative binding data covering 172 MHC molecules from human (HLA-A, B, C, E) and other species. In general, the affinity may be predicted by leaving default thresholds for strong and weak binders. For example, for HLA-A*0201 a calculated affinity below 50 nM may indicate "strong binders", and an affinity between 50 and 300 nM may indicate "moderate binders". In NetMHCpan, for example in NetMHCpan 3.0 or in NetMHCpan 4.0, the rank of the predicted affinity may be compared to a set of 400000 random natural peptides, which may be used as a measure of the % rank binding affinity. This value is not affected by inherent bias of certain molecules towards higher or lower mean predicted affinities. For example (e.g., for HLA-A*0201), very strong binders may be defined as having % rank<0.5, strong binders may be defined as having % rank<1.0, moderate binders may be defined as having % rank from 1.0 to 2.0, and weak binders may be defined as having a % rank>2.0. A method for in vitro testing is well-known to the skilled person. For example, the skilled person may use the experimental protocol as validated for peptides presented by HLA-A*0201 in Tourdot et al., A general strategy to enhance immunogenicity of low-affinity HLA-A2.1—associated peptides: implication in the identification of cryptic tumor epitopes. Eur J Immunol. 2000 December; 30(12):3411-21. In this context, a reference peptide, such as HIV pol 589-597, may be additionally used in the test. This enables calculation of the in vitro affinity relative to the binding observed with the reference peptide, e.g. by the following equation: Relative affinity—concentration of each peptide inducing 20% of expression of HLA-A*0201/concentration of the reference peptide inducing 20% of expression of HLA-A*0201 (where 100% is the level of HLA-A*0201 expression detected with the reference peptide, e.g. HIV pol 589-597, for example used at a 100 μM concentration). For example, a peptide displaying a relative affinity below 1 may be considered as a "strong binder", a peptide displaying relative affinity between 1 and 2 may be considered as a "moderate binder" and a peptide displaying relative affinity more than 3 may be considered as a "weak binder".

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, HLA-A*24 and HLA-B*07 are examples of different MHC class I alleles that can be expressed from these loci. For instance, the antigenic peptide according to the invention may bind to HLA-A*01, HLA-A*02, HLA-A*24 and HLA-B*07 molecules. In particular, the antigenic peptide according to the invention binds to HLA-A*02.

In one embodiment, the antigenic peptide according to the invention is a microbiota sequence variant of an epitope of a human tumor antigen.

In particular, the microbiota sequence variant of an epitope of a human tumor antigen is identified in at least one protein expressed in the human microbiota. Preferably, the at least one protein present in the human microbiota is secreted or comprises a transmembrane domain.

Cellular localization, in particular whether a protein is secreted or comprises a transmembrane domain, can be tested in silico or in vitro by methods well-known to the skilled person. For example, "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

For example, to test whether a protein is secreted, presence of a signal peptide may be assessed. Signal peptides are ubiquitous protein-sorting signals that target their passenger (cargo) protein for translocation across the cytoplasmic membrane in prokaryotes. To test presence of a signal peptide, for example "SignalP 4.1 Server" (Center for biological sequence analysis, Technical University of Denmark DTU; URL: www.cbs.dtu.dk/services/SignalP) and/or "Phobius" (A combined transmembrane topology and signal peptide predictor, Stockholm Bioinformatics Centre; URL: phobius.sbc.su.se) may be used. Preferably, two prediction tools (e.g., SignalP 4.1 Server and Phobius) may be combined.

Moreover, it may be determined whether a protein comprises a transmembrane domain. Both, signal peptides and transmembrane domains are hydrophobic, but transmembrane helices typically have longer hydrophobic regions. For example, SignalP 4.1 Server and Phobius have the capacity to differentiate signal peptides from transmembrane domains. Preferably, a minimum number of two predicted transmembrane helices is set to differentiate between membrane and cytoplasmic proteins to deliver the final consensus list.

In one embodiment, the microbiota sequence variant of a fragment/epitope of a human tumor antigen is presented in its entirety after the cleavage of the bacterial protein expressed in the human microbiota. In this context, the term "cleavage" refers to the processing of the peptide for MHC presentation, in particular to MHC-I processing. For example, cleavage prediction score and/or affinity can be used to predict antigenic cleavage for proper MHC binding (for presentation to CD8 T cells). Such "cleavage probability score" may be calculated with software (preferably such score is higher than 70%, preferably higher than 80%, more preferably higher than 90%). For example, "IEDB" (Immune Epitope Database and Analysis Resource, IEDB Analysis Resource, supported by a contract from the National Institute of Allergy and Infectious Diseases, a component of the National Institutes of Health in the Department of Health and Human Services), which provides, for example, MHC-I processing predictions (URL: http://tools.iedb.org/mhcnp/) may be used. In another example, NetChops (The role of the proteasome in generating cytotoxic T cell epitopes: Insights obtained from improved predictions of proteasomal cleavage. M. Nielsen, C. Lundegaard, O. Lund, and C. Kesmir. Immunogenetics., 57(1-2):33-41, 2005; Prediction of proteasome cleavage motifs by neural networks. C. Kesmir, A. Nussbaum, Hansjorg Schild, Vincent Detours, and S. Brunak, Prot. Eng., 15(4): 287-296, 2002; URL: http://www.cbs.dtu.dk/services/NetChop/) may be used for cleavage prediction. This algorithm is based on a neural network trained on experimental data on proteasome cleavage in vitro and known HLA ligands. The output of the network was a score between 0.0 and 1.0. A random predictor would score 0.5 and a perfect predictor would score 1. Accordingly, a high score for a peptide (e.g. above 0.7, preferably above 0.8, more preferably above 0.9, as described above) suggests that it is effectively cleaved at its N- and/or C-terminus (and not its center), while a low score is associated with peptides cleaved in their center. Thereby, information regarding proteasomal cleavage, TAP transport, and MHC class 1 analysis tools can be combined for prediction of peptide presentation.

In one embodiment, the antigenic peptide induces T-cell cross-reactivity against the human epitope of a (reference) tumor antigen. T-cell cross-reactivity is a phenomenon of the immune system defined as the recognition of two or more peptide-MHC complexes (pMHCs) by the T-cell receptor (TCR).

Epitope mimicry relates to the concept of sequence and structure similarity between foreign antigens and self-antigens as a trigger mechanism to elicit a cross reactive immune response against the self-antigens. Interestingly, such epitope mimicry offers a possible way to bypass the repertoire restriction of human T cells due to clonal depletion of T cells recognizing self-antigens.

In particular, antigens (i.e. the antigenic peptides according to the present invention) distinct from self-antigens (e.g. human epitope of a tumor antigen), but sharing sequence similarity with the self-antigen, (i) can still be recognized due to the cross-reactivity of the T-cell receptor and (ii) it is expected that such antigens are recognized by T cell/TCR that have not been depleted during T cell education process. Accordingly, such antigens are able to elicit a strong immune response leading to clonal expansion of T cell harboring potential cross reactivity with self-antigens.

T cell receptor cross-reactivity with the epitope of a human (reference) tumor antigen may be measured as shown in the section EXAMPLES by ELISPOT-IFNγ assay. Briefly HLA-A2 transgenic mice (e.g. HHD DR1 mice expressing human HLA-A2 and HLA-DR1 MHC and lacking the murine H-2 class I and class II MHCs and/or HHD DR3 mice expressing human HLA-A2 and HLA-DRs MHC) are immunized on day 0 (do) with a prime injection, and on d14 with a boost injection with an antigenic peptide of the present invention and the epitope of a human (reference) tumor antigen. Seven days after the boost injection (i.e. on d21), the mice are euthanized and splenocytes are stimulated in vitro with the antigenic peptide of the present invention to assess their capacity to secrete IFN-gamma as assessed by ELISPOT.

In particular, the present invention provides an antigenic peptide, which is a microbiota sequence variant of a fragment/epitope of a human tumor antigen, wherein the epitope of a human tumor antigen may comprise or consist of any one of SEQ ID Nos 1-257 and 476-500.

Table 1A below provides an overview over the antigenic peptides according to the present inventions with their amino acid sequences and SEQ ID NOs and with the corresponding fragment/epitope of a human tumor antigen (also referred to herein as "human reference peptide"). Table 1A also provides information to which tumor antigen each antigenic peptide according to the present invention relates. SEQ ID NOs 1 to 257 and 476-500 refer to HLA-A*02 antigenic peptides according to the present invention.

TABLE 1A

HLA-A02 Antigenic peptides according to the invention.

| Tumor antigen | Sequence human reference peptide | SEQ ID NO. human reference peptide | Sequence antigenic peptide | SEQ ID NO. antigenic peptide |
| --- | --- | --- | --- | --- |
| CD19 | FLLFLTPME | 258 | FLLFLTPIL | 1 |
| CD19 | FLLFLTPME | 258 | FLLFLTPLL | 2 |
| CD19 | FLLFLTPME | 258 | FMLFLTPRI | 3 |
| CD19 | FLLFLTPME | 258 | GLLFLTPLA | 4 |
| CD19 | FLLFLTPME | 258 | GLLFLTPLL | 5 |
| CD19 | FLLFLTPME | 258 | GLLFLTPLM | 6 |
| CD19 | FLLFLTPME | 258 | ILLFLTPLL | 7 |
| CD19 | FLLFLTPME | 258 | SLLFLTPLL | 8 |
| CD19 | FLLFLTPME | 258 | TLLFLTPLI | 9 |
| CD19 | FLLFLTPME | 258 | TLLFLTPML | 10 |
| CD19 | FLLFLTPME | 258 | VLLFLTPML | 11 |
| CD19 | FLLFLTPME | 258 | YLLFLTPVL | 12 |
| CD19 | KLSLGLPGL | 259 | ALSLGLPGL | 13 |
| CD19 | KLSLGLPGL | 259 | ALSLGLPLL | 14 |
| CD19 | KLSLGLPGL | 259 | ALSLGLPML | 15 |
| CD19 | KLSLGLPGL | 259 | ALSLGLPQL | 16 |
| CD19 | KLSLGLPGL | 259 | ALSLGLPRL | 17 |
| CD19 | KLSLGLPGL | 259 | AMSLGLPCL | 18 |
| CD19 | KLSLGLPGL | 259 | AMSLGLPML | 19 |
| CD19 | KLSLGLPGL | 259 | FLSLGLPIL | 20 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD19 | KLSLGLPGL | 259 | FLSLGLPKL | 21 |
| CD19 | KLSLGLPGL | 259 | ILSLGLPIL | 22 |
| CD19 | KLSLGLPGL | 259 | KLSLGLPVL | 23 |
| CD19 | KLSLGLPGL | 259 | LLSLGLPFL | 24 |
| CD19 | KLSLGLPGL | 259 | LLSLGLPGL | 25 |
| CD19 | KLSLGLPGL | 259 | MLSLGLPIL | 26 |
| CD19 | KLSLGLPGL | 259 | RLSLGLPGL | 27 |
| CD19 | KLSLGLPGL | 259 | SLSLGLPIL | 28 |
| CD19 | KLSLGLPGL | 259 | SLSLGLPKL | 29 |
| CD19 | KLSLGLPGL | 259 | VLSLGLPLL | 30 |
| CD19 | KLSLGLPGL | 259 | VLSLGLPTA | 31 |
| CD19 | KLSLGLPGL | 259 | VLSLGLPTV | 32 |
| CD19 | KLSLGLPGL | 259 | YLSLGLPIL | 33 |
| CD19 | SLVGILHLQ | 260 | LLVGILHLV | 34 |
| CD19 | SLVGILHLQ | 260 | SLVGILHII | 35 |
| CD19 | TLAYLIFCL | 261 | FLAYLIFGL | 36 |
| CD19 | TLAYLIFCL | 261 | FLAYLIFTL | 37 |
| CD19 | TLAYLIFCL | 261 | RLAYLIFLL | 38 |
| CD19 | TLAYLIFCL | 261 | YLAYLIFEL | 39 |
| CD19 | QQMGGFYLC | 262 | LQMGGFYLL | 40 |
| CD20 | IALGGLLMI | 263 | AILGGLLLI | 41 |
| CD20 | IALGGLLMI | 263 | ALLGGLLLI | 42 |
| CD20 | IALGGLLMI | 263 | ALLGGLLML | 43 |
| CD20 | IALGGLLMI | 263 | FALGGLLTV | 44 |
| CD20 | IALGGLLMI | 263 | FLLGGLLLI | 45 |
| CD20 | IALGGLLMI | 263 | FLLGGLLMV | 46 |
| CD20 | IALGGLLMI | 263 | GMLGGLLLI | 47 |
| CD20 | IALGGLLMI | 263 | GMLGGLLML | 48 |
| CD20 | IALGGLLMI | 263 | HILGGLLMV | 49 |
| CD20 | IALGGLLMI | 263 | IILGGLLVV | 50 |
| CD20 | IALGGLLMI | 263 | ILLGGLLLI | 51 |
| CD20 | IALGGLLMI | 263 | LLLGGLLLI | 52 |
| CD20 | IALGGLLMI | 263 | LLLGGLLMI | 53 |
| CD20 | IALGGLLMI | 263 | NLLGGLLLI | 54 |
| CD20 | IALGGLLMI | 263 | SILGGLLLI | 55 |
| CD20 | IALGGLLMI | 263 | SLLGGLLLI | 56 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD20 | IALGGLLMI | 263 | SLLGGLLML | 57 |
| CD20 | IALGGLLMI | 263 | SMLGGLLLI | 58 |
| CD20 | IALGGLLMI | 263 | TLLGGLLMI | 59 |
| CD20 | IALGGLLMI | 263 | YALGGLLEV | 60 |
| CD20 | IALGGLLMI | 263 | YILGGLLMV | 61 |
| CD20 | IALGGLLMI | 263 | YMLGGLLLI | 62 |
| CD20 | IALGGLLMI | 263 | YVLGGLLMI | 63 |
| CD20 | IALGGLLMI | 263 | YVLGGLLMV | 64 |
| CD20 | IMNSLSLFA | 264 | AMNSLSLLL | 476 |
| CD20 | IMNSLSLFA | 264 | AMNSLSLTV | 477 |
| CD20 | IMNSLSLFA | 264 | AMNSLSLYI | 65 |
| CD20 | IMNSLSLFA | 264 | GMNSLSLLV | 478 |
| CD20 | IMNSLSLFA | 264 | ILNSLSLDI | 479 |
| CD20 | IMNSLSLFA | 264 | ILNSLSLKI | 66 |
| CD20 | IMNSLSLFA | 264 | ILNSLSLKL | 67 |
| CD20 | IMNSLSLFA | 264 | ILNSLSLLL | 68 |
| CD20 | IMNSLSLFA | 264 | ILNSLSLTA | 480 |
| CD20 | IMNSLSLFA | 264 | LLNSLSLFL | 69 |
| CD20 | IMNSLSLFA | 264 | QMNSLSLFL | 481 |
| CD20 | IMNSLSLFA | 264 | VLNSLSLYA | 482 |
| CD20 | IMNSLSLFA | 264 | VMNSLSLLI | 483 |
| CD20 | IMNSLSLFA | 264 | YINSLSLFI | 484 |
| CD20 | IMNSLSLFA | 264 | YMNSLSLAL | 70 |
| CD20 | LMIPAGIYA | 265 | FLIPAGIFL | 71 |
| CD20 | LMIPAGIYA | 265 | ILIPAGIYL | 72 |
| CD20 | LMIPAGIYA | 265 | LLIPAGIAV | 73 |
| CD20 | LMIPAGIYA | 265 | LLIPAGIEL | 74 |
| CD20 | LMIPAGIYA | 265 | LLIPAGIGL | 75 |
| CD20 | LMIPAGIYA | 265 | LLIPAGILI | 76 |
| CD20 | LMIPAGIYA | 265 | LLIPAGILL | 77 |
| CD20 | LMIPAGIYA | 265 | MLIPAGIPA | 78 |
| CD20 | LMIPAGIYA | 265 | MMIPAGIAV | 79 |
| CD20 | LMIPAGIYA | 265 | VMIPAGIFL | 80 |
| CD20 | SLFLGILSV | 266 | FLFLGILGL | 81 |
| CD20 | SLFLGILSV | 266 | FLFLGILPL | 82 |
| CD20 | SLFLGILSV | 266 | MLFLGILSV | 83 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD20 | SLFLGILSV | 266 | YLFLGILGI | 84 |
| CD20 | SLFLGILSV | 266 | YLFLGILGL | 85 |
| CD20 | SLFLGILSV | 266 | YLFLGILSL | 86 |
| CD20 | SLFLGILSV | 266 | YLFLGILYL | 87 |
| CD22 | FLSNDTVQL | 267 | FLSNDTVLL | 88 |
| CD22 | FLSNDTVQL | 267 | FLSNDTVPL | 89 |
| CD22 | FLSNDTVQL | 267 | FLSNDTVSA | 90 |
| CD22 | FLSNDTVQL | 267 | FMSNDTVKV | 91 |
| CD22 | FLSNDTVQL | 267 | ILSNDTVWL | 92 |
| CD22 | FLSNDTVQL | 267 | KMSNDTVVL | 93 |
| CD22 | FLSNDTVQL | 267 | RLSNDTVGL | 94 |
| CD22 | FLSNDTVQL | 267 | RMSNDTVEI | 95 |
| CD22 | FLSNDTVQL | 267 | TLSNDTVWL | 96 |
| CD22 | HLLGPWLLL | 268 | ALLGPWLIV | 97 |
| CD22 | HLLGPWLLL | 268 | FLLGPWLCL | 98 |
| CD22 | HLLGPWLLL | 268 | KLLGPWLSV | 99 |
| CD22 | HLLGPWLLL | 268 | LLLGPWLLL | 100 |
| CD22 | HLLGPWLLL | 268 | YLLGPWLLV | 101 |
| CD22 | ILILAICGL | 269 | ILILAICGV | 102 |
| CD22 | ILILAICGL | 269 | IMILAICLV | 103 |
| CD22 | ILILAICGL | 269 | RLILAICGL | 104 |
| CD22 | ILILAICGL | 269 | YLILAICGV | 105 |
| CD22 | WVFEHPETL | 270 | FLFEHPETF | 485 |
| CD22 | WVFEHPETL | 270 | HIFEHPEHL | 486 |
| CD22 | WVFEHPETL | 270 | KIFEHPELL | 106 |
| CD22 | WVFEHPETL | 270 | LIFEHPERV | 107 |
| CD22 | WVFEHPETL | 270 | RVFEHPELV | 108 |
| CD22 | WVFEHPETL | 270 | RVFEHPERV | 487 |
| CD22 | WVFEHPETL | 270 | YTFEHPETI | 488 |
| CD22 | WVFEHPETL | 270 | YVFEHPELL | 109 |
| CD22 | WVFEHPETL | 270 | YIFEHPETA | 110 |
| CD37 | GLAFVPLQI | 271 | ALAFVPLAV | 111 |
| CD37 | GLAFVPLQI | 271 | ALAFVPLSV | 112 |
| CD37 | GLAFVPLQI | 271 | ALAFVPLWL | 489 |
| CD37 | GLAFVPLQI | 271 | AMAFVPLAL | 490 |
| CD37 | GLAFVPLQI | 271 | FLAFVPLDV | 491 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| CD37 | GLAFVPLQI | 271 | FLAFVPLIL | 113 |
| CD37 | GLAFVPLQI | 271 | FLAFVPLQL | 114 |
| CD37 | GLAFVPLQI | 271 | FLAFVPLVL | 115 |
| CD37 | GLAFVPLQI | 271 | FMAFVPLQL | 116 |
| CD37 | GLAFVPLQI | 271 | GMAFVPLLL | 117 |
| CD37 | GLAFVPLQI | 271 | HLAFVPLLV | 118 |
| CD37 | GLAFVPLQI | 271 | ILAFVPLYL | 119 |
| CD37 | GLAFVPLQI | 271 | IMAFVPLAV | 120 |
| CD37 | GLAFVPLQI | 271 | IMAFVPLIV | 121 |
| CD37 | GLAFVPLQI | 271 | IMAFVPLVV | 122 |
| CD37 | GLAFVPLQI | 271 | LLAFVPLAL | 123 |
| CD37 | GLAFVPLQI | 271 | LLAFVPLDV | 124 |
| CD37 | GLAFVPLQI | 271 | LLAFVPLML | 125 |
| CD37 | GLAFVPLQI | 271 | LLAFVPLPL | 492 |
| CD37 | GLAFVPLQI | 271 | LLAFVPLSL | 126 |
| CD37 | GLAFVPLQI | 271 | LMAFVPLTL | 127 |
| CD37 | GLAFVPLQI | 271 | TLAFVPLAV | 128 |
| CD37 | GLAFVPLQI | 271 | VLAFVPLGV | 493 |
| CD37 | GLAFVPLQI | 271 | VLAFVPLLV | 129 |
| CD37 | GLAFVPLQI | 271 | VMAFVPLVV | 130 |
| CD37 | GLYFGMLLL | 272 | FLYFGMLLL | 131 |
| CD37 | GLYFGMLLL | 272 | GLYFGMLHM | 132 |
| CD37 | GLYFGMLLL | 272 | LLYFGMLGL | 133 |
| CD37 | GLYFGMLLL | 272 | LLYFGMLLL | 134 |
| CD37 | GLYFGMLLL | 272 | TMYFGMLYL | 135 |
| CD37 | GLYFGMLLL | 272 | VLYFGMLLI | 136 |
| CD37 | ILIDKTSFV | 273 | CLIDKTSVV | 137 |
| CD37 | ILIDKTSFV | 273 | FLIDKTSAA | 138 |
| CD37 | ILIDKTSFV | 273 | ILIDKTSGA | 139 |
| CD37 | ILIDKTSFV | 273 | ILIDKTSGV | 140 |
| CD37 | ILIDKTSFV | 273 | IMIDKTSTV | 141 |
| CD37 | ILIDKTSFV | 273 | VIIDKTSSV | 142 |
| CD37 | ILIDKTSFV | 273 | VLIDKTSQL | 143 |
| CD37 | ILIDKTSFV | 273 | VLIDKTSSV | 144 |
| CD37 | ILIDKTSFV | 273 | YLIDKTSNI | 145 |
| CD37 | ILIDKTSFV | 273 | YLIDKTSNL | 146 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
| --- | --- | --- | --- | --- |
| CD37 | ILIDKTSFV | 273 | YLIDKTSTV | 147 |
| CD37 | LLLLFATQI | 274 | FILLFATHV | 148 |
| CD37 | LLLLFATQI | 274 | FLLLFATSV | 149 |
| CD37 | LLLLFATQI | 274 | LLLLFATAV | 150 |
| CD37 | LLLLFATQI | 274 | LLLLFATSV | 151 |
| CD37 | LLLLFATQI | 274 | LMLLFATSV | 152 |
| CD37 | LLLLFATQI | 274 | MMLLFATLL | 153 |
| CD37 | LLLLFATQI | 274 | YLLLFATNV | 154 |
| CD37 | LLLLFATQI | 274 | YLLLFATYL | 155 |
| CD37 | SIVGICLGV | 275 | ILVGICLGV | 156 |
| CD37 | SIVGICLGV | 275 | SIVGICLNV | 157 |
| CD37 | SLIKYFLFV | 276 | KLIKYFLKV | 158 |
| CD37 | SLIKYFLFV | 276 | KLIKYFLVV | 159 |
| CD37 | SLIKYFLFV | 276 | MMIKYFLCV | 160 |
| CD37 | SLIKYFLFV | 276 | NLIKYFLYV | 161 |
| CD37 | SLIKYFLFV | 276 | SLIKYFLSI | 162 |
| TNFRSF13C | ALVLALVLV | 277 | ALVLALVGV | 163 |
| TNFRSF13C | ALVLALVLV | 277 | ALVLALVPV | 164 |
| TNFRSF13C | ALVLALVLV | 277 | GLVLALVGV | 165 |
| TNFRSF13C | ALVLALVLV | 277 | NLVLALVEV | 166 |
| TNFRSF13C | ALVLALVLV | 277 | SLVLALVGV | 167 |
| TNFRSF13C | ALVLALVLV | 277 | SLVLALVSV | 168 |
| TNFRSF13C | ALVLALVLV | 277 | SLVLALVYV | 169 |
| TNFRSF13C | ALVLALVLV | 277 | TLVLALVSV | 170 |
| TNFRSF13C | GLALVLALV | 278 | ALALVLALL | 171 |
| TNFRSF13C | GLALVLALV | 278 | ALALVLAML | 172 |
| TNFRSF13C | GLALVLALV | 278 | ALALVLATV | 173 |
| TNFRSF13C | GLALVLALV | 278 | FLALVLAAA | 174 |
| TNFRSF13C | GLALVLALV | 278 | FLALVLAAL | 175 |
| TNFRSF13C | GLALVLALV | 278 | FLALVLAGL | 176 |
| TNFRSF13C | GLALVLALV | 278 | FLALVLAGV | 177 |
| TNFRSF13C | GLALVLALV | 278 | FLALVLALL | 178 |
| TNFRSF13C | GLALVLALV | 278 | FLALVLAML | 179 |
| TNFRSF13C | GLALVLALV | 278 | FLALVLATL | 180 |
| TNFRSF13C | GLALVLALV | 278 | GLALVLAAI | 181 |
| TNFRSF13C | GLALVLALV | 278 | GLALVLAAL | 182 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | GLALVLALV | 278 | GLALVLAAV | 183 |
| TNFRSF13C | GLALVLALV | 278 | GLALVLALL | 184 |
| TNFRSF13C | GLALVLALV | 278 | GLALVLALV | 185 |
| TNFRSF13C | GLALVLALV | 278 | GLALVLANI | 186 |
| TNFRSF13C | GLALVLALV | 278 | GLALVLATL | 187 |
| TNFRSF13C | GLALVLALV | 278 | GLALVLATV | 188 |
| TNFRSF13C | GLALVLALV | 278 | GLALVLAVV | 189 |
| TNFRSF13C | GLALVLALV | 278 | GMALVLAAV | 190 |
| TNFRSF13C | GLALVLALV | 278 | ILALVLAMV | 191 |
| TNFRSF13C | GLALVLALV | 278 | ILALVLARV | 192 |
| TNFRSF13C | GLALVLALV | 278 | ILALVLAYL | 193 |
| TNFRSF13C | GLALVLALV | 278 | KLALVLAML | 194 |
| TNFRSF13C | GLALVLALV | 278 | LLALVLAEV | 195 |
| TNFRSF13C | GLALVLALV | 278 | MLALVLAGL | 196 |
| TNFRSF13C | GLALVLALV | 278 | SLALVLALL | 197 |
| TNFRSF13C | GLALVLALV | 278 | SLALVLALV | 198 |
| TNFRSF13C | GLALVLALV | 278 | SLALVLAML | 199 |
| TNFRSF13C | GLALVLALV | 278 | VLALVLAEL | 200 |
| TNFRSF13C | GLALVLALV | 278 | VLALVLAEV | 201 |
| TNFRSF13C | GLALVLALV | 278 | VLALVLAGV | 202 |
| TNFRSF13C | GLALVLALV | 278 | VLALVLALV | 203 |
| TNFRSF13C | GLALVLALV | 278 | VLALVLAMV | 204 |
| TNFRSF13C | GLALVLALV | 278 | VLALVLATV | 205 |
| TNFRSF13C | GLALVLALV | 278 | YLALVLAFL | 206 |
| TNFRSF13C | GLALVLALV | 278 | YLALVLALI | 207 |
| TNFRSF13C | GLALVLALV | 278 | YLALVLALL | 208 |
| TNFRSF13C | GLALVLALV | 278 | YLALVLAML | 209 |
| TNFRSF13C | LLFGAPALL | 279 | ALFGAPAAA | 494 |
| TNFRSF13C | LLFGAPALL | 279 | ALFGAPAAV | 210 |
| TNFRSF13C | LLFGAPALL | 279 | ALFGAPAKL | 211 |
| TNFRSF13C | LLFGAPALL | 279 | FLFGAPASA | 212 |
| TNFRSF13C | LLFGAPALL | 279 | GLFGAPAFI | 213 |
| TNFRSF13C | LLFGAPALL | 279 | ILFGAPAGA | 495 |
| TNFRSF13C | LLFGAPALL | 279 | LLFGAPAAL | 214 |
| TNFRSF13C | LLFGAPALL | 279 | LLFGAPAGI | 215 |
| TNFRSF13C | LLFGAPALL | 279 | LLFGAPAGL | 216 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | LLFGAPALL | 279 | LLFGAPAGV | 217 |
| TNFRSF13C | LLFGAPALL | 279 | LLFGAPALL | 218 |
| TNFRSF13C | LLFGAPALL | 279 | LMFGAPAFV | 219 |
| TNFRSF13C | LLFGAPALL | 279 | LMFGAPALV | 220 |
| TNFRSF13C | LLFGAPALL | 279 | MLFGAPAEA | 221 |
| TNFRSF13C | LLFGAPALL | 279 | NMFGAPAQV | 496 |
| TNFRSF13C | LLFGAPALL | 279 | SLFGAPATA | 497 |
| TNFRSF13C | LLFGAPALL | 279 | SMFGAPAHV | 222 |
| TNFRSF13C | LLFGAPALL | 279 | TLFGAPAAA | 498 |
| TNFRSF13C | LLFGAPALL | 279 | VIFGAPALV | 499 |
| TNFRSF13C | LLFGAPALL | 279 | VLFGAPAGI | 500 |
| TNFRSF13C | LLFGAPALL | 279 | VLFGAPANL | 223 |
| TNFRSF13C | LLFGAPALL | 279 | VLFGAPAYL | 224 |
| TNFRSF13C | LLFGAPALL | 279 | YLFGAPAAA | 225 |
| TNFRSF13C | PLPGLLFGA | 280 | FLPGLLFSV | 226 |
| TNFRSF13C | PLPGLLFGA | 280 | FMPGLLFGA | 227 |
| TNFRSF13C | PLPGLLFGA | 280 | FVPGLLFGV | 228 |
| TNFRSF13C | PLPGLLFGA | 280 | GLPGLLFEL | 229 |
| TNFRSF13C | PLPGLLFGA | 280 | ILPGLLFAI | 230 |
| TNFRSF13C | PLPGLLFGA | 280 | ILPGLLFGL | 231 |
| TNFRSF13C | PLPGLLFGA | 280 | ILPGLLFLI | 232 |
| TNFRSF13C | PLPGLLFGA | 280 | ILPGLLFSL | 233 |
| TNFRSF13C | PLPGLLFGA | 280 | ILPGLLFYI | 234 |
| TNFRSF13C | PLPGLLFGA | 280 | ILPGLLFYM | 235 |
| TNFRSF13C | PLPGLLFGA | 280 | IMPGLLFHI | 236 |
| TNFRSF13C | PLPGLLFGA | 280 | IMPGLLFQV | 237 |
| TNFRSF13C | PLPGLLFGA | 280 | IMPGLLFYV | 238 |
| TNFRSF13C | PLPGLLFGA | 280 | KLPGLLFHA | 239 |
| TNFRSF13C | PLPGLLFGA | 280 | KLPGLLFSV | 240 |
| TNFRSF13C | PLPGLLFGA | 280 | LLPGLLFGL | 241 |
| TNFRSF13C | PLPGLLFGA | 280 | LLPGLLFTL | 242 |
| TNFRSF13C | PLPGLLFGA | 280 | LLPGLLFVV | 243 |
| TNFRSF13C | PLPGLLFGA | 280 | MLPGLLFAL | 244 |
| TNFRSF13C | PLPGLLFGA | 280 | MLPGLLFGL | 245 |
| TNFRSF13C | PLPGLLFGA | 280 | MLPGLLFKV | 246 |
| TNFRSF13C | PLPGLLFGA | 280 | MLPGLLFVV | 247 |

TABLE 1A-continued

HLA-A02 Antigenic peptides according to the invention.

| Tumor antigen | Sequence human reference peptide | SEQ ID NO. human reference peptide | Sequence antigenic peptide | SEQ ID NO. antigenic peptide |
|---|---|---|---|---|
| TNFRSF13C | PLPGLLFGA | 280 | PLPGLLFSV | 248 |
| TNFRSF13C | PLPGLLFGA | 280 | RMPGLLFKV | 249 |
| TNFRSF13C | PLPGLLFGA | 280 | SLPGLLFFL | 250 |
| TNFRSF13C | PLPGLLFGA | 280 | SLPGLLFTL | 251 |
| TNFRSF13C | PLPGLLFGA | 280 | SLPGLLFVV | 252 |
| TNFRSF13C | PLPGLLFGA | 280 | TLPGLLFPA | 253 |
| TNFRSF13C | PLPGLLFGA | 280 | TLPGLLFPV | 254 |
| TNFRSF13C | PLPGLLFGA | 280 | VLPGLLFGV | 255 |
| TNFRSF13C | PLPGLLFGA | 280 | VLPGLLFYV | 256 |
| TNFRSF13C | PLPGLLFGA | 280 | YLPGLLFLM | 257 |

Table 1B below provides an overview over the consensus sequences (MHC Class I Consensus Sequence) of the antigenic peptides according to the present inventions with their amino acid sequences and SEQ ID NOs and with the corresponding fragment/epitope of a human tumor antigen (also referred to herein as "human reference peptide") as well as to their core sequence.

TABLE 1B

MHC Class I Consensus Sequences of the antigenic peptides according to the invention.

| Tumor antigen | Sequence human reference peptide | SEQ ID NO. human reference peptide | Core sequence | SEQ ID NO. core sequence | MHC Class I consensus sequence | SEQ ID NO. consensus sequence |
|---|---|---|---|---|---|---|
| CD19 | FLLFLTPME | 258 | LFLTP | 281 | XXLFLTPXX | 304 |
| CD19 | KLSLGLPGL | 259 | SLGLP | 282 | XXSLGLPXX | 305 |
| CD19 | SLVGILHLQ | 260 | VGILH | 283 | XXVGILHXX | 306 |
| CD19 | TLAYLIFCL | 261 | AYLIF | 284 | XXAYLIFXX | 307 |
| CD19 | QQMGGFYLC | 262 | MGGFY | 285 | XXMGGFYXX | 308 |
| CD20 | IALGGLLMI | 263 | LGGLL | 286 | XXLGGLLXX | 309 |
| CD20 | IMNSLSLFA | 264 | NSLSL | 287 | XXNSLSLXX | 310 |
| CD20 | LMIPAGIYA | 265 | IPAGI | 288 | XXIPAGIXX | 311 |
| CD20 | SLFLGILSV | 266 | FLGIL | 289 | XXFLGILXX | 312 |
| CD22 | FLSNDTVQL | 267 | SNDTV | 290 | XXSNDTVXX | 313 |
| CD22 | HLLGPWLLL | 268 | LGPWL | 291 | XXLGPWLXX | 314 |
| CD22 | ILILAICGL | 269 | ILAIC | 292 | XXILAICXX | 315 |
| CD22 | WVFEHPETL | 270 | FEHPE | 293 | XXFEHPEXX | 316 |
| CD37 | GLAFVPLQI | 271 | AFVPL | 294 | XXAFVPLXX | 317 |

TABLE 1B-continued

MHC Class I Consensus Sequences of the antigenic peptides according to the invention.

| Tumor antigen | Sequence human reference peptide | SEQ ID NO. human reference peptide | Core sequence | SEQ ID NO. core sequence | MHC Class I consensus sequence | SEQ ID NO. consensus sequence |
| --- | --- | --- | --- | --- | --- | --- |
| CD37 | GLYFGMLLL | 272 | YFGML | 295 | XXYFGMLXX | 318 |
| CD37 | ILIDKTSFV | 273 | IDKTS | 296 | XXIDKTSXX | 319 |
| CD37 | LLLLFATQI | 274 | LLFAT | 297 | XXLLFATXX | 320 |
| CD37 | SIVGICLGV | 275 | VGICL | 298 | XXVGICLXX | 321 |
| CD37 | SLIKYFLFV | 276 | IKYFL | 299 | XXIKYFLXX | 322 |
| TNFRSF13C | ALVLALVLV | 277 | VLALV | 300 | XXVLALVXX | 323 |
| TNFRSF13C | GLALVLALV | 278 | ALVLA | 301 | XXALVLAXX | 324 |
| TNFRSF13C | LLFGAPALL | 279 | FGAPA | 302 | XXFGAPAXX | 325 |
| TNFRSF13C | PLPGLLFGA | 280 | PGLLF | 303 | XXPGLLFXX | 326 |

Table 1C below provides an overview over the HLA-A*02 consensus sequences of the antigenic peptides according to the present inventions with their amino acid sequences and SEQ ID NOs and with the corresponding core sequence of a human tumor antigen. Table 1C also provides information to which core sequence and HLA-A*02 consensus sequence each antigenic peptide according to the present invention relates.

Accordingly, the antigenic peptide may comprise or consist of an amino acid sequence as set forth in any one of SEQ ID NOs 309-326. In some embodiments, the antigenic peptide comprises or consists of an amino acid sequence as set forth in any one of SEQ ID Nos 316, 304-315 and 317-472 and 501-509, preferably as set forth in any one of SEQ ID Nos 316, 304-315 and 317-326.

TABLE 1C

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
| --- | --- | --- | --- | --- | --- |
| CD19 | LFLTP | 281 | FLLFLTPXL | 327 | 1-2 |
| CD19 | LFLTP | 281 | FXLFLTPXX | 328 | 1-3 |
| CD19 | LFLTP | 281 | GLLFLTPXX | 329 | 4-6 |
| CD19 | LFLTP | 281 | TLLFLTPXX | 330 | 9-10 |
| CD19 | LFLTP | 281 | XLLFLTPLL | 331 | 2/5, 7-8 |
| CD19 | LFLTP | 281 | XLLFLTPML | 332 | 10-11 |
| CD19 | LFLTP | 281 | XLLFLTPXL | 333 | 1-2, 5, 7-8, 10-12 |
| CD19 | SLGLP | 282 | ALSLGLPXL | 334 | 13-17 |
| CD19 | SLGLP | 282 | AMSLGLPXL | 335 | 18-19 |
| CD19 | SLGLP | 282 | FLSLGLPXL | 336 | 20-21 |
| CD19 | SLGLP | 282 | LLSLGLPXL | 337 | 24-25 |
| CD19 | SLGLP | 282 | SLSLGLPXL | 338 | 28-29 |
| CD19 | SLGLP | 282 | VLSLGLPXX | 339 | 30-32 |
| CD19 | SLGLP | 282 | XLSLGLPGL | 340 | 13, 25, 27 |
| CD19 | SLGLP | 282 | XLSLGLPIL | 341 | 20, 22, 26, 28, 33 |

TABLE 1C-continued

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
|---|---|---|---|---|---|
| CD19 | SLGLP | 282 | XLSLGLPKL | 342 | 21, 29 |
| CD19 | SLGLP | 282 | XLSLGLPXL | 343 | 13-17, 20-30 33 |
| CD19 | VGILH | 283 | XLVGILHXX | 344 | 34-35 |
| CD19 | AYLIF | 284 | FLAYLIFXL | 345 | 36-37 |
| CD19 | AYLIF | 284 | XLAYLIFXL | 346 | 36-39 |
| CD20 | LGGLL | 286 | ALLGGLLXX | 347 | 42-43 |
| CD20 | LGGLL | 286 | AXLGGLLLI | 348 | 41, 43 |
| CD20 | LGGLL | 286 | FXLGGLLXV | 349 | 44, 46 |
| CD20 | LGGLL | 286 | GMLGGLLXX | 350 | 47-48 |
| CD20 | LGGLL | 286 | XLLGGLLXI | 351 | 51-52 |
| CD20 | LGGLL | 286 | SLLGGLLXX | 352 | 56-57 |
| CD20 | LGGLL | 286 | SXLGGLLLI | 353 | 55-56, 58 |
| CD20 | LGGLL | 286 | YXLGGLLMV | 354 | 61, 64 |
| CD20 | LGGLL | 286 | YXLGGLLXV | 355 | 60-61, 64 |
| CD20 | LGGLL | 286 | XLLGGLLLI | 356 | 42, 45, 51-52, 54 |
| CD20 | LGGLL | 286 | XMLGGLLLI | 357 | 47, 58, 62 |
| CD20 | LGGLL | 286 | XXLGGLLMI | 358 | 53, 59, 63 |
| CD20 | LGGLL | 286 | XXLGGLLML | 359 | 43, 48, 57 |
| CD20 | LGGLL | 286 | XXLGGLLMV | 360 | 46, 49, 61, 64 |
| CD20 | NSLSL | 287 | AMNSLSLXX | 501 | 65, 476-477 |
| CD20 | NSLSL | 287 | ILNSLSLXX | 361 | 66-68, 479-480 |
| CD20 | NSLSL | 287 | XLNSLSLXL | 362 | 67-69 |
| CD20 | NSLSL | 287 | XMNSLSLLX | 502 | 476, 478, 483 |
| CD20 | NSLSL | 287 | XMNSLSLXI | 503 | 65, 483 |
| CD20 | NSLSL | 287 | XMNSLSLXL | 504 | 70, 476, 479 |
| CD20 | NSLSL | 287 | XMNSLSLXX | 363 | 65, 70, 476-477 |
| CD20 | NSLSL | 287 | XXNSLSLXI | 364 | 65-66, 479, 483-484 |
| CD20 | IPAGI | 288 | LLIPAGIXX | 365 | 73-77 |
| CD20 | IPAGI | 288 | MXIPAGIXX | 366 | 78-79 |
| CD20 | IPAGI | 288 | XLIPAGIXL | 367 | 71-72, 75, 77 |
| CD20 | IPAGI | 288 | XMIPAGIXX | 368 | 79-80 |
| CD20 | IPAGI | 288 | XXIPAGIAV | 369 | 73, 79 |
| CD20 | FLGIL | 289 | FLFLGILXL | 370 | 81-82 |
| CD20 | FLGIL | 289 | YLFLGILXL | 371 | 85-87 |
| CD20 | FLGIL | 289 | YLFLGILXX | 372 | 84-87 |

TABLE 1C-continued

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
|---|---|---|---|---|---|
| CD20 | FLGIL | 289 | XLFLGILGL | 373 | 81, 85 |
| CD20 | FLGIL | 289 | XLFLGILSX | 374 | 83, 86 |
| CD22 | SNDTV | 290 | FLSNDTVXL | 375 | 88-89 |
| CD22 | SNDTV | 290 | FLSNDTVXX | 376 | 88-90 |
| CD22 | SNDTV | 290 | FXSNDTVXX | 377 | 88-91 |
| CD22 | SNDTV | 290 | XMSNDTVXX | 378 | 91, 93, 95 |
| CD22 | SNDTV | 290 | XLSNDTVWL | 379 | 92, 96 |
| CD22 | SNDTV | 290 | XLSNDTVXL | 380 | 88-89, 92, 94, 96 |
| CD22 | LGPWL | 291 | XLLGPWLXL | 381 | 98, 100 |
| CD22 | LGPWL | 291 | XLLGPWLXV | 382 | 97, 99, 101 |
| CD22 | LGPWL | 291 | XLLGPWLXX | 383 | 97-101 |
| CD22 | ILAIC | 292 | IXILAICXV | 384 | 102-103 |
| CD22 | ILAIC | 292 | XLILAICGV | 385 | 102, 105 |
| CD22 | ILAIC | 292 | XLILAICGX | 386 | 102, 104-105 |
| CD22 | FEHPE | 293 | XIFEHPEXX | 387 | 106-107, 110, 486 |
| CD22 | FEHPE | 293 | XXFEHPELL | 388 | 106, 109 |
| CD22 | FEHPE | 293 | XXFEHPELX | 389 | 108-109 |
| CD22 | FEHPE | 293 | YXFEHPETX | 505 | 110, 488 |
| CD22 | FEHPE | 293 | YXFEHPEXX | 390 | 109-110, 488 |
| CD37 | AFVPL | 294 | ALAFVPLXV | 391 | 111-112 |
| CD37 | AFVPL | 294 | FLAFVPLXL | 392 | 113-115 |
| CD37 | AFVPL | 294 | FXAFVPLQL | 393 | 115-116 |
| CD37 | AFVPL | 294 | IMAFVPLXV | 394 | 120-122 |
| CD37 | AFVPL | 294 | LLAFVPLXL | 395 | 123, 125-126 |
| CD37 | AFVPL | 294 | LLAFVPLXX | 396 | 123-126 |
| CD37 | AFVPL | 294 | XMAFVPLXV | 397 | 120,130 |
| CD37 | AFVPL | 294 | XMAFVPLXL | 398 | 116-117 |
| CD37 | AFVPL | 294 | XLAFVPLAV | 399 | 111,128 |
| CD37 | AFVPL | 294 | XLAFVPLXV | 400 | 111-112, 118, 124, 128-129 |
| CD37 | AFVPL | 294 | XXAFVPLAV | 401 | 111, 120, 128 |
| CD37 | AFVPL | 294 | XXAFVPLXL | 402 | 114, 116-117, 119, 127 |
| CD37 | YFGML | 295 | LLYFGMLXL | 403 | 133-134 |
| CD37 | YFGML | 295 | XLYFGMLXL | 404 | 131, 133-134 |
| CD37 | YFGML | 295 | XLYFGMLXX | 405 | 131-134, 136 |
| CD37 | YFGML | 295 | XXLYFGMLXL | 406 | 131, 133-134, 136 |

TABLE 1C-continued

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
| --- | --- | --- | --- | --- | --- |
| CD37 | IDKTS | 296 | ILIDKTSGX | 407 | 139-140 |
| CD37 | IDKTS | 296 | IXIDKTSXV | 408 | 140-141 |
| CD37 | IDKTS | 296 | VLIDKTSXX | 409 | 143-144 |
| CD37 | IDKTS | 296 | VXIDKTSSV | 410 | 142, 144 |
| CD37 | IDKTS | 296 | YLIDKTSXX | 411 | 145-146 |
| CD37 | IDKTS | 296 | XLIDKTSXA | 412 | 138-139 |
| CD37 | IDKTS | 296 | XLIDKTSXV | 413 | 137, 147 |
| CD37 | IDKTS | 296 | XLIDKTSXX | 414 | 137-139, 143-146 |
| CD37 | LLFAT | 297 | FXLLFATXV | 415 | 148-149 |
| CD37 | LLFAT | 297 | LLLLFATXV | 416 | 150-151 |
| CD37 | LLFAT | 297 | LXLLFATXV | 417 | 150-152 |
| CD37 | LLFAT | 297 | YLLLFATXX | 418 | 154-155 |
| CD37 | LLFAT | 297 | XXLLFATSV | 419 | 149,152 |
| CD37 | LLFAT | 297 | XMLLFATXX | 420 | 152-153 |
| CD37 | VGICL | 298 | XXVGICLXV | 421 | 156-157 |
| CD37 | IKYFL | 299 | KLIKYFLXV | 422 | 158-159 |
| CD37 | IKYFL | 299 | XLIKYFLXV | 423 | 158-159, 161 |
| CD37 | IKYFL | 299 | XLIKYFLXX | 424 | 158-159, 161-162 |
| CD37 | IKYFL | 299 | XXIKYFLXV | 425 | 158-161 |
| TNFRSF13C | VLALV | 300 | ALVLALVXV | 426 | 163-164 |
| TNFRSF13C | VLALV | 300 | SLVLALVXV | 427 | 167-169 |
| TNFRSF13C | VLALV | 300 | XLVLALVXV | 428 | 163-170 |
| TNFRSF13C | ALVLA | 301 | ALALVLAXL | 429 | 171-172 |
| TNFRSF13C | ALVLA | 301 | ALALVLAXX | 430 | 171-173 |
| TNFRSF13C | ALVLA | 301 | FLALVLAAX | 431 | 174-175 |
| TNFRSF13C | ALVLA | 301 | FLALVLAXL | 432 | 175-176, 178-180 |
| TNFRSF13C | ALVLA | 301 | GLALVLAXI | 433 | 181, 186 |
| TNFRSF13C | ALVLA | 301 | GLALVLAXL | 434 | 182, 184, 187 |
| TNFRSF13C | ALVLA | 301 | GLALVLAXV | 435 | 183, 185, 188-190 |
| TNFRSF13C | ALVLA | 301 | GXALVLAVV | 436 | 189-190 |
| TNFRSF13C | ALVLA | 301 | SLALVLALX | 437 | 197-198 |
| TNFRSF13C | ALVLA | 301 | VLALVLAEX | 438 | 200-201 |
| TNFRSF13C | ALVLA | 301 | VLALVLAXV | 439 | 201-205 |
| TNFRSF13C | ALVLA | 301 | YLALVLAXL | 440 | 206, 208-209 |
| TNFRSF13C | ALVLA | 301 | XLALVLAEV | 441 | 195, 201 |
| TNFRSF13C | ALVLA | 301 | XLALVLALL | 442 | 171, 178, 184 |

TABLE 1C-continued

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
|---|---|---|---|---|---|
| TNFRSF13C | ALVLA | 301 | XLALVLAML | 443 | 172, 179, 194 |
| TNFRSF13C | ALVLA | 301 | XLALVLAXL | 444 | 171-172, 175-176, 178-180, 187, 208-209 |
| TNFRSF13C | ALVLA | 301 | XLALVLAXI | 445 | 181, 186, 207 |
| TNFRSF13C | ALVLA | 301 | XLALVLAXV | 446 | 173, 191-192, 198, 201-204 |
| TNFRSF13C | FGAPA | 302 | ALFGAPAAX | 506 | 210, 494 |
| TNFRSF13C | FGAPA | 302 | ALFGAPAXX | 447 | 210-211, 494 |
| TNFRSF13C | FGAPA | 302 | LLFGAPAXL | 448 | 214, 216, 218 |
| TNFRSF13C | FGAPA | 302 | LLFGAPAGX | 449 | 215-217 |
| TNFRSF13C | FGAPA | 302 | LMFGAPAXV | 450 | 219-220 |
| TNFRSF13C | FGAPA | 302 | VLFGAPAXL | 451 | 223-224 |
| TNFRSF13C | FGAPA | 302 | VLFGAPAXX | 507 | 223-224, 500 |
| TNFRSF13C | FGAPA | 302 | XLFGAPAAA | 508 | 225, 494, 498 |
| TNFRSF13C | FGAPA | 302 | XLFGAPAXA | 452 | 212, 221, 225, 494, 498 |
| TNFRSF13C | FGAPA | 302 | XLFGAPAXI | 453 | 213, 215 |
| TNFRSF13C | FGAPA | 302 | XMFGAPAXV | 454 | 219-220, 222, 496 |
| TNFRSF13C | FGAPA | 302 | XMFGAPALV | 509 | 220, 496 |
| TNFRSF13C | FGAPA | 302 | XXFGAPAXV | 455 | 210, 217, 219-220, 222 |
| TNFRSF13C | PGLLF | 303 | FXPGLLFXV | 456 | 226, 228 |
| TNFRSF13C | PGLLF | 303 | ILPGLLFYX | 457 | 234-325 |
| TNFRSF13C | PGLLF | 303 | ILPGLLFXI | 458 | 230, 232, 234 |
| TNFRSF13C | PGLLF | 303 | ILPGLLFXL | 459 | 231, 233 |
| TNFRSF13C | PGLLF | 303 | IMPGLLFXX | 460 | 236-238 |
| TNFRSF13C | PGLLF | 303 | KLPGLLFXX | 461 | 239-240 |
| TNFRSF13C | PGLLF | 303 | LLPGLLFXX | 462 | 241-243 |
| TNFRSF13C | PGLLF | 303 | MLPGLLFXX | 463 | 244-247 |
| TNFRSF13C | PGLLF | 303 | SLPGLLFXX | 464 | 250-252 |
| TNFRSF13C | PGLLF | 303 | TLPGLLFPX | 465 | 253-254 |
| TNFRSF13C | PGLLF | 303 | VLPGLLFXV | 466 | 255-256 |
| TNFRSF13C | PGLLF | 303 | XMPGLLFXX | 467 | 227, 236-238, 249 |
| TNFRSF13C | PGLLF | 303 | XLPGLLFSV | 468 | 226, 240, 248 |
| TNFRSF13C | PGLLF | 303 | XLPGLLFVV | 469 | 243, 247, 252 |
| TNFRSF13C | PGLLF | 303 | XLPGLLFXM | 470 | 235, 257 |
| TNFRSF13C | PGLLF | 303 | XLPGLLFXL | 471 | 229, 231, 241-242, 250-251 |

TABLE 1C-continued

HLA-A02 Consensus Sequences of the antigenic peptides according to the invention.

| Tumor antigen | Core sequence | SEQ ID NO. core sequence | HLA-A02 consensus sequence | SEQ ID NO. consensus sequence | SEQ ID NO. antigenic peptide |
|---|---|---|---|---|---|
| TNFRSF13C | PGLLF | 303 | XLPGLLFXV | 472 | 226, 240, 246-248, 252, 254-256 |

As can be retrieved from Tables 1A-1C the antigenic peptides according to the present invention can be categorized according to the respective human tumor antigen, to the respective core sequence and to the respective MHC Class I and/or HLA-A*02 Consensus Sequences.

Accordingly, the antigenic peptide may comprise a (core) sequence according to any one of SEQ ID NOs 281-303. Preferably, the antigenic peptide comprises a (core) sequence according to any one of SEQ ID NOs 281, 283-289, 293, 294, 302 and 303. More preferably, the antigenic peptide comprises a (core) sequence according to any one of SEQ ID NOs 283, 287, 293, 294, 302 and 303. Even more preferably, the antigenic peptide comprises a (core) sequence according to any one of SEQ ID NOs 287, 293, 294 and 302.

In one embodiment, the antigenic peptide according to the present invention is a sequence variant of a fragment of the tumor antigen CD19 (human reference peptide), such as "FLLFLTPME" (SEQ ID NO: 258), "KLSLGLPGL" (SEQ ID NO: 259), "SLVGILHLQ" (SEQ ID NO: 260), "TLAYLIFCL" (SEQ ID NO: 261) or "QQMGGFYLC" (SEQ ID NO: 262). In a preferred embodiment, the antigenic peptide according to the present invention is a sequence variant of a fragment of the tumor antigen CD19, such as antigenic peptides having a core sequence consisting of an amino acid sequence as set forth in any one of SEQ ID NOs 281-285. Accordingly, the antigenic peptide according to the present invention is a sequence variant of a fragment of the tumor antigen CD19 comprising or consisting of an MHC Class I Consensus Sequence as set forth in any one of SEQ ID Nos 304-308. In a particular embodiment, the antigenic peptide according to the present invention is a sequence variant of a fragment of the tumor antigen CD19 that bind to a particular HLA molecule (HLA-A2*02), such as an antigenic peptide comprising or consisting of an HLA-A2*02 Consensus Sequence as set forth in any one of SEQ ID Nos 327-346. More preferably, the antigenic peptide according to the present invention is a microbiota sequence variant of a fragment of the tumor antigen CD19, such as antigenic peptides comprising or consisting of an amino acid sequence as set forth in any one of SEQ ID NOs 1-40. More preferably, the antigenic peptide according to the present invention is a sequence variant of the CD19 fragment (human reference peptide) "FLLFLTPME" (SEQ ID NO: 258), such as an antigenic peptide comprising or consisting of an amino acid sequence as set forth in SEQ ID NO: 1-12, 304, and 327-333, e.g. an antigenic peptide comprising or consisting of an amino acid sequence as set forth in SEQ ID NO: 10. It is also more preferred that the antigenic peptide according to the present invention is a sequence variant of the CD19 fragment (human reference peptide) "KLSLGLPGL" (SEQ ID NO: 259), such as an antigenic peptide comprising or consisting of an amino acid sequence as set forth in SEQ ID NO: 13-33, 305 and 334-343. It is also more preferred that the antigenic peptide according to the present invention is a sequence variant of the CD19 fragment (human reference peptide) "SLVGILHLQ" (SEQ ID NO: 260), such as an antigenic peptide comprising or consisting of an amino acid sequence as set forth in SEQ ID NO: 34-35, 306 and 344, e.g. an antigenic peptide comprising or consisting of an amino acid sequence as set forth in SEQ ID NO: 34 or 35. It is also more preferred that the antigenic peptide according to the present invention is a sequence variant of the CD19 fragment (human reference peptide) "TLAYLIFCL" (SEQ ID NO: 261), such as an antigenic peptide comprising or consisting of an amino acid sequence as set forth in SEQ ID NO: 36-39, 307 and 345-346, e.g. an antigenic peptide comprising or consisting of an amino acid sequence as set forth in SEQ ID NO: 39. It is also more preferred that the antigenic peptide according to the present invention is a sequence variant of the CD19 fragment (human reference peptide) "QQMGGFYLC" (SEQ ID NO: 262), such as an antigenic peptide comprising or consisting of an amino acid sequence as set forth in SEQ ID NO: 40 and 308, e.g. an antigenic peptide comprising or consisting of an amino acid sequence as set forth in SEQ ID NO: 40.

In one embodiment, the antigenic peptide according to the present invention is a sequence variant of a fragment of the tumor antigen CD20 (MS4A1; human reference peptide), such as "IALGGLLMI" (SEQ ID NO: 263), "IMNSLSLFA" (SEQ ID NO: 264), "LMIPAGIYA" (SEQ ID NO: 265) or "SLFLGILSV" (SEQ ID NO: 266). In a preferred embodiment, the antigenic peptide according to the present invention is a sequence variant of a fragment of the tumor antigen CD20, such as antigenic peptides having a core sequence consisting of an amino acid sequence as set forth in any one of SEQ ID NOs 286-289. Accordingly, the antigenic peptide according to the present invention is a sequence variant of a fragment of the tumor antigen CD20 comprising or consisting of an MHC Class I Consensus Sequence as set forth in any one of SEQ ID Nos 309-312. In a particular embodiment, the antigenic peptide according to the present invention is a sequence variant of a fragment of the tumor antigen CD20 that bind to a particular HLA molecule (HLA-A2*02), such as an antigenic peptide comprising or consisting of an HLA-A2*02 Consensus Sequence as set forth in any one of SEQ ID Nos 347-374. More preferably, the antigenic peptide according to the present invention is a microbiota sequence variant of a fragment of the tumor antigen CD20, such as antigenic peptides comprising or consisting of an amino acid sequence as set forth in any one of SEQ ID NOs 41-87. More preferably, the antigenic peptide according to the present invention is a sequence variant of the CD20 fragment (human reference peptide) "IALGGLLMI" (SEQ ID NO: 263), such as an antigenic peptide comprising or consisting of an amino acid sequence as set forth in SEQ ID NO: 41-64, 309, and 347-360, e.g. an antigenic peptide comprising or consisting of an amino acid sequence as set forth in SEQ ID NO: 61. It is also more preferred that the antigenic peptide according to the present invention is a sequence variant of the CD20 fragment (human reference peptide) "IMNSLSLFA" (SEQ ID NO: 264), such as an antigenic peptide comprising or consisting of an amino acid sequence as set forth in SEQ ID NO: 65-70, 310 and 361-364 and 476-484, e.g. an antigenic peptide comprising or consisting of an amino acid sequence as set forth in any one of SEQ ID NO: 65, 68, 70 and 477. It is also more preferred that the antigenic peptide according to the present invention is a sequence variant of the CD20 fragment (human reference peptide) "LMIPAGIYA" (SEQ ID NO: 265), such as an antigenic peptide comprising or consisting of an amino acid sequence as set forth in SEQ ID NO: 71-80, 311 and 365-369, e.g. an antigenic peptide comprising or consisting of an amino acid sequence as set forth in SEQ ID NO: 72. It is also more preferred that the antigenic peptide according to the present invention is a sequence variant of the CD20 fragment (human reference peptide) "SLFLGILSV" (SEQ ID NO: 266), such as an antigenic peptide comprising or consisting of an amino acid sequence as set forth in SEQ ID NO: 81-87, 312 and 370-374, e.g. an antigenic peptide comprising or consisting of an amino acid sequence as set forth in SEQ ID NO: 86.

In one embodiment, the antigenic peptide according to the present invention is a sequence variant of a fragment of the tumor antigen CD22 (human reference peptide), such as "FLSNDTVQL" (SEQ ID NO: 267), "HLLGPWLLL" (SEQ ID NO: 268), "ILILAICGL" (SEQ ID NO: 269) or "WVFEHPETL" (SEQ ID NO: 270). In a preferred embodiment, the antigenic peptide according to the present invention is a sequence variant of a fragment of the tumor antigen CD22, such as antigenic peptides having a core sequence consisting of an amino acid sequence as set forth in any one of SEQ ID NOs 290-293. Accordingly, the antigenic peptide according to the present invention is a sequence variant of a fragment of the tumor antigen CD22 comprising or consisting of an MHC Class I Consensus Sequence as set forth in any one of SEQ ID Nos 313-316. In a particular embodiment, the antigenic peptide according to the present invention is a sequence variant of a fragment of the tumor antigen CD22 that bind to a particular HLA molecule (HLA-A2*02), such as an antigenic peptide comprising or consisting of an HLA-A2*02 Consensus Sequence as set forth in any one of SEQ ID Nos 375-390. More preferably, the antigenic peptide according to the present invention is a microbiota sequence variant of a fragment of the tumor antigen CD22, such as antigenic peptides comprising or consisting of an amino acid sequence as set forth in any one of SEQ ID NOs 88-110. More preferably, the antigenic peptide according to the present invention is a sequence variant of the CD22 fragment (human reference peptide) FLSNDTVQL" (SEQ ID NO: 267), such as an antigenic peptide comprising or consisting of an amino acid sequence as set forth in SEQ ID NO: 88-96, 313, and 375-380. It is also more preferred that the antigenic peptide according to the present invention is a sequence variant of the CD22 fragment (human reference peptide) "HLLGPWLLL" (SEQ ID NO: 268), such as an antigenic peptide comprising or consisting of an amino acid sequence as set forth in SEQ ID NO: 97-101, 314 and 381-383. It is also more preferred that the antigenic peptide according to the present invention is a sequence variant of the CD22 fragment (human reference peptide) "ILILAICGL" (SEQ ID NO: 269), such as an antigenic peptide comprising or consisting of an amino acid sequence as set forth in SEQ ID NO: 102-105, 315 and 384-386. It is also more preferred that the antigenic peptide according to the present invention is a sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110.

In one embodiment, the antigenic peptide according to the present invention is a sequence variant of a fragment of the tumor antigen CD37 (human reference peptide), such as "GLAFVPLQI" (SEQ ID NO: 271), "GLYFGMLLL" (SEQ ID NO: 272), "ILILAICGL" (SEQ ID NO: 273), "LLLLFATQI" (SEQ ID NO: 274), "SIVGICLGV" (SEQ ID NO: 275) or "SLIKYFLFV" (SEQ ID NO: 276). In a preferred embodiment, the antigenic peptide according to the present invention is a sequence variant of a fragment of the tumor antigen CD37, such as antigenic peptides having a core sequence consisting of an amino acid sequence as set forth in any one of SEQ ID NOs 294-299. Accordingly, the antigenic peptide according to the present invention is a sequence variant of a fragment of the tumor antigen CD37 comprising or consisting of an MHC Class I Consensus Sequence as set forth in any one of SEQ ID Nos 317-322. In a particular embodiment, the antigenic peptide according to the present invention is a sequence variant of a fragment of the tumor antigen CD37 that bind to a particular HLA molecule (HLA-A2*02), such as an antigenic peptide comprising or consisting of an HLA-A2*02 Consensus Sequence as set forth in any one of SEQ ID Nos 391-425. More preferably, the antigenic peptide according to the present invention is a microbiota sequence variant of a fragment of the tumor antigen CD37, such as antigenic peptides comprising or consisting of an amino acid sequence as set forth in any one of SEQ ID NOs 111-162. More preferably, the antigenic peptide according to the present invention is a sequence variant of the CD37 fragment (human reference peptide) "GLAFVPLQI" (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493. It is also more preferred that the antigenic peptide according to the present invention is a sequence variant of the CD37 fragment (human reference peptide) "GLYFGMLLL" (SEQ ID NO: 272), such as an antigenic peptide comprising or consisting of an amino acid sequence as set forth in SEQ ID NO: 131-136, 318 and 403-406. It is also more preferred that the antigenic peptide according to the present invention is a sequence variant of the CD37 fragment (human reference peptide) "ILILAICGL" (SEQ ID NO: 273), such as an antigenic peptide comprising or consisting of an amino acid sequence as set forth in SEQ ID NO: 137-147, 319 and 407-414. It is also more preferred that the antigenic peptide according to the present invention is a sequence variant of the CD37 fragment (human reference peptide) "LLLLFATQI" (SEQ ID NO: 274), such as an antigenic peptide comprising or consisting of an amino acid sequence as set forth in SEQ ID NO: 148-155, 320 and 415-420. It is also more preferred that the antigenic peptide according to the present invention is a sequence variant of the CD37 fragment (human reference peptide) "SIVGICLGV" (SEQ ID NO: 275), such as an antigenic peptide comprising or consisting of an amino acid sequence as set forth in SEQ ID NO: 156-157, 321 and 421. It is also more preferred that the antigenic peptide according to the present invention is a sequence variant of the CD37 fragment (human reference peptide) "SLIKYFLFV" (SEQ ID NO: 276), such as an antigenic peptide comprising or consisting of an amino acid sequence as set forth in SEQ ID NO: 158-162, 322 and 422-425.

In one embodiment, the antigenic peptide according to the present invention is a sequence variant of a fragment of the tumor antigen TNFRSF13C (human reference peptide), such as "GLAFVPLQI" (SEQ ID NO: 277), "GLALVLALV" (SEQ ID NO: 278), "LLFGAPALL" (SEQ ID NO: 279), "PLPGLLFGA" or (SEQ ID NO: 280). In a preferred embodiment, the antigenic peptide according to the present invention is a sequence variant of a fragment of the tumor antigen TNFRSF13C, such as antigenic peptides having a core sequence consisting of an amino acid sequence as set forth in any one of SEQ ID NOs 300-303. Accordingly, the antigenic peptide according to the present invention is a sequence variant of a fragment of the tumor antigen TNFRSF13C comprising or consisting of an MHC Class I Consensus Sequence as set forth in any one of SEQ ID Nos 323-326. In a particular embodiment, the antigenic peptide according to the present invention is a sequence variant of a fragment of the tumor antigen TNFRSF13C that bind to a particular HLA molecule (HLA-A2*02), such as an antigenic peptide comprising or consisting of an HLA-A2*02 Consensus Sequence as set forth in any one of SEQ ID Nos 426-472. More preferably, the antigenic peptide according to the present invention is a microbiota sequence variant of a fragment of the tumor antigen TNFRSF13C, such as antigenic peptides comprising or consisting of an amino acid sequence as set forth in any one of SEQ ID NOs 163-257. More preferably, the antigenic peptide according to the present invention is a sequence variant of the TNFRSF13C fragment (human reference peptide) "GLAFVPLQI" (SEQ ID NO: 277), such as an antigenic peptide comprising or consisting of an amino acid sequence as set forth in SEQ ID NO: 163-170, 323, and 426-428. It is also more preferred that the antigenic peptide according to the present invention is a sequence variant of the TNFRSF13C fragment (human reference peptide) "GLALVLALV" (SEQ ID NO: 278), such as an antigenic peptide comprising or consisting of an amino acid sequence as set forth in SEQ ID NO: 171-209, 324 and 429-446. It is also more preferred that the antigenic peptide according to the present invention is a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224. It is also more preferred that the antigenic peptide according to the present invention is a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 226-257, 326 and 456-472, e.g. an antigenic peptide comprising or consisting of an amino acid sequence as set forth in SEQ ID NO: 227.

Preferably, the antigenic peptide according to the present invention comprises or consists of an MHC Class I Consensus Sequence as set forth in any one of SEQ ID Nos 304-312, 315-316 and 325. More preferably, the antigenic peptide according to the present invention comprises or consists of an HLA-A*02 Consensus Sequence as set forth in any one of SEQ ID Nos. 330, 332-333, 336, 341-344, 346, 354-355, 360, 363-364, 367, 371-372, 374, 387, 390, 392-393, 402 and 450.

In some embodiments, the antigenic peptide comprises or consists of an amino acid sequence as set forth in any one of SEQ ID NOs 1-12, 34-35, 36-39, 40, 41-64, 65-70, 476-484, 71-80, 81-87, 106-110, 485-488, 111-130, 489-493, 210-225, 494-500 and 226-257; preferably the antigenic peptide comprises or consists of an amino acid sequence as set forth in any one of SEQ ID NOs 34-35, 65-70, 476-484, 106-110, 485-488, 111-130, 489-493, 210-225, 494-500 and 226-257; more preferably the antigenic peptide comprises or consists of an amino acid sequence as set forth in any one of SEQ ID NOs 65-70, 476-484, 106-110, 485-488, 111-130, 489-493, 210-225 and 494-500.

In some embodiments, the antigenic peptide comprises or consists of an amino acid sequence as set forth in any one of SEQ ID NOs 10, 34, 35, 39, 40, 61, 68, 70, 72, 86, 107-110, 114, 117, 119, 120, 212, 217, 220, 224, 227, 231, 477, 491 and 493. Even more preferably, the antigenic peptide according to the present invention comprises or consists of an amino acid sequence as set forth in any one of SEQ ID NOs 10, 21, 33, 35, 39, 40, 61, 65, 68, 72, 86, 110, 114 and 220. Still more preferably, the antigenic peptide according to the present invention comprises or consists of an amino acid sequence as set forth in any one of SEQ ID NOs 10, 21, 33, 35, 39, 40, 110, 114 and 220. Most preferably, the antigenic peptide according to the present invention comprises or consists of an amino acid sequence as set forth in any one of SEQ ID NOs 10, 110, 114 and 220. Still more preferably, the antigenic peptides according to the present invention comprises or consists of an amino acid sequence as set forth in any one of SEQ ID NOs 65, 110, 114 and 220. In some embodiments, the antigenic peptide comprises or consists of an amino acid sequence as set forth in SEQ ID NO: 65. In some embodiments, the antigenic peptide comprises or consists of an amino acid sequence as set forth in SEQ ID NO: 110. In some embodiments, the antigenic peptide comprises or consists of an amino acid sequence as set forth in SEQ ID NO: 114. In some embodiments, the antigenic peptide comprises or consists of an amino acid sequence as set forth in SEQ ID NO: 220.

As shown in the examples herein, the specific antigenic peptides according to the present invention allow the raise of a strong immune response against themselves, and most importantly, allow the raise of a strong immune response against peptides having amino acid similarity therewith which are comprised in the tumor antigen, even if the human reference peptides comprised in the tumor antigen may be tolerogenic.

Advantageously, the antigenic peptides according to the present invention may be in the form of immunogenic compounds, in particular for use in the prevention or in the treatment of B-cell malignancy.

Immunogenic Compounds Comprising the Antigenic Peptide According to the Invention In a further aspect, the present invention also provides an immunogenic compound comprising an antigenic peptide according to the present invention as described above. In particular, preferred embodiments of the antigenic peptide as described above also apply for the immunogenic compound according to the present invention. For example, the antigenic peptide comprised in the immunogenic compound preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, immunogenic compound comprising distinct antigenic peptides according to the present invention.

As used herein, the term "immunogenic compound" refers to a compound that is able to induce, increase, prolong or maintain an immune response, in particular which induces, increases, prolongs or maintains an immune response, when it is administered to a mammal, and especially when it is administered to a human individual.

In general, the term "immunogenic compound" includes all kinds of compounds comprising the antigenic peptide according to the present invention. For example, the antigenic peptide according to the present invention may be linked to a carrier molecule or the antigenic peptide according to the present invention may be comprised in a polypeptide or protein (which polypeptide or protein may occur "separately", i.e. not linked to any other compound, or the polypeptide or protein comprising the antigenic peptide may be linked to a carrier molecule).

Preferably, the immunogenic compound according to present invention comprises the antigenic peptide and a carrier molecule, in particular wherein the antigenic peptide (or a polypeptide or protein comprising the antigenic peptide) is linked to a carrier molecule. A preferred carrier molecule is a carrier protein or a carrier peptide. According to a preferred embodiment, the antigenic peptide as above defined, or a polypeptide/protein comprising said antigenic peptide, is linked to a carrier protein or a carrier peptide, for example by a covalent or non-covalent bond. Alternatively, such a carrier protein or carrier peptide (as described herein) may be (separately) co-administered in the form of immune adjuvant (i.e., not as an "immunogenic compound", but as co-administration/combination therapy as described herein below).

The carrier molecule may also be a lipid or a lipid-like moiety. In this case, the immunogenic compound may be a lipopeptide. As used herein, the term "lipopeptide" refers to a molecule that comprises a lipid or a lipid-like moiety covalently linked to a peptide moiety. In general, a "lipid" is soluble in nonpolar solvents, but usually a "lipid" does not (or does not easily) dissolve in water. Examples of a lipid or a lipid-like moiety include, but are not limited to, fatty acids, waxes, sterols, monoglycerides, diglycerides, triglycerides and phospholipids. The lipid may be a fatty acid, a glycerolipid, a gylcerophospholipid, a sphingolipid, a sterol lipid, a prenol lipid, a saccharolipid, or a polyketide. Preferably, the lipid is a fatty acid or a derivative thereof (including monoglycerides, diglycerides, triglycerides and phospholipids). Fatty acids typically contain a hydrocarbon chain that terminates with a carboxylic group. Fatty acids may be saturated or unsaturated. Fatty acids may be attached to functional groups, e.g., containing oxygens, halogens, nitrogen or sulfur. Preferred fatty acids are saturated or unsaturated long-chain fatty acids, such as myristic acid with 14 carbon atoms ($CH_3(CH_2)_{12}COOH$) or palmitic acid with 16 carbon atoms ($CH_3(CH_2)_{14}COOH$), as well as phospholipids, such as phosphatidylglycerol (PG).

Preferably, the antigenic peptide as described herein, or a polypeptide/protein comprising the antigenic peptide, may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least 13 amino acids. In particular, fragments of shared overexpressed tumor antigens, such as HER2, NY-ESO-1, hTERT, having a length of 13 to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; URL: http://www.iedb.org/; http://tools.iedb.org/mhcii/). Preferably, the adjuvant peptide/protein may be the HHD-DR3 peptide of sequence MAK-TIAYDEEARRGLERGLN (SEQ ID NO: 473). Another preferred example is h-pAg T13L (sequence: TPPAY-RPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred adjuvant peptides/proteins, in particular of helper peptides, include the UCP2 peptide (for example as described in WO 2013/135553 A1 or in Dosset et al. Clin Cancer Res. 2012 Nov. 15; 18(22):

6284-95) and the BIRC5 peptide (for example as described in EP2119726 A1 or in Widenmeyer et al. Int J Cancer. 2012 Jul. 1; 131(1):140-9). The most preferred helper peptide is the UCP2 peptide (amino acid sequence: KSVWSKLQSI-GIRQH; SEQ ID NO: 475, for example as described in WO 2013/135553 A1 or in Dosset et al., Clin Cancer Res. 2012 Nov. 15; 18(22):6284-95).

It is also preferred that the immunogenic compound according to the present invention is a polypeptide or a protein comprising the antigenic peptide according to the present invention. Preferably, such a protein or polypeptide is a recombinant protein or polypeptide, for example a fusion protein. The term "recombinant" means that it does not occur in nature.

In a preferred embodiment, the immunogenic compound according to the present invention comprises or consists of a polypeptide of formula (I)

PepNt-CORE-PepCt (I)

wherein:
"PepNt" consists of a polypeptide having a length varying from 0 to 500 amino acid residues and is located at the N-terminal end of the polypeptide of formula (I);
"CORE" consists of an antigenic peptide according to the present invention as defined above; and
"PepCt" consists of a polypeptide having a length varying from 0 to 500 amino acid residues and is located at the C-terminal end of the polypeptide of formula (I).

For example, the immunogenic compound may comprise or consist of a polypeptide of formula (Ia) or (Ib):

PepNt-CORE (Ia); or

CORE-PepCt (Ib)

wherein "PepNt" and "PepCt" and "CORE" are as defined above.

Preferably, the polypeptide of formula (I), (Ia) or (Ib) is a fusion peptide or fusion protein, in particular a recombinant fusion peptide or protein.

It is also preferred that the polypeptide or the immunogenic compound as defined above, comprises from 9 to 1000 amino acids; which includes 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67? 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900 and 1000 amino acids. Accordingly, the length of "PepNt" and "PepCt", if applicable, may be defined accordingly.

Thus, "PepNt" and "PepCt", as defined above, may comprise from 0 to 500 amino acid residues; which includes 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, and 500 amino acid residues.

The types of carrier molecules used for generating an immunogenic compound of the invention, such as an immunogenic compound comprising or consisting of a polypeptide of formula (I) linked to a carrier molecule, are well in the general knowledge of the one skilled in the art. In particular, the function of the carrier molecule is to provide cytokine help (or T-cell help) in order to enhance the immune response against tumor antigen.

Preferably, the antigenic peptide is linked to a carrier molecule, in particular to a carrier protein, preferably by covalent or non-covalent bond. The carrier molecule to which the peptide is optionally bound can be selected from a wide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, E. coli heat labile or tetanus toxoids, the N. meningitidis outer membrane protein (European patent application n° EP0372501), synthetic peptides (European patent applications n° EP0378881 and n° EP0427347), heat shock proteins (PCT application n° WO93/17712), Pertussis proteins (PCT application n° WO98/58668), protein D from H. influenzae (PCT application n° WO00/56360) and toxin A or B from C. difficile (International patent application WO00/61761).

More preferably, the carrier protein or carrier peptide is a protein/peptide having immuno-adjuvant properties, such as providing stimulation of CD4+ Th1 cells as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, or hTERT. In a preferred embodiment, the carrier protein or carrier peptide is a protein/peptide having immuno-adjuvant properties may be a HHD-DR3 carrier peptide MAKTIAYDEEARRGLERGLN (SEQ ID NO: 473). In particular, "PepNt" and/or "PepCt" may correspond to a carrier protein or carrier peptide, such as the HHD-DR3 carrier peptide MAKTIAYDEEARRGLERGLN (SEQ ID NO: 473). Another preferred example is h-pAg T13L (sequence: TPPAYRPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred carrier proteins/peptides, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSIGIRQH; SEQ ID NO: 475).

Moreover, in the polypeptide according to formula (I), (Ia) or (Ib), "PepNt" and/or "PepCt" may preferably correspond to such a protein/peptide having immuno-adjuvant properties, such as providing stimulation of CD4+ Th1 cells as described herein.

Moreover, the immunogenic compound may comprise or consist of such a protein/peptide having immuno-adjuvant properties, such as providing stimulation of CD4+ Th1 cells as described herein, linked covalently to the N-terminus of the antigenic peptide according to the present invention or to the N-Terminus of a polypeptide/protein comprising said antigenic peptide.

Preferably, the antigenic peptide according to the present invention (or the polypeptide/protein comprising said antigenic peptide) is covalently bound to the carrier molecule through a linker moiety.

Preferred linker agents encompass the linker agents named GMBS, sulfo-GMBS, SMPB and sulfo-SMPB.

In some embodiments of an immunogenic compound as defined above, the linker agent is selected from the group consisting of GMBS (N-[γ-maleimidobutyryl-oxy]succinimide ester), Sulfo-GMBS (N-[γ-maleimidobutyryl-oxy] sulfosuccinimide ester), SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of GMBS, Sulfo-GMBS, SMPB and Sulfo-SMPB, are well known by the one skilled in the art. Illustratively, such protocols are disclosed in the leaflets that are made publicly available by the Pierce Company (Illinois, USA). GMBS, Sulfo-GMBS, SMPB and Sulfo-SMPB consist of heterobifunctional linker agents that contain both a N-hydroxysuccinimide (NHS) ester group and a maleimide group. Conjugation using GMBS, Sulfo-GMBS, SMPB or Sulfo-SMPB is usually performed by a two-step procedure. In a first step, the amine-containing protein is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein at pH 6.5-7.5 to form stable thioether bonds.

Using SMPB or Sulfo-SMPB as linker agents for covalently linking the antigenic peptide according to the present invention (or the polypeptide/protein comprising said antigenic peptide, such as the polypeptide of formula (I)) to the amine-containing carrier protein, leads to a conjugate of formula (II) below:

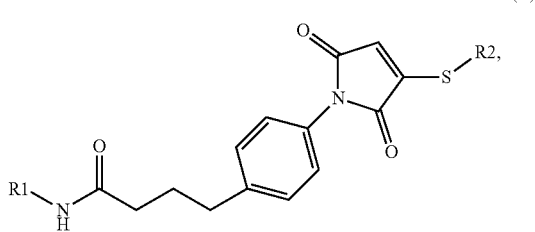

(II)

wherein:
R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and
R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Using GMBS or Sulfo-GMBS as linker agents for covalently linking the antigenic peptide according to the present invention (or the polypeptide/protein comprising said antigenic peptide, such as a polypeptide of formula (I)) to the amine-containing carrier protein, in particular the CRM197 carrier, protein leads to a conjugate of formula (III) below:

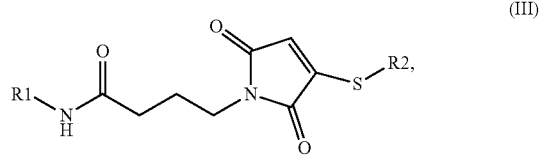

(III)

wherein:
R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and
R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Peptide-MHC (pMHC) Multimers Comprising the Antigenic Peptide

In a further aspect, the present invention also provides a Peptide-MHC (pMHC) multimer comprising an antigenic peptide according to the present invention.

As used herein, the term "peptide-MHC multimer" (pMHC) refers to a stable multimeric complex composed of major histocompatibility complex (MHC) protein subunits loaded with an antigenic peptide of the invention. In general, "MHC multimers" are oligomeric forms of MHC molecules. The main function of an MHC molecule is to bind to an antigen. According to the invention, said antigen is the antigenic peptide according to the invention. Accordingly, a complex of MHC proteins "loaded" with the antigenic peptide of the invention typically means that the antigenic peptide of the invention is bound to one or more of the MHC proteins. The "peptide-MHC multimers" (pMHC) of the invention include, but are not limited to, a peptide-MHC dimer, trimer, tetramer, pentamer, hexamer, heptamer or octamer. MHC tetramers and pentamers are preferred. The term "Major Histocompatibility Complex" (MHC) is a generic designation meant to encompass the histo-compatibility antigen systems described in different species including the human leucocyte antigens (HLA). In humans there are three major different genetic loci that encode MHC class I molecules: HLA-A, HLA-B, and HLA-C. HLA-A*01, HLA-A*02, and HLA-A*11 are examples of different MHC class I alleles that can be expressed from these loci.

In one embodiment of the invention, the pMHC multimer is a peptide/MHC class I multimer. In another particular embodiment, the pMHC multimer is a HLA corresponding to MHC class I/peptide multimer. Accordingly, the pMHC multimer may be a HLA-peptide multimer selected from the group consisting of HLA-A-peptide multimer, HLA-B-peptide multimer, HLA-C-peptide multimer, HLA-E-peptide multimer, MICA-peptide multimer and MICB-peptide multimer.

Methods for obtaining pHMC multimers are known in the art and described, for example, in WO96/26962 and WO01/18053, which are incorporated herein by reference.

In addition to the MHC molecule and the antigenic peptide of the invention, the pMHC may contain further components, such as a multimerization agent and/or a label (e.g., for visualization). Examples of labels include, but are not limited to, fluorescent labels, e.g. fluorescently labelled proteins, such as streptavidin. Fluorescent labels include allophycocyanin (APC), phycoerythrin (PE), R-phycoerythrin (R-PE) and fluorescein isothiocyanate (FITC). A preferred label is biotin.

In one embodiment of the invention, said pMHC multimer can be used to visualize T cell populations that are specific for the MHC class I peptide complex or a HLAs corresponding to MHC class I/peptide complex as described here above. For example, the pMHC multimer may be a multimer where the heavy chain of the MHC is biotinylated, which allows combination as a tetramer with streptavidine. Such pMHC tetramer has an increased avidity for the appropriate TCR-carrier T lymphocytes and can therefore be used to visualize reactive populations by immunofluorescence. In another embodiment of the invention, said pMHC multimer can be used for the detection and/or isolation by screening (in flow cytometry or by immunomagnetic screening) of T cell populations that are specific for a pMHC complex as described here above.

Antigenic Peptide-Specific Cytotoxic T Lymphocytes (CTL)

In a further aspect, the present invention also provides a cytotoxic T lymphocyte (CTL) specific for an antigenic peptide according to the invention, in particular an activated cytotoxic T lymphocyte (CTL) specific for an antigenic peptide according to the invention.

The present invention further provides a method for producing cytotoxic T lymphocytes (CTL) specific for an antigenic peptide according to the invention, in particular activated cytotoxic T lymphocytes (CTL) specific for an antigenic peptide according to the invention, the method comprising contacting in vitro a CTL with an antigen-loaded human class I or II MHC molecule expressed on the surface of an antigen-presenting cell or an artificial construct mimicking an antigen-presenting cell, wherein said antigen is an antigenic peptide according to the invention. Preferred antigen-presenting cells include dendritic cells. An artificial construct mimicking an antigen-presenting cell may be, for instance, a peptide-MHC multimer according to the invention. The step of contacting the CTL with the antigen-loaded human class I or II MHC molecule expressed on the surface of the antigen-presenting cell or the artificial construct mimicking an antigen-presenting cell may be carried out for a period of time sufficient to activate said CTL in an antigen specific manner. Preferably, the antigenic peptide is a preferred antigenic peptide as described above, such as an antigenic peptide comprising or consisting of an amino acid sequence as set forth in any one of SEQ ID NOs 65, 110, 114 and 220.

The (activated) T cells that are directed against the antigenic peptides of the invention are useful in therapy. In particular, activated T cells, which are produced by the above method, selectively recognize a cell that aberrantly expresses a polypeptide that comprises an amino acid sequence of SEQ ID NO: 258-280 (i.e., a tumor antigen), for example, a polypeptide that comprises an amino acid sequence of as set forth in any one of SEQ ID NOs 264, 270, 271 and 279.

Preferably, the (activated) cytotoxic T lymphocytes (CTL) according to the present invention, which are specific for an antigenic peptide of the invention, may have (exhibit/express) memory markers. Such memory markers are preferably memory markers of gut memory cells, such as CCR9, CXCR3, CD103, CX3CR1 and α4β7+.

The (activated) cytotoxic T lymphocytes (CTL) according to the present invention, which are specific for an antigenic peptide of the invention, are preferably more/stronger amplified after vaccination with antigenic peptide of the invention (derived from human microbiota sequences) as compared to vaccination with peptides not derived from microbiota sequences, such as the human (reference) sequence and/or a synthetic peptide (e.g., including mutations, which were, e.g., artificially introduced). In other words, vaccination of subjects with the antigenic peptide of the invention preferably increases the number of (activated) cytotoxic T lymphocytes (CTL) according to the present invention, which are specific for said antigenic peptide of the invention, more than vaccination with respective human peptides or synthetic peptides (not derived from microbiota), which relate to the same reference epitope.

The (activated) cytotoxic T lymphocytes (CTL) according to the present invention, which are specific for an antigenic peptide of the invention, are preferably more/stronger and/or faster amplified after vaccination in subjects having said peptide in the gut (expressed by the subject's microbiota), e.g., the peptide can be found in a stool sample of the subject, as compared to subjects not having said peptide in the gut (not expressed by the subject's microbiota), e.g. subjects where said peptide is not detectable in stool samples. In particular, subjects having said peptide in the gut (expressed by the subject's microbiota), may respond faster (faster T cell expansion) and/or have T cells from the desired type Tc1.

Cells Loaded with the Antigenic Peptide or the Immunogenic Compound

In a further aspect, the present invention also provides a cell loaded with an antigenic peptide according to the present invention or with the immunogenic compound comprising an antigenic peptide according to the present invention as described above. In particular, preferred embodiments of the antigenic peptide as described above also apply for such a cell according to the present invention. For example, the antigenic peptide loaded to the cell or comprised in the immunogenic compound loaded to the cell preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, cells loaded with distinct antigenic peptides according to the present invention (or with the respective immunogenic compound(s)).

A preferred cell loaded with the antigenic peptide according to the present invention or with the immunogenic compound according to the present invention is an antigen presenting cell (APC), more preferably a dendritic cell (DC).

APCs are of particular interest, as their main function is to process antigens and present it on the cell surface to the T cells of the immune system, so as to initiate and modulate T-cell responses in vivo. In the context of the present invention, it is preferred that the APCs are loaded with the antigenic peptide(s) and/or immunogenic compound(s) according to the invention. This may be done by exposing APCs in vitro with said antigenic peptide(s) and/or immunogenic compound(s) (as described in Rizzo M M, Alaniz L, Mazzolini G. Ex vivo loading of autologous dendritic cells with tumor antigens. Methods Mol Biol. 2014; 1139:41-4; Rolinski J, Hus I. Breaking immunotolerance of tumors: a new perspective for dendritic cell therapy. J Immunotoxicol. 2014 October; 11(4):311-8).

Preferred APCs according to the invention are dendritic cells (DCs). It can indeed be advantageous to combine at least one antigenic peptide or immunogenic compound according to the invention with DCs, as those are the most potent APCs and have been reported to be frequently functionally defective in cancer patients. DCs can be easily obtained by the skilled person in the art from either healthy compatible donors (i.e. the DCs are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Figdor C G, de Vries I J, Lesterhuis W J, Melief C J. Dendritic cell immunotherapy: mapping the way. Nat Med. 2004 May; 10(5):475-80). DCs can indeed be distinguished from other cells of peripheral blood by their surface markers, such as S100, p55, CD83, and/or OX62, and may thus be isolated and purified based on said markers using cell cultures techniques well-known in the art.

Nucleic Acids Encoding the Antigenic Peptides and Host Cells Comprising Nucleic Acids In a further aspect, the present invention also provides a nucleic acid encoding the antigenic peptide according to the present invention, the polypeptide of formula (I) as defined above, or the immunogenic compound according to the present invention, wherein the immunogenic compound is a peptide or a protein. In particular, preferred embodiments of the antigenic peptide as described above also apply for such a nucleic acid according to the present invention. For example, the antigenic peptide encoded by the nucleic acid preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, nucleic acids encoding distinct antigenic peptides according to the present invention.

Nucleic acids preferably comprise single stranded, double stranded or partially double stranded nucleic acids, preferably selected from gDNA, cDNA, RNA, antisense DNA, antisense RNA, complementary RNA/DNA sequences with or without expression elements, a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

It is of great interest in the fields of therapeutics, diagnostics, reagents and for biological assays to be able to deliver a nucleic acid, e.g., a ribonucleic acid (RNA) inside a cell, whether in vitro, in vivo, in situ or ex vivo, such as to cause intracellular translation of the nucleic acid and production of an encoded peptide of interest. Of particular importance is the delivery and function of a non-integrative polynucleotide. Accordingly, nucleic acids, which do not integrate into the chromosomes of the host, are preferred, such as mRNA. In general, nucleic acids, such as mRNA, may be optimized for expression of the antigenic peptide of the invention, e.g. by methods known in the art, such as codon optimization. In addition, the nucleic acid may be modified, for example, in order to enhance its stability, prolong its lifetime and/or to increase the expression of the antigenic peptide of the invention. Accordingly, optimized or modified mRNA (mmRNA), which encodes an antigenic peptide according to the present invention, is preferred. The mmRNA are distinguished from wild type mRNA in their functional and/or structural design features for optimal delivery of the mRNA and/or for optimal expression of the antigenic peptide of the invention (for example as described in WO 2013/151672 A2, WO 2013/101690 A1, WO2013/052523 A, which are incorporated herein by reference). In general, nucleic acids may be delivered "naked" or associated with a carrier, e.g., a cationic carrier. Cationic carriers (positively charged) typically associate easily with nucleic acids, which are negatively charged. The carrier may be any of any kind including, for example, polymers, proteins, lipids and nanoparticles. Cationic lipids and nanoparticles (in particular lipid nanoparticles, LNPs) are preferred for nucleic acid delivery. Accordingly, the present invention also provides a nucleic acid as described herein associated with a carrier (e.g., a lipid, in particular a cationic lipid or an LNP).

In some embodiments, the nucleic acid molecule may be a vector. The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antigenic peptide according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector. A preferred vector is a vector for expression in bacterial cells. More preferably, the vector is useful for expression in so-called "live bacterial vaccine vectors", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Nucleic acids encoding antigenic peptides according to the invention may be in the form of naked nucleic acids, or nucleic acids cloned into plasmids or viral vectors (Tregoning and Kinnear, Using Plasmids as DNA Vaccines for Infectious Diseases. Microbiol Spectr. 2014 December; 2(6). doi: 10.1128/microbiolspec.PLAS-0028-2014), the latter being particularly preferred. Examples of suitable viral vectors according to the invention include, without limitation, retrovirus, adenovirus, adeno-associated virus (AAV), herpes virus and poxvirus vectors. It is within the skill of the person in the art to clone a nucleic acid into a plasmid or viral vector, using standard recombinant techniques in the art.

In a further aspect, the present invention also provides a host cell comprising the nucleic acid according to the present invention. Also combinations thereof are preferred, namely, host cells comprising distinct nucleic acids according to the present invention, for example encoding distinct antigenic peptides according to the present invention.

Preferably, the nucleic acid comprised in the host cell is preferably a vector. Preferably, the host cell is a bacterial cell. Such a host cell may be preferably used for production of the antigenic peptide according to the present invention or the immunogenic compound according to the present invention. Moreover, such a host cell may also be an active component in a vaccine.

Preferably, the host cell is a bacterial cell, more preferably a gut bacterial cell. The term "gut bacterial cell" refers to bacteria residing in the (human) gut.

Such a bacterial host cell may serve as "live bacterial vaccine vector", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Alternatively, bacterial cells, in particular gut bacteria, according to the invention may be in the form of probiotics, i.e. of live gut bacterium, which can thus be used as food additive due to the health benefits it can provide. Those can be for example lyophilized in granules, pills or capsules, or directly mixed with dairy products for consumption.

Nanoparticles Comprising the Antigenic Peptide or the Immunogenic Compound

In a further aspect, the present invention also provides a nanoparticle comprising, in particular a nanoparticle loaded with,
- at least one of the antigenic peptides according to the present invention, or
- at least one of the immunogenic compounds according to the present invention;

and, optionally, with an adjuvant.

In particular, preferred embodiments of the antigenic peptide as described above also apply for such a nanoparticle according to the present invention. For example, the antigenic peptide loaded to the nanoparticle or comprised in the immunogenic compound loaded to the nanoparticle preferably comprises or consists of MHC Class I Consensus Sequence as set forth in any one of SEQ ID Nos 304-326, such as an antigenic peptide comprising or consisting of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred. Also combinations thereof are preferred, namely, nanoparticles loaded with distinct antigenic peptides according to the present invention (or with the respective immunogenic compound(s)).

Nanoparticles, in particular for use as vaccines, are known in the art and described, for example, in Shao et al., Nanoparticle-based immunotherapy for cancer, ACS Nano 2015, 9(1):16-30; Zhao et al., Nanoparticle vaccines, Vaccine 2014, 32(3):327-37; and Gregory et al., Vaccine delivery using nanoparticles, Front Cell Infect Microbiol. 2013, 3:13, doi: 10.3389/fcimb.2013.00013. eCollection 2013, Review. In particular, the nanoparticle is used for delivery of the antigenic peptide (or the immunogenic compound/polypeptide/protein/nucleic acid comprising the antigenic peptide) and may optionally also act as an adjuvant. The antigenic peptide (the immunogenic compound/polypeptide/protein/nucleic acid comprising the antigenic peptide) is typically either encapsulated within the nanoparticle or linked/bound to (decorated onto) the surface of the nanoparticle ("coating"). Compared to conventional approaches, nanoparticles can protect the payload (antigen/adjuvant) from the surrounding biological milieu, increase the half-life, minimize the systemic toxicity, promote the delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles such as poly(ethylene glycol) (PEG) and poly (D,L-lactic-coglycolic acid) (PLGA); inorganic nanoparticles such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(D,L-lactide-co-glycolide) (PLG), poly(D,L-lactic-coglycolic acid)(PLGA), poly(γ-glutamic acid) (γ-PGA), poly(ethylene glycol) (PEG), and polystyrene. Polymeric nanoparticles may entrap an antigen (e.g., the antigenic peptide or a (poly)peptide comprising the same) or bind to/conjugate to an antigen (e.g., the antigenic peptide or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising PEG and PLGA.

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles.

Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the antigenic peptide according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of SiNPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-3-trimethylammonium propane (DOTAP). In general, cationic liposomes are preferred. Liposomes are self-assembling with a phospholipid bilayer shell and an aqueous core. Liposomes can be generated as unilamellar vesicles (having a single phospholipid bilayer) or as multilamellar vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil-A, cholesterol, phospholipids, and the (poly)peptide antigen (such as the antigenic peptide or a polypeptide comprising the same). These spherical particles can trap the antigen by apolar interactions. Two types of ISCOMs have been described, both of which consist of cholesterol, phospholipid (typically either phosphatidylethanolamine or phosphatidylcholine) and saponin (such as Quil-A).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the antigenic peptide according to the present invention or a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the antigenic peptide according to the present invention.

In general, preferred examples of nanoparticles (NPs) include iron oxide beads, polystyrene microspheres, poly(γ-glutamic acid) (γ-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, the nanoparticle further comprises an adjuvant, for example a toll-like receptor (TLR) agonist. Thereby, the antigenic peptide (the immunogenic compound/polypeptide/protein/nucleic acid comprising the antigenic peptide) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the antigenic peptide.

Particularly preferred adjuvants are polyinosinic: polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Pharmaceutical Compositions

In a further aspect, the present invention also provides a pharmaceutical composition comprising at least one of the following:
- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein, and/or
- the cytotoxic T lymphocyte according to the present invention as described herein, and, optionally, one or more pharmaceutically acceptable excipients or carriers.

Accordingly, the present invention provides a pharmaceutical composition comprising (at least) one antigenic peptide according to the present invention as described herein. Moreover, the present invention also provides a pharmaceutical composition comprising (at least) one immunogenic compound according to the present invention as described herein. Moreover, the present invention also provides a pharmaceutical composition comprising (at least) one nanoparticle according to the present invention as described herein. Moreover, the present invention also provides a pharmaceutical composition comprising (at least) one cell according to the present invention as described herein. Moreover, the present invention also provides a pharmaceutical composition comprising (at least) one nucleic acid according to the present invention as described herein. Moreover, the present invention also provides a pharmaceutical composition comprising (at least) one host cell according to the present invention as described herein. Moreover, the present invention also provides a pharmaceutical composition comprising (at least) one cytotoxic T lymphocyte according to the present invention as described herein.

In particular, preferred embodiments of the antigenic peptide as described above also apply for such a pharmaceutical composition according to the present invention. For example, the antigenic peptide comprised in the pharmaceutical composition or the antigenic peptide comprised in any of the immunogenic compound, the nanoparticle, the cell, the nucleic acid or the host cell comprised by the pharmaceutical composition preferably comprises or consists of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, pharmaceutical compositions comprising distinct antigenic peptides according to the present invention. For example, the pharmaceutical composition may comprise
(i) at least two distinct antigenic peptides according to the present invention;
(ii) at least two distinct immunogenic compounds according to the present invention;
(iii) at least two distinct nanoparticles according to the present invention;
(iv) at least two distinct nucleic acids according to the present invention; and/or
(v) at least two distinct cytotoxic T lymphocytes according to the present invention.

Accordingly, the pharmaceutical composition may comprise at least "two distinct components" (of a pharmaceutical composition according to the present invention), preferably three or four distinct components. In general, the expression "distinct components", as used herein, refers to
(1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the cytotoxic T lymphocyte according to the present invention as described herein; and
(2) at least one other component (which is distinct from the first component; while in the case of more than two distinct components each component is distinct from each other component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct cytotoxic T lymphocyte according to the present invention as described herein, or one or more (fragments of) human tumor antigens in any form ("naked", as immunogenic compound as described herein, as nanoparticle as described herein, as (host) cell as described herein, or as nucleic acid as described herein).

Accordingly, the "distinct components" are preferably active components (as described above) in the context of a disease (B-cell malignancy) to be prevented and/or treated. In other words, each of the distinct components may also be useful for preventing and/or treating said cancer, if administered separately (not in combination as described herein)—although the combination (i.e. combined administration) typically potentiates their preventive and/or therapeutic effect (such as the immune response), preferably in a synergistic manner.

Preferably, the "distinct components" are of the same type (e.g., distinct antigenic peptides, distinct immunogenic compounds, distinct nanoparticles, distinct cells, distinct nucleic acids, distinct host cells, or distinct cytotoxic T lymphocytes) and differ from each other only in that they relate to distinct antigenic peptides of the present invention as described herein.

For example, the at least three or four distinct active components are preferably of the same type, but differ (only) in that each of them relates to a distinct antigenic peptide. More preferably

- a first component relates to the antigenic peptide comprising or consisting of a (microbiota) sequence variant of a fragment of the human tumor antigen CD22;
- a (distinct) second component relates to the antigenic peptide comprising or consisting of a (microbiota) sequence variant of a fragment of the human tumor antigen CD37;
- a (distinct) third component relates to the antigenic peptide comprising or consisting of a (microbiota) sequence variant of a fragment of the human tumor antigen TNFRSF13C; and
- optionally, a (distinct) fourth component relates to the antigenic peptide comprising or consisting of a (microbiota) sequence variant of a fragment of the human tumor antigen MS4A1 (CD20).

Even more preferably

- a first component relates to the antigenic peptide comprising or consisting of a (microbiota) sequence variant of SEQ ID NO: 270;
- a (distinct) second component relates to the antigenic peptide comprising or consisting of a (microbiota) sequence variant of SEQ ID NO: 271;
- a (distinct) third component relates to the antigenic peptide comprising or consisting of a (microbiota) sequence variant of SEQ ID NO: 279; and
- optionally, a (distinct) fourth component relates to the antigenic peptide comprising or consisting of a (microbiota) sequence variant of SEQ ID NO: 264.

Still more preferably

- a first component relates to the antigenic peptide comprising or consisting of an amino acid sequence as set forth in SEQ ID NO: 110;
- a (distinct) second component relates to the antigenic peptide comprising or consisting of an amino acid sequence as set forth in SEQ ID NO: 114;
- a (distinct) third component relates to the antigenic peptide comprising or consisting of an amino acid sequence as set forth in SEQ ID NO: 220; and
- optionally, a (distinct) fourth component relates to the antigenic peptide comprising or consisting of an amino acid sequence as set forth in SEQ ID NO: 65.

Preferably, the pharmaceutical composition comprises at least two distinct antigenic peptides according to the present invention.

Preferably, the pharmaceutical composition comprises a first antigenic peptide according to the present invention, which comprises or consists of a (microbiota) sequence variant of a fragment of the human tumor antigen CD22, and a second antigenic peptide according to the present invention, which comprises or consists of a (microbiota) sequence variant of a fragment of the human tumor antigen TNFRSF13C. Preferably, the first antigenic peptide comprises or consists of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110, and the second antigenic peptide comprises or consists of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450. More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110 and an antigenic peptide comprising or consisting of SEQ ID NO: 220.

More preferably, the pharmaceutical composition comprises at least three distinct antigenic peptides according to the present invention.

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C and a third antigenic peptide according to the present invention, which comprises or consists of a (microbiota) sequence variant of a fragment of the human tumor antigen CD37. Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450 and a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493, in particular as set forth in SEQ ID NO: 113-116, 324 and 392-393.

Still more preferably, the pharmaceutical composition comprises at least four distinct antigenic peptides according to the present invention.

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, a fourth antigenic peptide according to the present invention, which comprises or consists of a (microbiota) sequence variant of a fragment of the human tumor antigen CD19 or CD20. Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390 and 485-488, e.g. an antigenic peptide comprising or consisting of an amino acid sequence as set forth in any one of SEQ ID NO: 107, 108, 109 and 110; a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 210-225, 325 and 447-455 and 494-500, e.g. an antigenic peptide comprising or consisting of an amino acid sequence as set forth in any one of SEQ ID NO: 212, 217, 220 and 224, in particular as set forth in SEQ ID NO: 220, 325 and 450; a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 111-130, 317, and 391-402 and 489-493, e.g. an antigenic peptide comprising or consisting of an amino acid sequence as set forth in any one of SEQ ID NO: 114, 117, 119, 120, 491 and 493, in particular as set forth in SEQ ID NO: 113-116, 324 and 392-393; and a fourth antigenic peptide comprising or consisting of a (microbiota) sequence variant of the CD20 (MS4A1) fragment (human reference peptide) "IMNSLSLFA" (SEQ ID NO: 264), such as an antigenic peptide comprising or consisting of an amino acid sequence as set forth in SEQ ID NO: 65-70, 310 and 361-364 and 476-484, e.g. an antigenic peptide comprising or consisting of an amino acid sequence as set forth in any one of SEQ ID NO: 65, 68, 70 and 477.

Preferably, the pharmaceutical composition comprises:
  a first antigenic peptide according to the present invention, which comprises or consists of a (microbiota) sequence variant of a fragment of the human tumor antigen CD22,
  a second antigenic peptide according to the present invention, which comprises or consists of a (microbiota) sequence variant of a fragment of the human tumor antigen TNFRSF13C,
  a third antigenic peptide according to the present invention, which comprises or consists of a (microbiota) sequence variant of a fragment of the human tumor antigen CD37, and
  optionally, a fourth antigenic peptide according to the present invention, which comprises or consists of a (microbiota) sequence variant of a fragment of the human tumor antigen CD20.

More preferably, the pharmaceutical composition comprises:
  a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390,
  a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450,
  a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, and
  optionally, a fourth antigenic peptide comprising or consisting of a (microbiota) sequence variant of the CD20 fragment (human reference peptide) "IMNSLSLFA" (SEQ ID NO: 264), such as an antigenic peptide comprising or consisting of an amino acid sequence as set forth in SEQ ID NO: 65-70, 310 and 361-364.

Even more preferably, the pharmaceutical composition comprises antigenic peptides according to the present invention comprising or consisting of an amino acid sequence as set forth in SEQ ID NOs 110, 114, 220 and, optionally, 65.

In some embodiments, the pharmaceutical composition does not comprise further antigenic peptides (in addition to the antigenic peptides of the invention as described above).

It is understood that the pharmaceutical composition may also contain—instead of the above-described preferred combinations of antigenic peptides—a respective combination of immunogenic compounds of the invention, a respective combination of nanoparticles of the invention or a respective combination of nucleic acids of the invention.

Preferably, the pharmaceutical composition further comprises one or more pharmaceutically acceptable excipients or carriers.

The pharmaceutical composition of the invention may be in any form suitable for the purposes of the invention. For example, said composition may be in a form suitable for parenteral, enteral or topical administration, such as a liquid suspension, a solid dosage form (granules, pills, capsules or tablets), or a paste or gel. It is within the skill of the person in the art to select the appropriate form of the composition for the intended purpose.

The composition according to the invention can further comprise other active agents, for example such, which can enhance the effects of the antigenic peptide or immunogenic compound. Alternatively, the composition may not comprise any other active agents (i.e., other than the antigenic peptide according to the present invention, the immunogenic compound according to the present invention, the nanoparticle according to the present invention, the cell according to the present invention, the nucleic acid according to the present invention, and/or the host cell according to the present invention).

The pharmaceutical composition as defined herein is preferably an immunogenic composition, i.e. a composition that is able to induce, increase, prolong or maintain an immune response. This may be achieved by an antigenic peptide according to the present invention or by an immunogenic compound according to the present invention comprised in said composition. Preferably, the pharmaceutical composition further comprises one or more immuno-adjuvant substances. A pharmaceutical composition, in particular an immunogenic composition, may also be termed "vaccine composition" in the present specification.

Preferably, the pharmaceutical composition further comprises at least one immunostimulatory agent, in particular so as to increase, potentiate, prolong or maintain the immune response mediated by the antigenic peptide. Preferred immunostimulatory agents according to the invention include, without limitation, immune adjuvants, antigen-presenting cells, and combinations thereof. Preferably, the immunostimulatory agent is an immune adjuvant or an antigen-presenting cell (APC).

Preferably, the immunostimulatory agent is an immune adjuvant. Some immune adjuvants are capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; and oil-based emulsions such as paraffin oil, starch oil, Freund's complete/incomplete adjuvant (FCA/FIA), saponins (e.g. from the plants Quillaja, Soybean, Polygala senega). The adjuvants of belonging to the latter category include, without limitation, immunostimulatory complexes (ISCOMs) such as cytokines (e.g. GM-CSF; Interleukins such as IL-1, IL-2, IL6, ILS, or IL12; Tumor necrosis factors (TNFs) such as TNFα or TNFβ; Interferons IFNS such as IFNα, IFNβ, IFNγ or IFNS, etc); ligands of toll-like receptors (TLRs) such as imiquimod, resiquimod or MPL; exosomes such as exosomes derived from dendritic cells (DCs) or from tumor cells; bacterial products such as heat-shock proteins (HSPs such as gp96, hsp90, hsp70, calreticulin, hsp110, hsp170), pathogen-associated molecular patterns (PAMPs), trehalose dimicolate (TDM), muramyldipeptide (MDP), polysaccharide (PLS) such as polysaccharide-K.

More preferably, the immune adjuvant is a protein/peptide having immuno-adjuvant properties, such as providing stimulation of CD4+ Th1 cells, as described herein ("helper" peptides). A preferred example thereof is a non-tumor antigen that recalls immune memory or provides a non-specific help or could be a specific tumor-derived helper peptide, such as tetanus helper peptide, keyhole limpet hemocyanin peptide or PADRE peptide, as described herein. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In particular, the immune adjuvant may be the HHD-DR3 peptide of sequence MAKTIAYDEEARRGLERGLN (SEQ ID NO: 473). This peptide represents another example of a helper peptide (having immuno-adjuvant properties), which is preferred in the context of the present invention. Another preferred example is h-pAg T13L (sequence: TPPAY-RPPNAPIL; SEQ ID NO: 474; Bhasin M, Singh H, Raghava G P (2003) MHCBN: a comprehensive database of MHC binding and non-binding peptides. Bioinformatics 19: 665-666). Further examples of preferred immune adjuvants, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSI-GIRQH; SEQ ID NO: 475).

Preferably, the pharmaceutical composition comprises at least two distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a sequence variant of a fragment of the human tumor antigen CD22, a second antigenic peptide according to the present invention, which comprises or consists of a sequence variant of a fragment of the human tumor antigen TNFRSF13C and a helper peptide, preferably the UCP2 peptide (SEQ ID NO: 475). Preferably, the pharmaceutical composition comprises a first antigenic peptide comprising or consisting of a sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450 and a helper peptide, preferably the UCP2 peptide (SEQ ID NO: 475). More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110, an antigenic peptide comprising or consisting of SEQ ID NO: 220 and the UCP2 helper peptide (SEQ ID NO: 475).

Still more preferably, the pharmaceutical composition comprises at least three distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37 and a helper peptide, preferably the UCP2 peptide (SEQ ID NO: 475). Preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450, a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, and a helper peptide, preferably the UCP2 peptide (SEQ ID NO: 475).

Most preferably, the pharmaceutical composition comprises at least four distinct antigenic peptides according to the present invention and a helper peptide, preferably the UCP2 peptide (SEQ ID NO: 475).

In particular, the pharmaceutical composition may comprise a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, a fourth antigenic peptide according to the present invention, which comprises or consists of a (microbiota) sequence variant of a fragment of the human tumor antigen CD19 or CD20 and a helper peptide, preferably the UCP2 peptide (SEQ ID NO: 475).

Preferably, the pharmaceutical composition comprises a first antigenic peptide according to the present invention, which comprises or consists of a (microbiota) sequence variant of a fragment of the human tumor antigen CD22, a second antigenic peptide according to the present invention, which comprises or consists of a (microbiota) sequence variant of a fragment of the human tumor antigen TNFRSF13C, a third antigenic peptide according to the present invention, which comprises or consists of a (microbiota) sequence variant of a fragment of the human tumor antigen CD37, (optionally) a fourth antigenic peptide according to the present invention, which comprises or consists of a (microbiota) sequence variant of a fragment of the human tumor antigen CD20, and a helper peptide, preferably the UCP2 peptide (SEQ ID NO: 475). More preferably, the pharmaceutical composition comprises a first antigenic peptide comprising or consisting of a (microbiota) sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, a second antigenic peptide comprising or consisting of a (microbiota) sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450, a third antigenic peptide comprising or consisting of a (microbiota) sequence variant of the CD37 fragment (human reference peptide) "GLAFVPLQI" (SEQ ID NO: 271), such as an antigenic peptide comprising or consisting of an amino acid sequence as set forth in SEQ ID NO: 113-116, 324 and 392-393, (optionally) a fourth antigenic peptide comprising or consisting of a (microbiota) sequence variant of the CD20 fragment (human reference peptide) "IMNSLSLFA" (SEQ ID NO: 264), such as an antigenic peptide comprising or consisting of an amino acid sequence as set forth in SEQ ID NO: 65-70, 310 and 361-364, and a helper peptide, preferably the UCP2 peptide (SEQ ID NO: 475).

Particularly preferred immune adjuvants are polyinosinic:polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLRs. Poly I:C and poly-ICLC typically stimulate the release of cytotoxic cytokines. A preferred example of poly-ICLC is Hiltonol®.

Most preferably, the adjuvant is Montanide, such as Montanide ISA 51 VG and/or Montanide ISA 720 VG. Those adjuvants are rendering stable water-in-oil emulsions when mixed with water based antigenic media. Montanide ISA 51 VG is based on a blend of mannide monooleate surfactant and mineral oil, whereas Montanide ISA 720 VG uses a non-mineral oil (Aucouturier J, Dupuis L, Deville S, Ascarateil S, Ganne V. Montanide ISA 720 and 51: a new generation of water in oil emulsions as adjuvants for human vaccines. Expert Rev Vaccines. 2002 June; 1(1):111-8; Ascarateil S, Puget A, Koziol M-E. Safety data of Montanide ISA 51 VG and Montanide ISA 720 VG, two adjuvants dedicated to human therapeutic vaccines. Journal for Immunotherapy of Cancer. 2015; 3(Suppl 2):P428. doi:10.1186/2051-1426-3-S2-P428).

It is also preferred that the immunostimulatory agent is an antigen-presenting cell (APC). APCs are also of particular interest, as their main function is to process antigens and present it on the cell surface to the T cells of the immune system, so as to initiate and modulate T-cell responses in vivo. In the present composition, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo et al., Methods Mol Biol. 2014; 1139:41-4; Rolinski and Hus, J Immunotoxicol. 2014 October; 11(4):311-8).

Preferably, the APC is a dendritic cell (DC). DCs are the most potent APCs and have been reported to be frequently functionally defective in cancer patients. DCs can be easily obtained by the skilled person in the art from either healthy compatible donors (i.e. the dendritic cells are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Emens et al., 2008). DCs can indeed be distinguished from other cells of peripheral blood by their surface markers, such as S100, p55, CD83, and/or OX62, and may thus be isolated and purified based on said markers using cell cultures techniques well-known in the art.

According to a preferred embodiment, the pharmaceutical composition may further comprise at least one anti-cancer therapeutic agent. Said therapeutic agent is thus preferably capable of preventing and/or treating the same type of cancer than the one for which the antigenic peptide according to the invention is used. Preferably, the anti-cancer therapeutic agent is selected from antibodies, CAR-T cells, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumor antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA-4, B7H3, B7H4, PVR, TIGIT, GAL9, LAG-3, GITR, CD137, TIM3, VISTA, VISTA-R (Pico de Coana et al., Checkpoint blockade for cancer therapy: revitalizing a suppressed immune system. Trends Mol Med. 2015 August; 21(8):482-91; Pardoll D M. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oesaophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oesaophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al., Trial Watch: Immunomodulatory monoclonal antibodies for oncological indications. Oncoimmunology. 2015 Mar. 2; 4(4):e1008814. eCollection 2015 April; Redman et al., Mechanisms of action of therapeutic antibodies for cancer. Mol Immunol. 2015 October; 67(2 Pt A):28-45; Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approvedmabs.php).

Adoptive cellular immunotherapy with chimeric antigen receptor (CAR) T cells has changed the treatment landscape of B-cell non-Hodgkin's lymphoma (NHL), especially for aggressive B-cell lymphomas. For instance, CD19-targeted CAR T-cells, represent the new standard of care for patients with DLBCL that are refractory to at least two prior lines of therapy. Two CAR T-cell products axicabtagene ciloleucel (axi-cel) (KTE-019) (YESCARTA™) and tisagenlecleucel (CTL019) (KYMRIAH™) have obtained US Food and Drug Administration approval for the treatment of refractory DLBCL after two lines of therapy. A third product, lisocabtagene maraleucel (liso-cel) (JCAR017), is currently being evaluated in clinical trials. Other CAR T-cells include CD20-CAR-T cells.

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al., (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two—targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof.

Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAGS pathway, of the CTLA-4 pathway and/or of the PD-1 pathway. In particular, the immune checkpoint modulator is preferably a modulator of CD40, LAGS, CTLA-4, PD-L1, PD-L2, PD-1 and/or IDO, more preferably the immune checkpoint modulator is an inhibitor of CTLA-4, PD-L1, PD-L2, PD-1, LAGS, and/or IDO or an activator of CD40, even more preferably the immune checkpoint modulator is an inhibitor of CTLA-4, PD-L1, PD-1, LAGS and/or IDO, even more preferably the immune checkpoint modulator is an inhibitor of LAGS, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab, also known as Lambrolizumab or MK-3475; Merck), Imfinzi® (Durvalumab, also known as MEDI4736; MedImmune/AstraZeneca), Tecentriq® (Atezolizumab, also known as MPDL3280A; Roche/Genentech), Pidilizumab (CT-011; CureTech), MEDI0680 (AMP-514; AstraZeneca), Bavencio® (Avelumab; Merck KGaA/Pfizer, also known as MSB-0010718C), MIH1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, Durvalumab, Tremelimumab, Avelumab, Spartalizumab, LAG525 (an anti-LAG-3 monoclonal antibody), Epacadostat (also known as INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with an appropriate antigenic peptide. Appropriate antigenic peptides may be selected by (i) selecting an appropriate tumor antigen for a certain type of cancer as known in the art and/or as described herein in Table 1B and (ii) selecting an appropriate antigenic peptide according to the invention for the selected tumor antigen, as described above, e.g. in Table 1A.

The anti-cancer therapeutic agent can also be administered in combination with the composition of the invention, either simultaneously, separately, or sequentially. Should the composition and the therapeutic agent be administered in a separate or sequential manner, those may be administered in distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

Kits-of-Parts

In a further aspect, the present invention also provides a kit-of-parts (also referred to herein as "kit") comprising at least one of the following:

the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, the cytotoxic T lymphocyte according to the present invention as described herein, and/or the pharmaceutical composition according to the present invention as described herein.

In particular, preferred embodiments of the antigenic peptide as described above also apply for such a kit according to the present invention. For example, the antigenic peptide comprised in the kit or the antigenic peptide comprised in any of the immunogenic compound, the nanoparticle, the cell, the nucleic acid, the host cell or the pharmaceutical composition comprised in the kit preferably comprises or consists of an amino acid sequence as set forth in any one of SEQ ID NOs 1 to 247 and 476-500. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, kits comprising distinct antigenic peptides according to the present invention. In particular, the kit-of-parts of the invention may comprise more than one of the above described components, e.g. 2, 3, 4, 5, 6, 7, 8, 9, or 10 distinct components. For example, the kit-of-parts according to the present invention may comprise at least two (e.g. 2, 3, 4, 5, 6, 7, 8, 9, or 10) different immunogenic compounds, at least two (e.g. 2, 3, 4, 5, 6, 7, 8, 9, or 10) different antigenic peptides, at least two (e.g. 2, 3, 4, 5, 6, 7, 8, 9, or 10) different nanoparticles, at least two (e.g. 2, 3, 4, 5, 6, 7, 8, 9, or 10) different cells, at least two (e.g. 2, 3, 4, 5, 6, 7, 8, 9, or 10) different nucleic acids, at least two (e.g. 2, 3, 4, 5, 6, 7, 8, 9, or 10) different host cells, and/or at least two (e.g. 2, 3, 4, 5, 6, 7, 8, 9, or 10) different pharmaceutical compositions. Preferably, such different components comprised by the kit-of-parts as described above differ in the antigenic peptides according to the present invention, for example one component relating to a first antigenic peptide, and one component relating to a second antigenic peptide (distinct from the first antigenic peptide). For example, the kit may comprise at least two distinct immunogenic compounds according to the present invention. For example, the kit may comprise at least two distinct antigenic peptides according to the present invention. For example, the kit may comprise at least two distinct nanoparticles according to the present invention. For example, the kit may comprise at least two distinct nucleic acids according to the present invention. For example, the kit may comprise at least two distinct cytotoxic T lymphocytes according to the present invention.

Preferred combinations of components, such as antigenic peptides, according to the present invention included in the kit correspond to the preferred combinations of components, such as antigenic peptides, according to the present invention included in the pharmaceutical composition as described above.

Accordingly, the present invention provides a kit comprising (at least one) antigenic peptide according to the present invention as described herein. Moreover, the present invention also provides a kit comprising (at least one) immunogenic compound according to the present invention as described herein. Moreover, the present invention also provides a kit comprising (at least one) nanoparticle according to the present invention as described herein. Moreover, the present invention also provides a kit comprising (at least one) cell according to the present invention as described herein. Moreover, the present invention also provides a kit comprising (at least one) nucleic acid according to the present invention as described herein. Moreover, the present invention also provides a kit comprising (at least one) host cell according to the present invention as described herein.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like.

Accordingly, the present invention provides a kit comprising at least two, preferably three distinct antigenic peptides according to the present invention as described herein (or immunogenic compounds, nanoparticles, nucleic acids, cells, etc. as described above, which differ regarding the antigenic peptide), and, optionally, a helper peptide, such as the UCP2 peptide, and/or an adjuvant, such as MONTANIDE ISA 51. Distinct antigenic peptides (or immunogenic compounds, nanoparticles, nucleic acids, cells, etc. as described above, which differ regarding the antigenic peptide) may be contained in the same or in distinct containers. For example, the kit may comprise a (single) container containing a first antigenic peptide as described herein and a second antigenic peptide as described herein. Said (single) container may additionally also comprise a helper peptide, such as UCP2. Optionally, the first and second antigenic peptide (and optionally the helper peptide) contained in the (single) container may be formulated together, e.g. in water for injection and/or Dimethyl sulfoxide (DMSO). Additionally, the kit may comprise a further container (distinct from the container containing the antigenic peptides), which contains the adjuvant, e.g. MONTANIDE ISA 51.

It is thus preferred that the kit comprises
(i) a first vial comprising one or more antigenic peptides of the invention (e.g., at least 200 or 300 µg of each antigenic peptide), and, optionally, a helper peptide, such as UCP2 (e.g., at least 200 or 300 µg of the helper peptide), optionally formulated in water for injection and dimethyl sulfoxide (DMSO); and
(ii) a second vial comprising MONTANIDE ISA 51 (e.g., at least 0.4 or 0.5 ml).

In addition, the kit may comprise one or more (e.g., 2 or 3) syringes, for example silicon- and rubber-free syringes. The kit may also comprise a connector, such as an I-connector.

Non-limiting examples of such connectors are:
the I-connector developed by Green Peptide (Japan),
the connector of reference DIDRACDLLFT from Didanorm (France),
the I-connector (ref: ODG0015ST) from Promepla (Monaco), and
the I-connector (ref: MX494) from Smiths medical (US).

The syringes are preferably suitable for MONTANIDE, i.e., silicon-free and rubber free (i.e., without any rubber tip free on the plunger), and preferably also latex-free. Non-limiting examples of such syringes are:
2 ml INKJET (Ref: 4606701V from B-Braun, Germany),
5 ml INKJET (Ref: 4606710V from B-Braun, Germany),
2 ml Norm-Ject (Ref: 4020.000VO from Henke Sass Wolf GMBH, Germany), and
5 ml Norm-Ject (Ref: 4050.000VO from Henke Sass Wolf GMBH, Germany).

For example, the kit may comprise (i) a first vial comprising at least 300 µg of an antigenic peptide of the invention (or two or three antigenic peptides, at least 300 µg of each), and optionally at least 300 µg of UCP2, formulated in water for Injection and Dimethyl sulfoxide (DMSO), (ii)

a second vial comprising at least 0.5 ml of MONTANIDE ISA 51, (iii) two silicon- and rubber-free syringes, and (iv) an I-connector.

Optionally, the kit can also comprise a vial of water for injection and/or a vial adapter. A sterile needle can also be comprised, e.g. for vaccinating the patient after obtaining the emulsion. The syringes in the kit can be, for example, 2 ml syringes.

In addition, the kit-of-parts according to the present invention may optionally contain instructions of use. Accordingly, it is preferred that the kit comprises a package insert or instruction leaflet with directions to prevent or to treat B-cell malignancy by using the immunogenic compound according to the present invention, the antigenic peptide according to the present invention, the nanoparticle according to the present invention, the cell according to the present invention, the nucleic acid according to the present invention, the host cell according to the present invention, or the pharmaceutical composition according to the present invention.

It is also preferred that, in addition to any of components as described above, the kit comprises an anti-cancer therapeutic agent as described herein.

Moreover, the present invention also provides a vaccination kit for treating, preventing and/or stabilizing B-cell malignancy, comprising the pharmaceutical composition as described herein or a vaccine as described herein and instructions for use of said pharmaceutical composition or of said vaccine in the prevention and/or treatment of B-cell malignancy.

Medical Treatment and Uses

As stated above, the composition of the invention can be particularly useful for therapeutic purposes (as medicament), notably for triggering a specific immune response towards a particular tumor antigen/protein, for example to prevent or treat B-cell malignancy (such as B-cell lymphomas) in a patient in need thereof.

In view thereof, the present invention provides
the antigenic peptide according to the present invention as described herein,
the immunogenic compound according to the present invention as described herein,
the nanoparticle according to the present invention as described herein,
the cytotoxic T lymphocyte (CTL) according to the invention as described herein,
the cell according to the present invention as described herein,
the nucleic acid according to the present invention as described herein,
the host cell according to the present invention as described herein,
the pharmaceutical composition according to the present invention as described herein,
the kit according to the present invention as described herein, or
the combination according to the present invention as described herein
for use in medicine, in particular in the prevention and/or in the treatment of a B-cell malignancy.

In particular, preferred embodiments of the antigenic peptide as described above also apply for the use according to the present invention in the prevention and/or in the treatment of a B-cell malignancy. For example, the antigenic peptide used in the prevention and/or in the treatment of B-cell malignancy or the antigenic peptide comprised in any of the immunogenic compound, the nanoparticle, the cell, the nucleic acid, the host cell or the pharmaceutical composition used in the prevention and/or in the treatment of a cancer preferably comprises or consists of an amino acid sequence as set forth in any one of SEQ ID NOs SEQ ID NOs 1 to 257 and 476-500. In some embodiments, antigenic peptides according to the present invention comprise or consist of an amino acid sequence as set forth in any one of SEQ ID NOs 1-12, 34-35, 36-39, 40, 41-64, 65-70, 476-484, 71-80, 81-87, 106-110, 485-488, 111-130, 489-493, 210-225, 494-500 and 226-257; preferably the antigenic peptide comprises or consists of an amino acid sequence as set forth in any one of SEQ ID NOs 34-35, 65-70, 476-484, 106-110, 485-488, 111-130, 489-493, 210-225, 494-500 and 226-257; more preferably the antigenic peptide comprises or consists of an amino acid sequence as set forth in any one of SEQ ID NOs 65-70, 476-484, 106-110, 485-488, 111-130, 489-493, 210-225 and 494-500. More preferably, the antigenic peptide comprises or consists of an amino acid sequence as set forth in any one of SEQ ID NOs 10, 34, 35, 39, 40, 61, 68, 70, 72, 86, 107-110, 114, 117, 119, 120, 212, 217, 220, 224, 227, 231, 477, 491 and 493. For example, antigenic peptides according to the present invention comprising or consisting of an amino acid sequence as set forth in any one of SEQ ID NOs 10, 21, 33, 35, 39, 40, 61, 65, 68, 72, 86, 110, 114 and 220 are even more preferred. For example, antigenic peptides according to the present invention comprising or consisting of an amino acid sequence as set forth in any one of SEQ ID NOs 10, 21, 33, 35, 39, 40, 110, 114 and 220 are still more preferred. For example, antigenic peptides according to the present invention comprising or consisting of an amino acid sequence as set forth in any one of SEQ ID NOs 10, 110, 114 and 220 are still more preferred. For example, antigenic peptides according to the present invention comprising or consisting of an amino acid sequence as set forth in any one of SEQ ID NOs 65, 110, 114 and 220 are still more preferred.

Also combinations thereof are preferred, namely, distinct antigenic peptides according to the present invention for use in the prevention and/or in the treatment of B-cell malignancy. In particular, more than one of the above described components may be used in the prevention and/or in the treatment of B-cell malignancy. For example, at least two different antigenic peptides, at least two different immunogenic compounds, at least two different nanoparticles, at least two different cells, at least two different nucleic acids, at least two different host cells, and/or at least two different pharmaceutical compositions may be used in the prevention and/or in the treatment of B-cell malignancy. Preferably, such different components used in the prevention and/or in the treatment of B-cell malignancy as described above differ in the antigenic peptides according to the present invention, for example one component relating to a first antigenic peptide, and one component relating to a second antigenic peptide (distinct from the first antigenic peptide). For example, at least two distinct immunogenic compounds according to the present invention may be used in the prevention and/or in the treatment of B-cell malignancy. For example, at least two distinct antigenic peptides according to the present invention may be used in the prevention and/or in the treatment of B-cell malignancy. For example, at least two distinct nanoparticles according to the present invention may be used in the prevention and/or in the treatment of B-cell malignancy. For example, at least two distinct nucleic acids according to the present invention may be used in the prevention and/or in the treatment of B-cell malignancy.

Accordingly, the present invention provides (at least one) antigenic peptide according to the present invention as described herein for use in the prevention and/or in the treatment of B-cell malignancy. Moreover, the present invention also provides (at least one) immunogenic compound according to the present invention as described herein for use in the prevention and/or in the treatment of B-cell malignancy. Moreover, the present invention also provides (at least one) nanoparticle according to the present invention as described herein for use in the prevention and/or in the treatment of B-cell malignancy. Moreover, the present invention also provides (at least one) cell according to the present invention as described herein for use in the prevention and/or in the treatment of B-cell malignancy. Moreover, the present invention also provides (at least one) nucleic acid according to the present invention as described herein for use in the prevention and/or in the treatment of B-cell malignancy. Moreover, the present invention also provides (at least one) host cell according to the present invention as described herein for use in the prevention and/or in the treatment of B-cell malignancy. Moreover, the present invention also provides (at least one) pharmaceutical composition according to the present invention as described herein for use in the prevention and/or in the treatment of B-cell malignancy. Moreover, the present invention also provides a kit according to the present invention as described herein for use in the prevention and/or in the treatment of B-cell malignancy.

Accordingly, the present invention also provides a method for preventing (reducing occurrence of) and/or treating a B-cell malignancy or initiating, enhancing or prolonging an anti-tumor-response against a B-cell malignancy in a subject in need thereof comprising administering to the subject
the antigenic peptide according to the present invention,
the immunogenic compound according to the present invention,
the nanoparticle according to the present invention,
the cell according to the present invention,
the cytotoxic T lymphocyte (CTL) according to the invention as described herein,
the nucleic acid according to the present invention,
the host cell according to the present invention,
the pharmaceutical composition according to the present invention,
the kit according to the present invention, or
the combination according to the present invention as described herein.

Preferably, the B cell malignancy to be treated include leukemia and lymphoma, e.g., acute myeloid (or myelogenous) leukemia (AML), chronic myeloid (or myelogenous) leukemia (CML), acute lymphocytic (or lymphoblastic) leukemia (ALL), B-chronic lymphocytic leukemia (BCLL), chronic lymphocytic leukemia (CLL, Richter's), hairy cell leukemia (HCL), lymphoplasmacytic lymphoma (LPC) or Waldenström's macroglobulinemia, prolymphocytic leukemia (PLL), small lymphocytic lymphoma (SLL), mantle cell lymphoma (MCL), marginal zone lymphoma (MZL), Burkitt lymphoma (BL), Hodgkin lymphoma (HL), non-Hodgkin lymphoma (NHL), anaplastic large cell lymphoma (ALCL), follicular lymphoma (FL), refractory follicular lymphoma, diffuse large B-cell lymphoma (DLBCL) and multiple myeloma (MM). In some embodiments, the B cell malignancy is selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of indolent (slow-growing) NHL, aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FLsB).

Moreover, the present invention provides a method for eliciting or improving, in a subject, an immune response against one or multiple epitopes that is dependent on CD8+ cytotoxic T cells, wherein said method comprises administering to said subject any one of:
the antigenic peptide according to the present invention,
the immunogenic compound according to the present invention,
the nanoparticle according to the present invention,
the cytotoxic T lymphocyte (CTL) according to the invention,
the cell according to the present invention,
the nucleic acid according to the present invention,
the host cell according to the present invention,
the pharmaceutical composition according to the present invention,
the kit according to the present invention, or
the combination according to the present invention as described herein.

An immune response that is dependent on CD8+ response can be determined by evaluating an inflammatory response, a pro-inflammatory cytokine response, including an increase in the expression of one or more of IFN-$\gamma$, TNF-$\alpha$ and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules, wherein said method comprises administering to said subject any one of:
the antigenic peptide according to the present invention,
the immunogenic compound according to the present invention,
the nanoparticle according to the present invention,
the cytotoxic T lymphocyte (CTL) according to the invention,
the cell according to the present invention,
the nucleic acid according to the present invention,
the host cell according to the present invention,
the pharmaceutical composition according to the present invention,
the kit according to the present invention, or
the combination according to the present invention as described herein.

A method for eliciting or improving, in a subject, an immune response against multiple epitopes as described herein, that is restricted by multiple MHC class I molecules can be determined by evaluating a cytokine response, including an increase in the expression of one or more of IFN-$\gamma$, TNF-$\alpha$ and IL-2 mRNA or protein relative to the level before administration of the compounds of the invention, after in vitro stimulation of T cells with individual peptides binding to discrete MHC class I molecules on antigen presenting cells. Restriction to MHC class I molecules can also be validated by using antigen presenting cells expressing MHC class I molecules, or by using MHC class I blocking antibodies. It can also be measured by an increase in the frequency or absolute number of antigen-specific T cells after administration of the compounds of the invention, measured by HLA-peptide multimer staining, using multimers assembled with MHC class I molecules.

Thus, in another aspect, the present invention also provides
- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein for use as a medicament.

The invention relates more particularly to a composition as defined above, for use as a vaccine for immunotherapy. Moreover,
- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein may be used as vaccine, in particular for (cancer) immunotherapy.

As used in the context of the present invention, the term "vaccine" refers to a (biological) preparation that provides innate and/or adaptive immunity, typically to a particular disease, preferably B-cell malignancy. Thus, a vaccine supports in particular an innate and/or an adaptive immune response of the immune system of a subject to be treated. For example, the antigenic peptide according to the present invention typically leads to or supports an adaptive immune response in the patient to be treated.

In the context of the present invention, the vaccine (composition) can induce a specific immune response against a tumor antigen, and is thus preferably used to prevent or treat B-cell malignancy.

Accordingly, in a preferred embodiment, the invention relates to a composition as defined above, for use in the prevention and/or treatment of cancer in a subject in need thereof. More preferably, the invention relates to the use of the composition of the invention for manufacturing a medicament to prevent or treat cancer in a subject in need thereof. In other words, the invention relates to a method for preventing or treating cancer in a subject in need thereof, comprising administering an effective amount of the composition of the invention, to said subject.

Preferably the cancer to be prevented and/or treated by
- the antigenic peptide according to the present invention,
- the immunogenic compound according to the present invention,
- the nanoparticle according to the present invention,
- the cytotoxic T lymphocyte (CTL) according to the invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein relates to the (reference) tumor antigen of the antigenic peptide as described herein. Namely, appropriate antigenic peptides may be selected by (i) selecting an appropriate tumor antigen for a certain type of cancer as known in the art and (ii) selecting an appropriate antigenic peptide according to the invention for the selected tumor antigen, as described above, e.g. in Table 1A. One skilled in the art will readily understand that an antigenic peptide of the invention can be selected based upon the nature of the B-cell malignancy to be prevented or treated, and/or on the human gene/human tumor antigen involved in said B-cell malignancy.

In general, antigenic peptides of the invention may be administered "naked" or in the form of immunogenic compounds according to the present invention, cells loaded therewith according to the present invention, nanoparticles according to the present invention, nucleic acids according to the present invention, host cells according to the present invention and/or pharmaceutical compositions according to the present invention.

In a preferred embodiment, they may be administered in the form of a micro-organism such as a gut bacterial species. Entire gut bacterial species can also be advantageous as they have the potential to trigger a greater immune response than the (poly)peptides or nucleic acids they contain. Alternatively, gut bacteria according to the invention may be in the form of probiotics, i.e. of live gut bacterium, which can thus be used as food additive thanks to the health benefits it can provide. Those can be for example lyophilized in granules, pills or capsules, or directly mixed with dairy products for consumption.

Methods of administration are well-known to the skilled person in the art. With regard to the composition of the invention, it can be directly administered into the subject, into the affected organ (i.e. local administration) or systemically (i.e. enteral or parenteral administration), or even applied ex vivo to cells derived from the subject or a human cell line which are subsequently administered to the subject, or even used in vitro to select a subpopulation of immune cells derived from the subject, which are then re-administered to the said subject. Enteral administrations include oral and rectal administrations, as well as administrations via gastric feeding tubes, duodenal feeding tubes or gastrostomy, while parenteral administrations include, among others, subcutaneous, intravenous, intramuscular, intra-arterial, intradermal, intraosseous, intracerebral, and intrathecal injections. The administration method will often depend upon the antigenic peptide(s) and/or immunogenic compound(s) present in the composition, and the type of cancer to be treated and other active agents that may be contained in said composition. For example, the administration is preferably an intramuscular or an intradermal injection if the immunogenic compound is a nucleic acid as defined above, the oral/nasal administration being particularly preferred if said nucleic acid is cloned into a viral vector. Alternatively, the administration is preferably an intramuscular, an intradermal or an oral administration if the antigenic peptide and/or immunogenic compound is a (poly)peptide as defined above or if it is loaded in/on a nanoparticle as described herein. Yet, still alternatively, the administration is preferably an oral administration if the antigenic peptide and/or immunogenic compound is delivered in the form of a gut bacterium as defined above, notably if the gut bacterium is in the form of probiotics.

The antigenic peptides, the immunogenic compounds and the nucleic acids according to the invention can further be encapsulated so as to facilitate their administration to the subject in need thereof. For example, those may be encapsulated into peptide nanocarriers (preferable if the immunogenic compound is a nucleic acid or a (poly)peptide), into virosomes (preferable if the immunogenic compound is a nucleic acid or a (poly)peptide), or into lipid-based carrier systems such as liposome-polycation-DNA complex (preferable if the immunogen is a nucleic acid or a (poly)peptide) (Trovato M, De Berardinis P. Novel antigen delivery systems. World J Virol. 2015 Aug. 12; 4(3):156-68; Saade F, Petrovsky N. Technologies for enhanced efficacy of DNA vaccines. Expert Rev Vaccines. 2012 February; 11(2):189-209; Li et al., Peptide Vaccine: Progress and Challenges. Vaccines (Basel). 2014 Jul. 2; 2(3):515-36).

The composition may also be administered more than once so as to achieve the desired effect. In a preferred embodiment, said composition is administered repeatedly, at least twice, and preferably more than twice. This can be done over an extended period of time, such as weekly, every other week, monthly, yearly, or even several years after the first administration to ensure that the subject is properly immunized.

Combination Therapy

The administration of the antigenic peptide according to the present invention, the immunogenic compound according to the present invention, the nanoparticle according to the present invention, the cell according to the present invention, the nucleic acid according to the present invention, the host cell according to the present invention, and the pharmaceutical composition according to the present invention, in particular in the methods and uses according to the invention, can be carried out alone or in combination with a co-agent useful for treating and/or preventing cancer, such as an anti-cancer therapeutic agent.

Said therapeutic agent is thus preferably capable of preventing and/or treating the same type of cancer as the one for which the antigenic peptide according to the invention is used. Particularly preferred anti-cancer therapeutic agents according to the invention include, without limitation, antibodies, CAR-T cells, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumour antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA4, B7H3, B7H4, PVR, TIGIT, GAL9, LAG-3, GITR, CD137, TIM3, VISTA, VISTA-R (Pico de Coana et al., Checkpoint blockade for cancer therapy: revitalizing a suppressed immune system. Trends Mol Med. 2015 August; 21(8):482-91; Pardoll DM1. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al. (Buqué et al., Trial Watch: Immunomodulatory monoclonal antibodies for oncological indications. Oncoimmunology. 2015 Mar. 2; 4(4):e1008814. eCollection 2015 April), Redman et al. (Redman et al., Mechanisms of action of therapeutic antibodies for cancer. Mol Immunol. 2015 October; 67(2 Pt A):28-45), and in Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Adoptive cellular immunotherapy with chimeric antigen receptor (CAR) T cells has changed the treatment landscape of B-cell non-Hodgkin's lymphoma (NHL), especially for aggressive B-cell lymphomas. For instance, CD19-targeted CAR T-cells, represent the new standard of care for patients with DLBCL that are refractory to at least two prior lines of therapy. Two CAR T-cell products axicabtagene ciloleucel (axi-cel) (KTE-019) (YESCARTA™) and tisagenlecleucel (CTL019) (KYMRIAH™) have obtained US Food and Drug Administration approval for the treatment of refractory DLBCL after two lines of therapy. A third product, lisocabtagene maraleucel (liso-cel) (JCAR017), is currently being evaluated in clinical trials. Other CAR T-cells include CD20-CAR-T cells.

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al. (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two—targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAGS pathway, of the CTLA-4 pathway and/or of the PD-1 pathway. In particular, the immune checkpoint modulator is preferably a modulator of CD40, LAGS, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; also known as Lambrolizumab or MK-3475; Merck), Imfinzi® (Durvalumab also known as MEDI4736; MedImmune/AstraZeneca), Tecentriq® (Atezolizumab also known as MPDL3280A; Roche/Genentech), Pidilizumab (CT-011; CureTech), MEDI0680 (AMP-514; AstraZeneca), Bavencio® (Avelumab; Merck KGaA/Pfizer also known as MSB-001071SC), MIH1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, MEDI4736, Tremelimumab, Avelumab, Spartalizumab, LAG525 (an anti-LAGS monoclonal antibody), Epacadostat (formerly INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention.

The anti-cancer therapeutic agent can also be administered in association with the antigenic peptide according to the present invention, the immunogenic compound according to the present invention, the nanoparticle according to the present invention, the cell according to the present invention, the nucleic acid according to the present invention, the host cell according to the present invention, or the pharmaceutical composition according to the present invention, either at about the same time or consecutively as described herein and in the same or distinct pharmaceutical forms. Thus, the invention proposes a combined use of the composition the invention and least one anti-cancer therapeutic agent as described above, for a simultaneous, separate, or sequential administration as described herein.

Furthermore, the present invention also relates to a combination of at least two distinct antigenic peptides according to the present invention, e.g. for use in the prevention and/or treatment of B-cell malignancy. Furthermore, the present invention also relates to a combination of at least two distinct immunogenic compounds according to the present invention, e.g. for use in the prevention and/or treatment of B-cell malignancy. Furthermore, the present invention also relates to a combination of at least two distinct nanoparticles according to the present invention, e.g. for use in the prevention and/or treatment of B-cell malignancy. Furthermore, the present invention also relates to a combination of at least two distinct nucleic acids according to the present invention, e.g. for use in the prevention and/or treatment of B-cell malignancy.

Thus, according to a preferred embodiment, at least two antigenic peptides according to the present invention may be administered in combination, for example in the same pharmaceutical composition. For example, at least 3 antigenic peptides, at least 4 antigenic peptides, at least 5 antigenic peptides, at least 6 antigenic peptides, at least 7 antigenic peptides, at least 8 antigenic peptides, at least 9 antigenic peptides, at least 10 antigenic peptides, at least 11 antigenic peptides, at least 12 antigenic peptides, at least 13 antigenic peptides, at least 14 antigenic peptides, at least 15 antigenic peptides, at least 20 antigenic peptides, at least 25 antigenic peptides, at least 50 antigenic peptides, at least 100 antigenic peptides are administered in combination, for example in the same pharmaceutical composition. It is within the skill of the person in the art to select the combination of antigenic peptides that is suitable for the intended purpose.

In a particularly preferred embodiment two distinct antigenic peptides according to the present invention (e.g., relating to the same type of B-cell malignancy and/or to the same reference antigen) are combined. For example,
(i) at least two distinct immunogenic compounds according to the present invention;
(ii) at least two distinct antigenic peptides according to the present invention;
(iii) at least two distinct nanoparticles according to the present invention; or
(iv) at least two distinct nucleic acids according to the present invention
may be combined.

For example, the present invention provides a combination of at least two distinct antigenic peptides according to the present invention, in particular
(i) a first antigenic peptide according to the present invention, and
(ii) a second antigenic peptide according to the present invention (distinct from the first) preferably for use in the prevention and/or treatment of B-cell malignancy.

For example, the present invention provides a combination of at least two distinct immunogenic compounds according to the present invention, in particular
(i) an immunogenic compound according to the present invention comprising a first antigenic peptide according to the present invention, and
(ii) an immunogenic compound according to the present invention comprising a second antigenic peptide according to the present invention (distinct from the first)
preferably for use in the prevention and/or treatment of B-cell malignancy.

For example, the present invention provides a combination of at least two distinct nanoparticles according to the present invention, in particular
(i) a nanoparticle according to the present invention comprising a first antigenic peptide according to the present invention, and
(ii) a nanoparticle according to the present invention comprising a second antigenic peptide according to the present invention (distinct from the first)
preferably for use in the prevention and/or treatment of B-cell malignancy.

For example, the present invention provides a combination of at least two distinct nucleic acids according to the present invention, in particular
(i) a nucleic acid according to the present invention comprising a polynucleotide encoding a first antigenic peptide according to the present invention and
(ii) a nucleic acid according to the present invention comprising a polynucleotide encoding a second antigenic peptide according to the present invention (distinct from the first)
preferably for use in the prevention and/or treatment of B-cell malignancy.

For example, the present invention provides a combination of at least two distinct cytotoxic T lymphocytes according to the present invention, in particular
(i) a cytotoxic T lymphocyte according to the present invention specific for a first antigenic peptide according to the present invention and
(ii) a cytotoxic T lymphocyte according to the present invention specific for a second antigenic peptide according to the present invention (distinct from the first)
preferably for use in the prevention and/or treatment of B-cell malignancy.

In the combinations according to the present invention, such combinations of components, such as antigenic peptides, according to the present invention are preferred, which correspond to the preferred combinations of components, such as antigenic peptides, according to the present invention included in the pharmaceutical composition as described above.

Moreover, the antigenic peptide according to the present invention may also be combined with the corresponding (human) tumor antigen epitope (as described above regarding the peptide "families"). Thereby, selection of T-cell clones, which are very efficient against the tumor, is obtained/supported. In particular, the antigenic peptide according to the present invention and the corresponding (human) tumor antigen epitope may be co-administered. Such co-administration may be at about the same time (simultaneously) or consecutively, whereby in consecutive administration it is preferred that the antigenic peptide according to the present invention is administered first and the corresponding (human) tumor antigen epitope is administered thereafter. In particular, the antigenic peptide according to the present invention may be administered first, and the corresponding (human) tumor antigen epitope may be used as (re)boost.

For example, the antigenic peptide according to SEQ ID NO: 10 may be combined with the reference peptide according to SEQ ID NO: 258. In another example, the antigenic peptide according to SEQ ID NO: 110 may be combined with the reference peptide according to SEQ ID NO: 270. In another example, the antigenic peptide according to SEQ ID NO: 114 may be combined with the reference peptide according to SEQ ID NO: 271. In another example, the antigenic peptide according to SEQ ID NO: 220 may be combined with the reference peptide according to SEQ ID NO: 279.

The peptides, which are to be combined, such as (a) the antigenic peptide according to the present invention and the corresponding (human) tumor antigen epitope or (b) two distinct antigenic peptides according to the present invention, may be administered

- in the same immunogenic compound according to the present invention or in distinct immunogenic compounds according to the present invention,
- (loaded) in the same nanoparticle according to the present invention or in distinct nanoparticles according to the present invention,
- (loaded) in the same cell according to the present invention or in distinct cells according to the present invention,
- (encoded by) the same nucleic acid according to the present invention or by distinct nucleic acids according to the present invention,
- (expressed by) the same host cell according to the present invention or by distinct host cells according to the present invention, or
- (comprised) in the same pharmaceutical composition according to the present invention or in distinct pharmaceutical composition according to the present invention.

In general, the expression "two distinct components" in the context of a combination, e.g. for use according to the present invention (a combination therapy), is defined as above (in the context of the pharmaceutical composition). In particular, it refers to (1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the pharmaceutical composition according to the present invention as described herein; and (2) a second component (which is distinct from the first component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct pharmaceutical composition according to the present invention as described herein, or one or more (fragments of) human tumor antigens in any form ("naked", as immunogenic compound as described herein, as nanoparticle as described herein, as (host) cell as described herein, as nucleic acid as described herein or as pharmaceutical composition as described herein).

Accordingly, the "two distinct components", as referred to herein in the context of a combination for use according to the present invention (a combination therapy), are preferably active components in the context of the disease (B-cell malignancy) to be prevented and/or treated. In other words, each of the at least two distinct components may also be useful for preventing and/or treating said cancer, if administered separately (not in combination as described herein)—although the combination (i.e. combined administration) typically potentiates their preventive and/or therapeutic effect (such as the immune response), in particular in a synergistic manner.

Accordingly, the present invention also provides the combination of (at least) two distinct antigenic peptides according to the present invention as described herein. In this context, the (at least) two distinct antigenic peptides may be in any form, e.g., "naked", comprised in immunogenic compounds, nanoparticles, (pharmaceutical) compositions or cells loaded therewith, or encoded by nucleic acids (e.g., vectors). Accordingly, the (at least) two distinct antigenic peptides may be comprised in (at least) two distinct components (to be combined). In a preferred embodiment, the at least two distinct components of the combination according to the present invention are at least distinct antigenic peptides according to the present invention (in any form, e.g. comprised in immunogenic compounds, nanoparticles, cells, pharmaceutical compositions, encoded by the nucleic acids, etc.).

Preferably, the at least two distinct components of the combination for use according to the present invention relate to the same type of cancer, for example to the same or distinct antigens associated with this cancer and/or to the same or distinct (reference) epitopes within an antigen associated with this cancer. More preferably, the at least two distinct components relate to the same tumor antigen.

In certain embodiments, the at least two distinct components of the combination for use according to the present invention are comprised in the same or distinct compositions. In certain embodiments, the at least two distinct components of the combination for use according to the present invention are administered via the same or distinct routes of administration. In certain embodiments, the at least two distinct components of the combination for use according to the present invention are administered at about the same time (simultaneously) or consecutively.

Preferably, the at least two distinct components of the combination for use according to the present invention are administered at about the same time. In more general, it is preferred that the first component is administered at about the same time as the second component, wherein the at least two distinct components of the combination for use according to the present invention are preferably administered in the same form (i.e., in the same type of formulation, e.g., as nanoparticles, as pharmaceutical compositions, etc.).

"At about the same time", as used herein, means in particular simultaneous administration or that directly after administration of the first component, the second component is administered or directly after administration of the second component, the first component is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of the first component and of the second component overlap or if, for example, one component is administered over a longer period of time, such as 30 min, 1 h, 2 h or even more, e.g. by infusion, and the other component is administered at some time during such a long period. Administration of the first component and of the second component at about the same time is in particular preferred if different routes of administration and/or different administration sites are used.

It is also preferred that the at least two distinct components of the combination for use according to the present invention are administered consecutively. In more general, it is preferred that the first component and the second component are administered consecutively, wherein the at least two distinct components of the combination for use according to the present invention are preferably administered in the same form (i.e., in the same type of formulation, e.g., as nanoparticles, as pharmaceutical compositions, etc.).

This means that the first component is administered before or after the second component. In consecutive administration, the time between administration of the first component and administration of the second component is preferably no more than one week, more preferably no more than 3 days, even more preferably no more than 2 days and most preferably no more than 24 h. It is particularly preferred that the first component and the second component are administered at the same day with the time between administration of the first component and administration of the second component being preferably no more than 6 hours, more preferably no more than 3 hours, even more preferably no more than 2 hours and most preferably no more than 1 h.

Preferably, the first component and the second component are administered via the same route of administration. In more general, it is preferred that the first component and the second component are administered via the same route of administration, wherein the at least two distinct components of the combination for use according to the present invention are preferably administered in the same form (i.e., in the same type of formulation, e.g., as nanoparticles, as pharmaceutical compositions, etc.).

It is also preferred that the at least two distinct components of the combination for use according to the present invention are administered via distinct routes of administration. In more general, it is preferred that the first component and the second component are administered via distinct routes of administration, wherein the at least two distinct components of the combination for use according to the present invention are preferably administered in the same form (i.e., in the same type of formulation, e.g., as nanoparticles, as pharmaceutical compositions, etc.).

Preferably, the at least two distinct components of the combination for use according to the present invention are comprised in the same composition. In more general, it is preferred that the first component and the second component are comprised in the same composition, wherein the at least two distinct components of the combination for use according to the present invention are preferably administered in the same form (i.e., in the same type of formulation, e.g., as nanoparticles, etc.).

It is also preferred that the at least two distinct components of the combination for use according to the present invention are comprised in distinct compositions. In more general, it is preferred that the first component and the second component are comprised in distinct compositions, wherein the at least two distinct components of the combination for use according to the present invention are preferably administered in the same form (i.e., in the same type of formulation, e.g., as nanoparticles, etc.).

In particular, the present invention provides a pharmaceutical composition comprising a first antigenic peptide according to the present invention, which comprises or consists of a sequence variant of a fragment of the human tumor antigen.

In particular, the present invention provides a combination, e.g. for use in the prevention and/or treatment of B-cell malignancy, comprising a first antigenic peptide according to the present invention, which comprises or consists of a microbiota sequence variant of a fragment of the human tumor antigen CD22, and a second antigenic peptide according to the present invention, which comprises or consists of a sequence variant of a fragment of the human tumor antigen TNFRSF13C. Preferably, the first antigenic peptide comprises or consists of a sequence variant of the CD22 fragment (human reference peptide) "WVFEHPETL" (SEQ ID NO: 270), such as an antigenic peptide comprising or consisting of an amino acid sequence as set forth in SEQ ID NO: 106-110, 316 and 387-390, and the second antigenic peptide comprises or consists of a sequence variant of the TNFRSF13C fragment (human reference peptide) "LLFGAPALL" (SEQ ID NO: 279), such as an antigenic peptide comprising or consisting of an amino acid sequence as set forth in SEQ ID NO: 220, 325 and 450. More preferably, the first antigenic peptide comprises or consists of an amino acid sequence as set forth in SEQ ID NO: 110, 387 and 390 and the second antigenic peptide comprises or consists of an amino acid sequence as set forth in SEQ ID NO: 220, and 450. Even more preferably, the pharmaceutical composition comprises an antigenic peptide comprising or consisting of SEQ ID NO: 110 and an antigenic peptide comprising or consisting of SEQ ID NO: 220.

More preferably, the combination according to the present invention (e.g. for use in the prevention and/or treatment of B-cell malignancy) comprises at least three distinct components as described above, in particular at least three distinct antigenic peptides according to the present invention. The above description regarding the combination of two distinct components applies accordingly for three distinct components.

Most preferably, the combination according to the present invention (e.g. for use in the prevention and/or treatment of B-cell malignancy) comprises at least four distinct components as described above, in particular at least four distinct antigenic peptides according to the present invention. The above description regarding the combination of two distinct components applies accordingly for four distinct components.

It is understood that the combination, e.g. for use in the prevention and/or treatment of B-cell malignancy, may also contain—instead of the above-described preferred combinations of antigenic peptides—a respective combination of immunogenic compounds of the invention, a respective combination of nanoparticles of the invention or a respective combination of nucleic acids of the invention.

BRIEF DESCRIPTION OF THE FIGURES

In the following a brief description of the appended figures will be given. The figures are intended to illustrate the present invention in more detail. However, they are not intended to limit the subject matter of the invention in any way.

EXAMPLES

Figure 1:
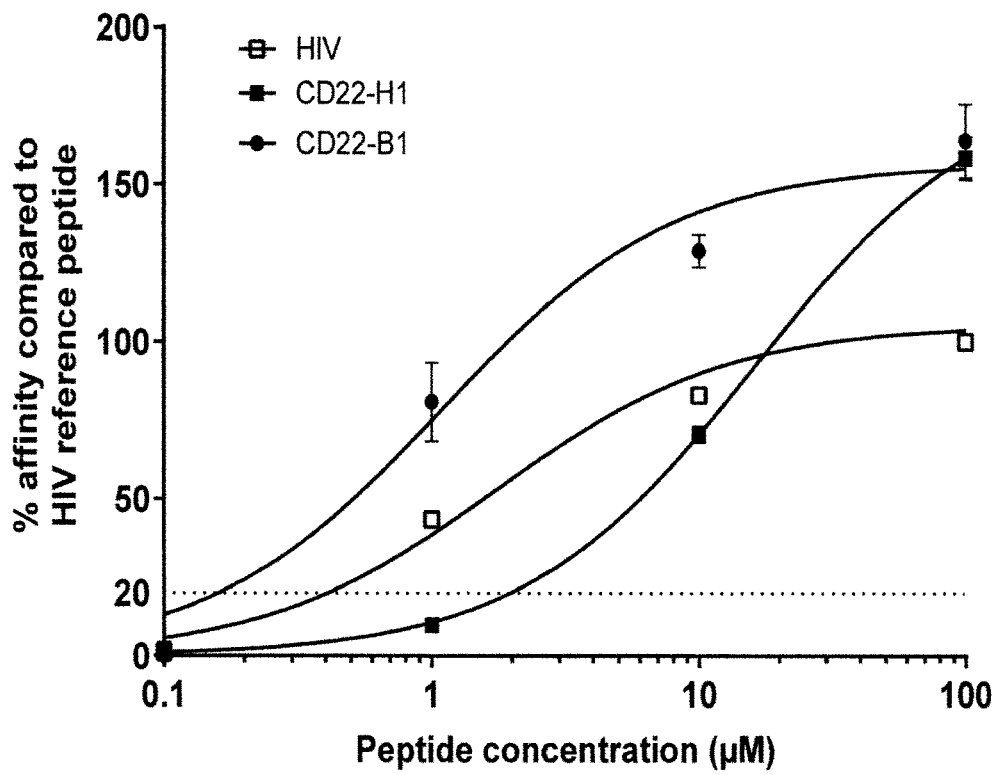
FIG. 1: shows for Example 1 in vitro affinity for the antigenic peptide CD22-B1 in comparison to the corresponding human CD22 epitope CD22-H1.
Figure 2:
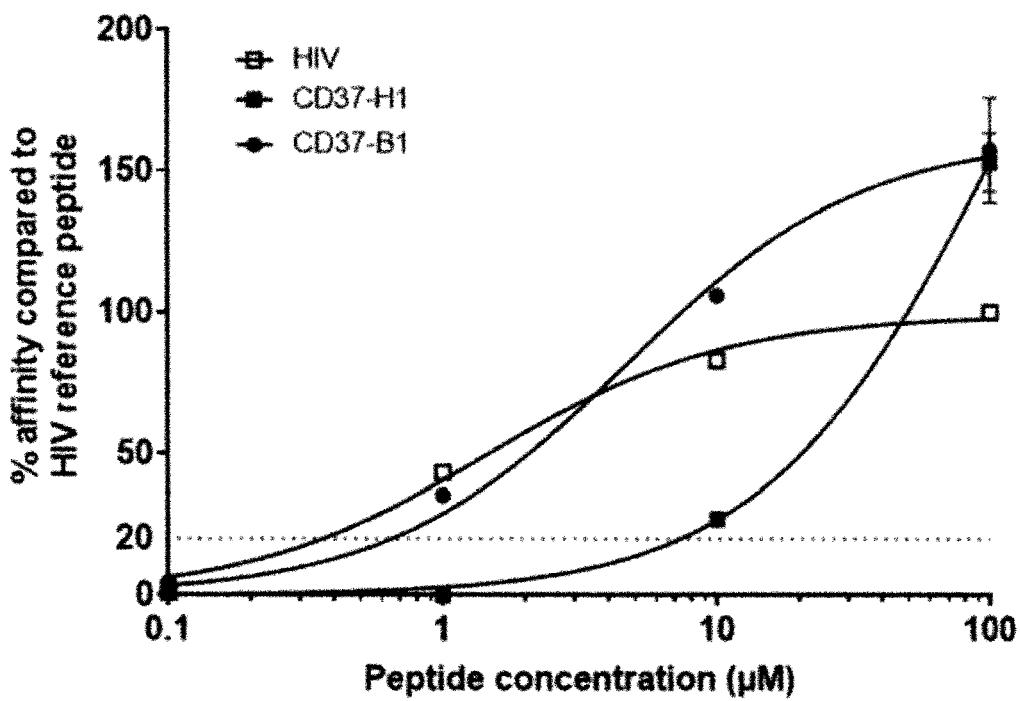
FIG. 2: shows for Example 1 in vitro affinity for the antigenic peptide CD37-B1 in comparison to the corresponding human CD37 epitope CD37-H1.
Figure 3:
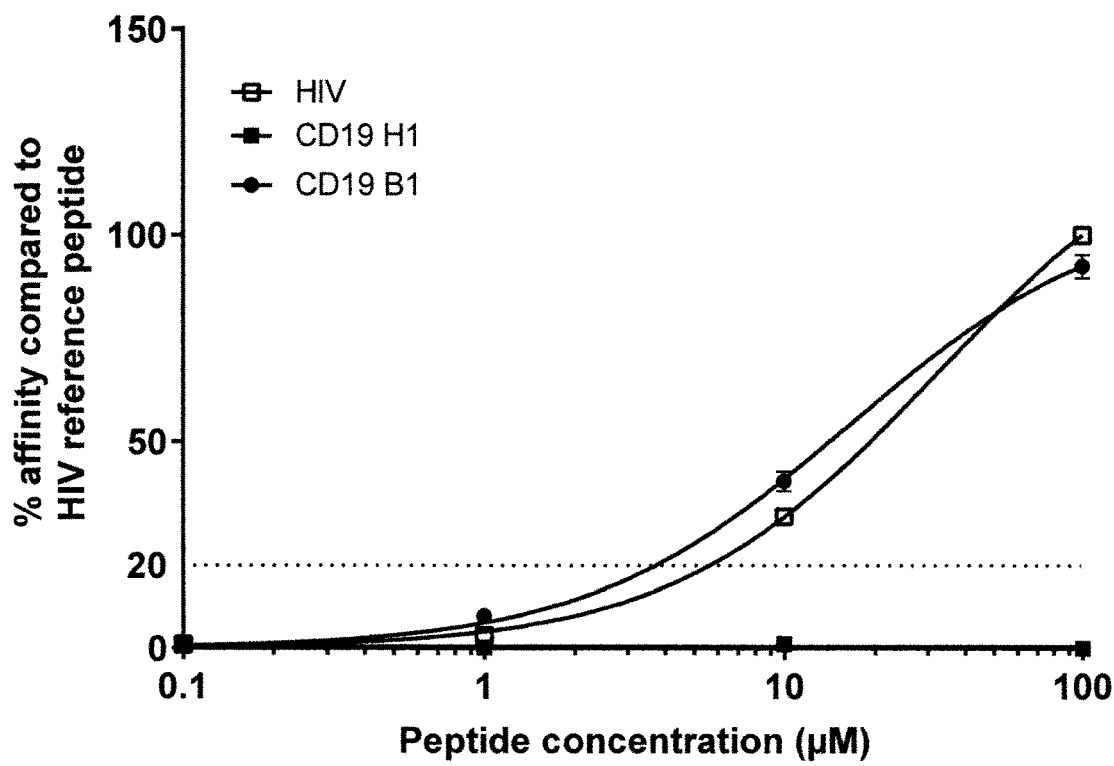
FIG. 3: shows for Example 1 in vitro affinity for the antigenic peptide CD19-B1 in comparison to the corresponding human CD19 epitope CD19-H1.
Figure 4:
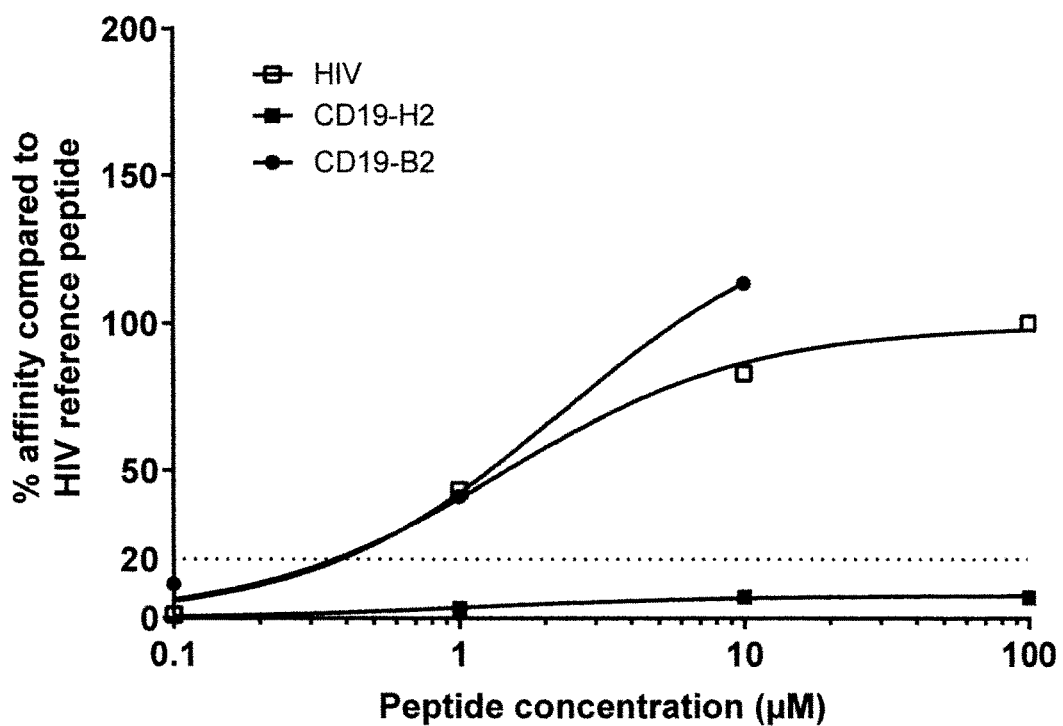
FIG. 4: shows for Example 1 in vitro affinity for the antigenic peptide CD19-B2 in comparison to the corresponding human CD19 epitope CD19-H2.
Figure 5:
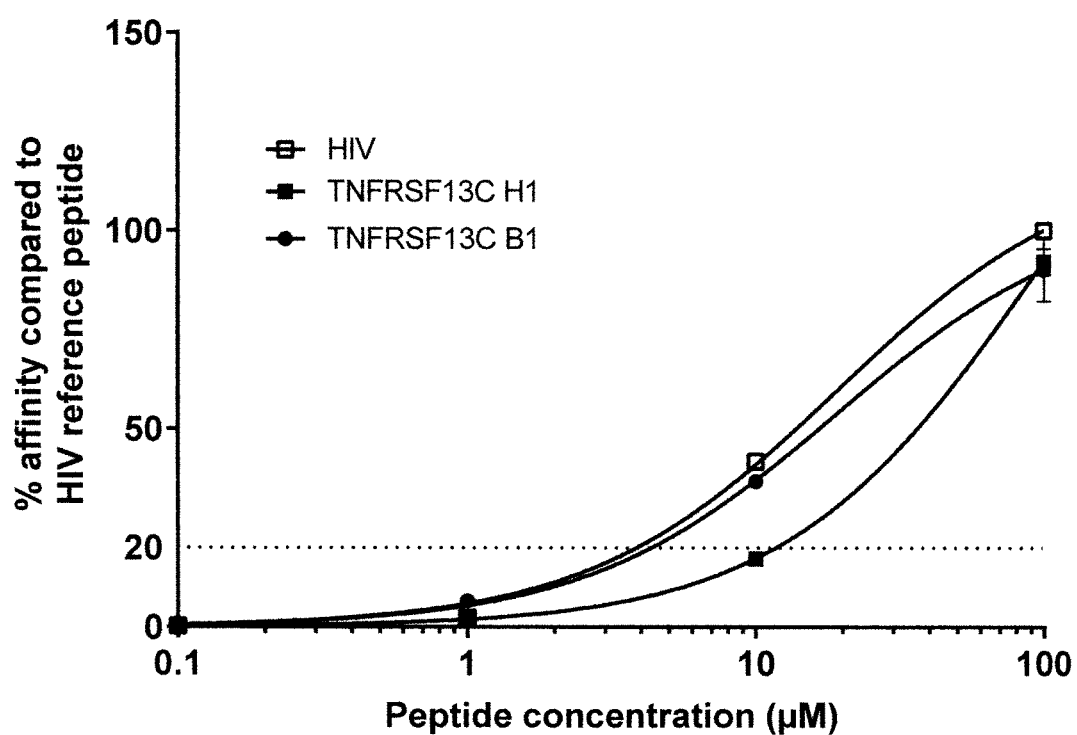
FIG. 5: shows for Example 1 in vitro affinity for the antigenic peptide TNFRSF13C-B1 in comparison to the corresponding human TNFRSF13C epitope TNFRSF13C-H1.
Figure 6:
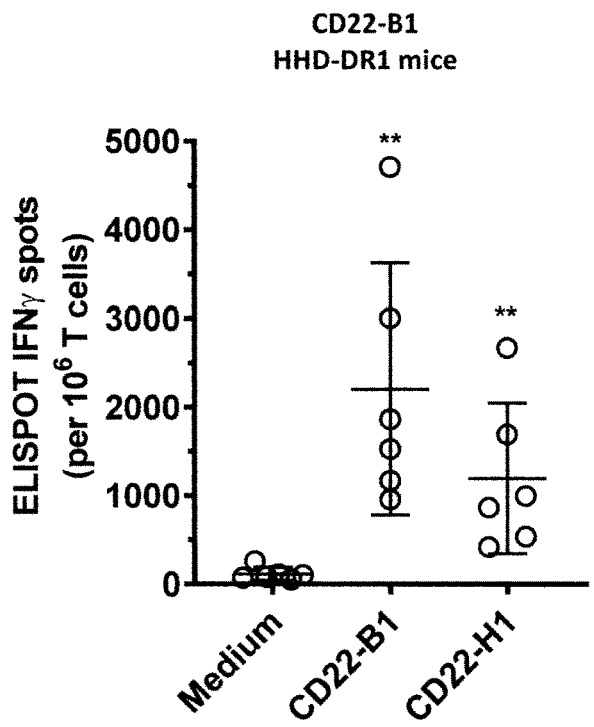
FIG. 6: shows for Example 2 ELISPOT results for HHD DR1 HLA-A2 transgenic mice vaccinated with the antigenic peptide CD22-B1 as indicated in the figure and cross-reactivity with the human corresponding peptide CD22-H1. The data were provided as a number of spots per $1 \cdot 10^6$ total T cells.
Figure 7:
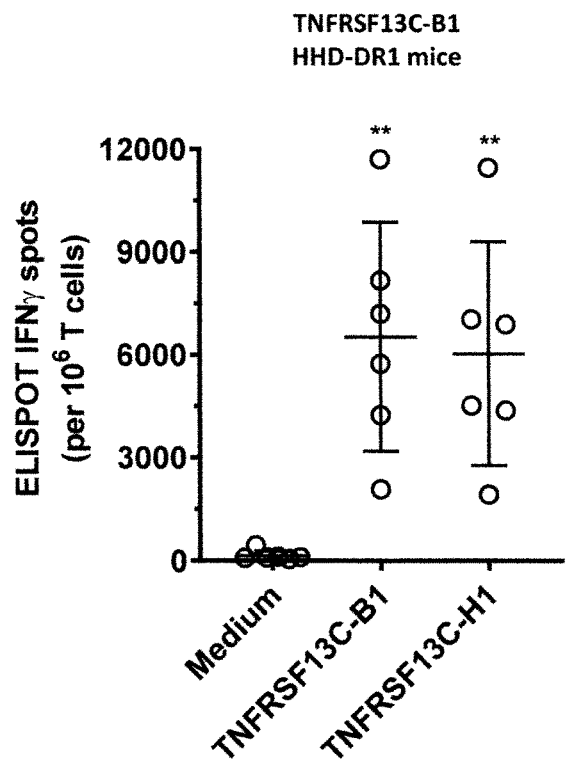
FIG. 7: shows for Example 2 ELISPOT results for HHD DR1 HLA-A2 transgenic mice vaccinated with the antigenic peptide TNFRSF13C-B1 as indicated in the figure and cross-reactivity with the human corresponding peptide TNFRSF13C-H1. The data were provided as a number of spots per $1 \cdot 10^6$ total T cells.
Figure 8:
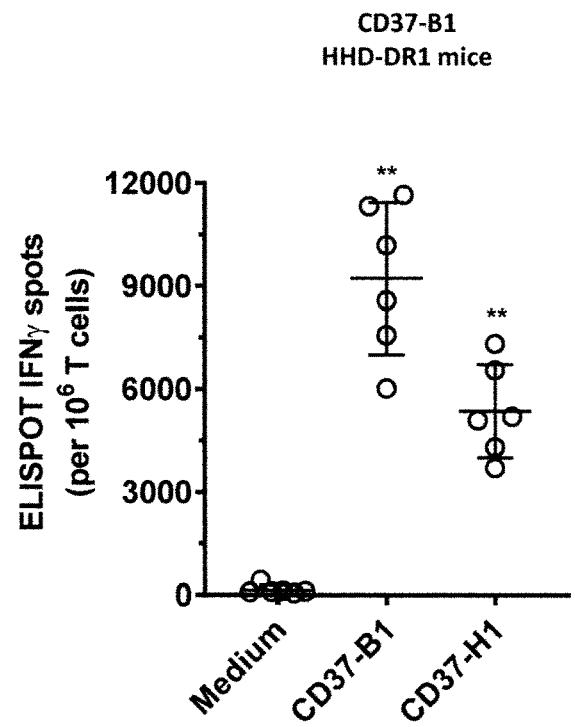
FIG. 8: shows for Example 2 ELISPOT results for HHD DR1 HLA-A2 transgenic mice vaccinated with the antigenic peptide CD37-B1 as indicated in the figure and cross-reactivity with the human corresponding peptide CD37-H1. The data were provided as a number of spots per $1 \cdot 10^6$ total T cells.
Figure 9:
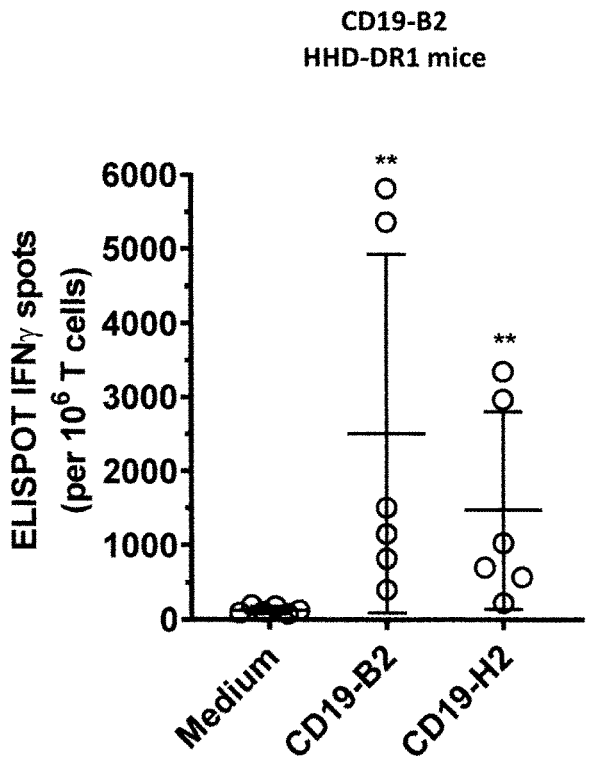
FIG. 9: shows for Example 2 ELISPOT results for HHD DR1 HLA-A2 transgenic mice vaccinated with the antigenic peptide CD19-B2 as indicated in the figure and cross-reactivity with the human corresponding peptide CD19-H2. The data were provided as a number of spots per $1 \cdot 10^6$ total T cells.
Figure 10:
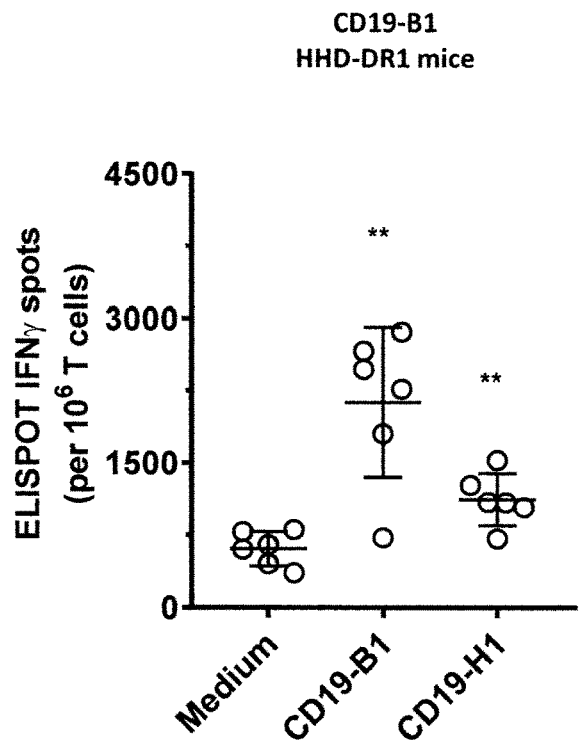
FIG. 10: shows for Example 2 ELISPOT results for HHD DR1 HLA-A2 transgenic mice vaccinated with the antigenic peptide CD19-B1 as indicated in the figure and cross-reactivity with the human corresponding peptide CD19-H1. The data were provided as a number of spots per $1 \cdot 10^6$ total T cells.

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Antigenic Peptides have Superior Affinity to the HLA-A*0201 Allele

Next, binding affinity of various selected antigenic peptides and of the corresponding fragments of human tumor antigens (human reference peptides) to the HLA-A*0201 allele was confirmed in vitro. Namely, the antigenic peptide of sequence SEQ ID NO: 110 («YIFEHPELL» also referred herein as CD22-B1) was compared to the corresponding reference human peptides derived from CD22 («WVFEHPETL», SEQ ID NO: 270, also referred herein as CD22-H1). Moreover, the antigenic peptide of sequence SEQ ID NO: 109 («YVFEHPELL» also referred herein as CD22-B11) was compared to the corresponding reference human peptide derived from CD22 («WVFEHPETL», SEQ ID NO: 270, also referred herein as CD22-H1). Moreover, the antigenic peptide of sequence SEQ ID NO: 114 («FLAFVPLQL» also referred herein as CD37-B1) was compared to the corresponding reference human peptide derived from CD37 («GLAFVPLQI», SEQ ID NO: 271, also referred herein as CD37-H1). Moreover, the antigenic peptide of sequence SEQ ID NO: 117 («GMAFVPLLL» also referred herein as CD37-B11) was compared to the corresponding reference human peptide derived from CD37 («GLAFVPLQI», SEQ ID NO: 271, also referred herein as CD37-H1). Moreover, the antigenic peptide of sequence SEQ ID NO: 34 («LLVGILHLV» also referred herein as CD19-B1) was compared to the corresponding reference human peptide derived from CD19 («SLVGILHLQ», SEQ ID NO: 260, also referred herein as CD19-H1). Moreover, the antigenic peptide of sequence SEQ ID NO: 10 («TLLFLTPML» also referred herein as CD19-B2) was compared to the corresponding reference human peptide derived from CD19 («FLLFLTPME», SEQ ID NO: 258, also referred herein as CD19-H2). Moreover, the antigenic peptide of sequence SEQ ID NO: 39 («YLAYLIFEL» also referred herein as CD19-B6) was compared to the corresponding reference human peptide derived from CD19 («TLAYLIFCL», SEQ ID NO: 261, also referred herein as CD19-H6). Moreover, the antigenic peptide of sequence SEQ ID NO: 40 («LQMGGFYLL» also referred herein as CD19-B7) was compared to the corresponding reference human peptide derived from CD19 («QQMGGFYLC», SEQ ID NO: 262, also referred herein as CD19-H7). Moreover, the antigenic peptide of sequence SEQ ID NO: 220 («LMFGAPALV» also referred herein as TNFRSF13C-B1) was compared to the corresponding reference human peptide derived from TNFRSF13C («LLFGAPALL», SEQ ID NO: 279, also referred herein as TNFRSF13C-H1). Moreover, the antigenic peptide of sequence SEQ ID NO: 231 («ILPGLLFGL» also referred herein as TNFRSF13C-B31) was compared to the corresponding reference human peptide derived from TNFRSF13C («PLPGLLFGA», SEQ ID NO: 280, also referred herein as TNFRSF13C-H3). Moreover, the antigenic peptide of sequence SEQ ID NO: 227 («FMPGLLFGA» also referred herein as TNFRSF13C-B33) was compared to the corresponding reference human peptide derived from TNFRSF13C («PLPGLLFGA», SEQ ID NO: 280, also referred herein as TNFRSF13C-H3). Moreover, the antigenic peptide of sequence SEQ ID NO: 61 («YILGGLLMV» also referred herein as MS4A1-B12) was compared to the corresponding reference human peptide derived from MS4A1 (also known as CD20) («IALGGLLMI», SEQ ID NO: 263, also referred herein as MS4A1-H1). Moreover, the antigenic peptide of sequence SEQ ID NO: 72 («ILIPAGIYL» also referred herein as MS4A1-B3) was compared to the corresponding reference human peptide derived from MS4A1 (also known as CD20) («LMIPAGIYA», SEQ ID NO: 265, also referred herein as MS4A1-H3). Moreover, the antigenic peptide of sequence SEQ ID NO: 65 («AMNSLSLYI» also referred herein as MS4A1-B4) was compared to the corresponding reference human peptide derived from MS4A1 (also known as CD20) («IMNSLSLFA», SEQ ID NO: 264, also referred herein as MS4A1-H4). Moreover, the antigenic peptide of sequence SEQ ID NO: 86 («YLFLGILSL» also referred herein as MS4A1-B5) was compared to the corresponding reference human peptide derived from MS4A1 (also known as CD20) («SLFLGILSV», SEQ ID NO: 266, also referred herein as MS4A1-H5).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30(12):3411-21). Affinity measurement of the peptides is achieved with the human tumoral cell T2 which expresses the HLA-A*0201 molecule, but which is TAP ½ negative and incapable of presenting endogenous peptides.

T2 cells (5.104 cells per well) are incubated with decreasing concentrations of peptides from 100 µM to 0.1 µM (4 points: 100 µM, 10 µM, 1 µM, 0.1 µM) in serum-free medium (TexMacs) supplemented with 100 ng/µl of β2 Microglobulin at 37° C. for 16 hours. Cells are then washed two times and marked with the anti-HLA-A2 antibody coupled to PE (clone BB7.2, BD Pharmagen).

The analysis is achieved by FACS (Macsquant analyzer 10-Miltenyi).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 µM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

The mean relative fluorescence intensity values (data are normalized to the mean fluorescence of HIV peptide, i.e. a value of 100 is equal to the best binding observed with HIV peptide) of T2 cells obtained for the various concentrations of each peptide are shown in Table 2 below:

TABLE 2

| Peptide | | | | | |
|---|---|---|---|---|---|
| Name | SEQ ID NO. | 100 | 10 | 1 | 0.1 |
| CD22-B1 | 110 | 164 | 123 | 81 | 0 |
| CD22-B11 | 109 | 140.7 | 123.8 | 60.5 | 6.4 |
| CD22-H1 | 270 | 158 | 71 | 10 | 2 |
| CD37-B1 | 114 | 157 | 106 | 35 | 5 |
| CD37-B11 | 117 | 57.8 | 48.9 | 1.6 | 0.0 |
| CD37-H1 | 271 | 153 | 27 | 0 | 2 |
| CD19-B1 | 34 | 93 | 40 | 8 | ND |
| CD19-B11 | 35 | 108.5 | 30.5 | 5.2 | 0 |
| CD19-H1 | 260 | 0 | 1 | 0 | 1 |
| CD19-B2 | 10 | ND | 114 | 41 | 12 |
| CD19-H2 | 258 | 7 | 7 | 3 | ND |
| CD19-B6 | 39 | ND | 52.5 | 5.4 | 0 |
| CD19-H6 | 261 | ND | 39.6 | 4.1 | 0 |

TABLE 2-continued

| Peptide | | | | | |
|---|---|---|---|---|---|
| Name | SEQ ID NO. | 100 | 10 | 1 | 0.1 |
| CD19-B7 | 40 | 31.8 | 4.5 | 4.8 | 6 |
| CD19-H7 | 262 | 9.3 | 2 | 0.1 | 0 |
| TNFRSF13C-B1 | 220 | 90 | 37 | 7 | 1 |
| TNFRSF13C-H1 | 279 | 92 | 17 | 2 | 0 |
| TNFRSF13C-B31 | 231 | 104.3 | 71.9 | 1.5 | 0 |
| TNFRSF13C-B33 | 227 | 99.6 | 15.5 | 1.3 | 0 |
| TNFRSF13C-H3 | 280 | 8.4 | 0 | 0 | 0 |
| MS4A1-B12 | 61 | 42 | 7.6 | 1.1 | 1.2 |
| MS4A1-H1 | 263 | ND | 1.9 | 0.7 | 0 |
| MS4A1-B3 | 72 | 88.8 | 87.8 | 17.8 | 1.9 |
| MS4A1-H3 | 265 | 92.6 | 35.7 | 0.9 | 0 |
| MS4A1-B4 | 65 | 115.2 | 13.1 | 1.9 | 0.5 |
| MS4A1-H4 | 264 | 13.4 | 2.6 | 0.3 | 0 |
| MS4A1-B5 | 86 | ND | 29.8 | 0.2 | 0 |
| MS4A1-H5 | 266 | ND | 6.5 | 1.8 | 0 |

Table 3 below summarizes for each tested peptide the concentration required to induce 20% of HLA-A2 expression and the in vitro binding affinity (* normalized against HIV-pol concentration of peptide inducing 20% of HLA-A2 expression performed during the same experiment).

TABLE 3

ND-Undeterminable

| Peptide | SEQ ID NO | Concentration of peptide that induces 20% of HLA-A2 expression (µM) | In vitro binding affinity* |
|---|---|---|---|
| CD22-B1 | 110 | 0.16 | 0.4 |
| CD22-B11 | 109 | 0.2 | 0.5 |
| CD22-H1 | 270 | 1.97 | 5.3 |
| CD37-B1 | 114 | 0.65 | 1.6 |
| CD37-B11 | 117 | 2.30 | 3 |
| CD37-H1 | 271 | 7.35 | 17.5 |
| CD19-B1 | 34 | 3.7 | 0.7 |
| CD19-B11 | 35 | 5.97 | 0.8 |
| CD19-H1 | 260 | ND | ND |
| CD19-B2 | 10 | 0.38 | 1 |
| CD19-H2 | 258 | ND | ND |
| CD19-B6 | 39 | 3.76 | 0.4 |
| CD19-H6 | 261 | 4.98 | 0.5 |
| CD19-B7 | 40 | 49.63 | 6.8 |
| CD19-H7 | 262 | >100 | ND |
| TNFRSF13C-B1 | 220 | 4.35 | 1.1 |
| TNFRSF13C-H1 | 279 | 11.76 | 3.0 |
| TNFRSF13C-B31 | 231 | 1.60 | 0.40 |
| TNFRSF13C-B33 | 227 | 13.20 | 3.50 |
| TNFRSF13C-H3 | 280 | ND | ND |
| MS4A1-B12 | 61 | 31.20 | 3.50 |
| MS4A1-H1 | 263 | ND | ND |
| MS4A1-B3 | 72 | 0.70 | 0.10 |
| MS4A1-H3 | 265 | 4.83 | 0.50 |
| MS4A1-B4 | 65 | 12.3 | 2.1 |
| MS4A1-B41 | 68 | 2.45 | 0.30 |
| MS4A1-H4 | 264 | >100 | ND |
| MS4A1-B5 | 86 | 6.77 | 0.70 |
| MS4A1-H5 | 266 | ND | ND |

Figure 14:
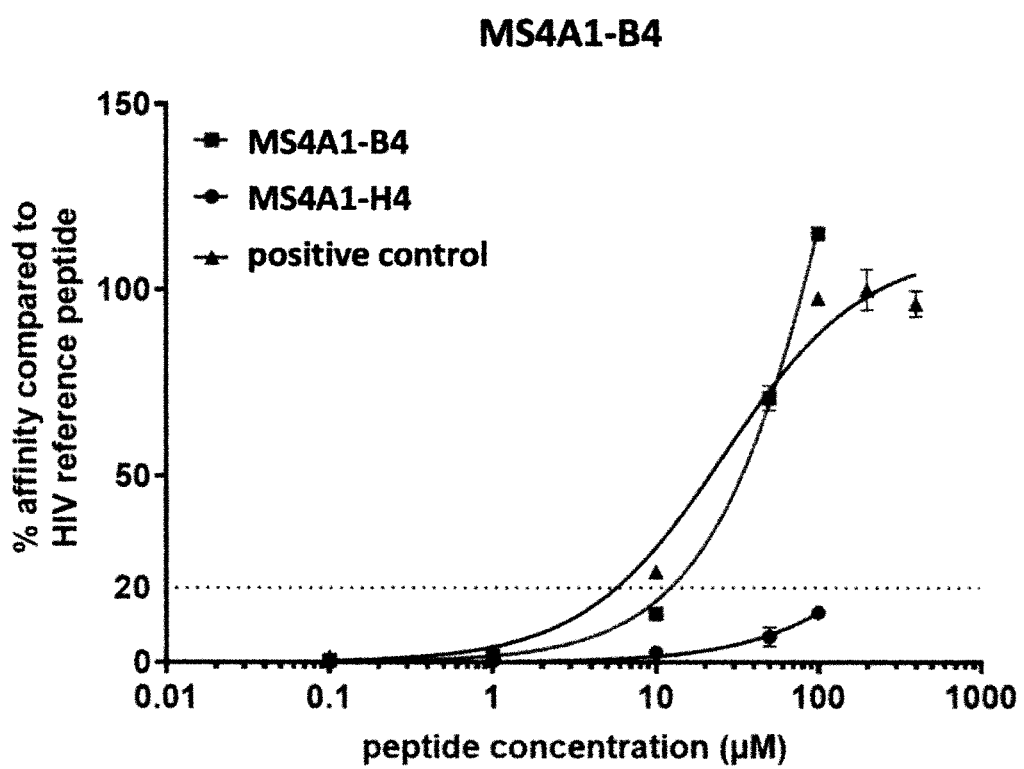
FIG. 14: shows for Example 1 in vitro affinity for the antigenic peptide MS4A1-B4 in comparison to the corresponding human MS4A1 epitope MS4A1-H4.

In addition, FIGS. 1-5 and 14 illustrate the results for selected examples, namely for the antigenic peptide CD22-B1 in comparison to the corresponding human CD22 fragment CD22-H1 (Figure i), for the antigenic peptide CD37-B1, in comparison to the corresponding human CD37 fragment CD37-H1 (FIG. 2), for the antigenic peptide CD19-B31 in comparison to the corresponding human CD19 fragment CD19-H1 (FIG. 3), for the antigenic peptide CD19-B32 in comparison to the corresponding human CD19 fragment CD19-H2 (FIG. 4), for the antigenic peptide TNFRSF13C-B1 in comparison to the corresponding human TNFRSF13C fragment TNFRSF13C-H1 (FIG. 5) and the antigenic peptide MS4A1-B4 in comparison to the corresponding human MS4A1 fragment MS4A1-B4 (FIG. 14).

In summary, the results show that the antigenic peptides according to the present invention show at least similar binding affinity to HLA-A*0201 as the corresponding human tumor antigen fragments. In most cases, the binding affinity observed for the antigenic peptides according to the present invention was stronger than that of the corresponding human epitopes. Without being bound to any theory it is assumed that such a strong binding affinity of the antigenic peptides according to the present invention reflects their ability to raise an immune response (i.e., their immunogenicity).

Example 2: Immunogenicity of CD22-B1, CD19B1, CD19-B2, CD37B1, TNFRSF13C-B1 and MS4A1-B4 in HLA-A2 Transgenic Mice and Cross-Reactivity with the Corresponding Human Peptide A. Materials and Methods
A.1 Mouse Model
Briefly, HLA-A2 HHD-DR1 humanized mice (C57BL/6JB2mtm1UncIAb-/-Tg(HLA-DRA, HLA-DRB1*0101)#GjhTg(HLA-A/H2-D/B2M)1Bpe) or HHD-DR3 humanized mice (C57BL/6JB2mtm1UncIAb-/-Tg(HLA-DRA, HLA-DRB1*0301)#GjhTg(HLA-A/H2-D/B2M)1Bpe) were assigned randomly (based on mouse sex and age) to experimental groups, wherein each group was immunized with a specific vaccination peptide (vacc-pAg) combined to a common helper peptide (h-pAg UCP2; sequence: KSVWSKLQSIGIRQH; SEQ ID NO: 475; for HHD DR1 mice or h-pAg DR3; sequence MAKTIAYDEEARRGLERGLN; SEQ ID n° 473; for HHD DR3 mice) (as outlined in Table 4 below).

TABLE 4

Experimental group composition. h-pAg: 'helper' peptide; vacc-pAg: vaccination peptide. The number of boost injections is indicated into brackets.

| Group | Peptide (vacc-pAg) | Helper (h-Ag) | Mice | Prime | Boost | Animal Number |
|---|---|---|---|---|---|---|
| 1 | CD22-B1 (60 nMole) | UCP2 (105 nMole) | HHD-DR1 | + | +(1X) | 6 |
| 2 | CD19-B1 (60 nMole) | UCP2 (105 nMole) | HHD-DR1 | + | +(1X) | 6 |
| 3 | CD19-B2 (60 nMole) | UCP2 (105 nMole) | HHD-DR1 | + | +(1X) | 6 |

TABLE 4-continued

Experimental group composition. h-pAg: 'helper' peptide; vacc-pAg: vaccination peptide. The number of boost injections is indicated into brackets.

| Group | Peptide (vacc-pAg) | Helper (h-Ag) | Mice | Prime | Boost | Animal Number |
|---|---|---|---|---|---|---|
| 4 | CD37-B1 (60 nMole) | UCP2 (105 nMole) | HHD-DR1 | + | +(1X) | 5 |
| 5 | TNFRSF13C-B1 (60 nMole) | UCP2 (105 nMole) | HHD-DR1 | + | +(1X) | 5 |
| 6 | CD22-B1 (95 nMole) | DR3 (65 nM) | HHD-DR3 | + | +(1X) | 5 |
| 7 | TNFRSF13C-B1 (95 nMole) | DR3 (65 nM) | HHD-DR3 | + | +(1X) | 5 |
| 8 | CD37-B1 (95 nMole) | DR3 (65 nM) | HHD-DR3 | + | +(1X) | 5 |
| 9 | MS4A1-B4 (60 nMole) | UCP2 (105 nMole) | HHD-DR1 | + | +(1X) | 6 |
| 10 | MS4A1-B4 95 nMole | DR3 (65 nM) | HHD-DR3 | + | +(1X) | 5 |

The peptides were provided as follows:
vacc-pAg: CD22-B1, CD19-B1, CD19-B2, CD37-B1, TNFRSF13C-B1 and MS4A1-B4 all produced and provided at a 4 mg/ml (4 mM) concentration;
h-pAg: DR3 or UCP2 re-suspended in pure distilled water at a 10 mg/mL concentration The peptide formulation to be injected (emulsion) was prepared freshly on each day of injection and for each group. A mix for 10 animals was prepared using 2 mL luer lock syringes (460670 IV, B BRAUN) and luer connectors (Cole-Parmer, 45502-22): 500 µL of peptide mixture in syringe 1 was emulsified with 500 µL of IFA contained in syringe 2, at high speed as fast as possible until forming a thick (white foam) emulsion. Each emulsion was prepared in excess to compensate for the dead volumes at injection.

The animals were immunized on day 0 (d0) with a prime injection, and on d14 with a boost injection. Each mouse was injected s.c. at tail base with 100 µL of an oil-based emulsion that contained:
- 60nMole of vacc-pAg; 105nMole of UCP2 helper peptide (for HHD-DR1 mice) or 65nMole of DR3 helper peptide (for HHD-DR3 mice)
- 10 µL of PBS to reach a total volume of 50 µL (per mouse);
- Incomplete Freund's Adjuvant (IFA) added at 1:1 (v:v) ratio (50 µL per mouse).

A.2 Analysis

Seven days after the boost injection (i.e. on d21), the animals were euthanized and the spleen was harvested. Splenocytes were prepared by mechanical disruption of the organ followed by 70 µm-filtering and Ficoll density gradient purification.

The cell suspensions were further used in an ELISPOT-IFNγ assay (Table 5). The cells were cultured in 200 µL of complete T cell medium. Experimental conditions (duplicates) were as follow: $2 \times 10^5$ total cells per well when cultured in presence of various pAg (10 µM) or medium-only; and $2 \times 10^4$ total cells when cultured in presence of CD3/CD28-loaded bead particles (T cell Activation/Expansion kit, 130-093-627, Miltenyi) (bead-to-cell ratio of 1:1). The cultures were assessed for their capacity to secrete IFNγ (Diaclone Kit Murine IFNγ ELISpot, 862.031-005PC), following the manufacturer's instructions (~16-18 h incubation time before performing the assay). The peptides used for restimulation are described in Table 5.

TABLE 5

Setup of the ELISPOT-IFNγ assay.

| Group | Stimulus | Wells | Animal | Total |
|---|---|---|---|---|
| 1 | CD22-H1 (10 µM) | 3 | 6 | 18 |
|   | CD22-B1 (10 µM) | 3 | 6 | 18 |
|   | CD3/CD28 bead | 3 | 6 | 18 |
|   | Medium | 3 | 6 | 18 |
| 2 | CD19-H1 (10 µM) | 3 | 6 | 18 |
|   | CD19-B1 (10 µM) | 3 | 6 | 18 |
|   | CD3/CD28 bead | 3 | 6 | 18 |
|   | Medium | 3 | 6 | 18 |
| 3 | CD19-H2 (10 µM) | 3 | 6 | 18 |
|   | CD19-B2 (10 µM) | 3 | 6 | 18 |
|   | CD3/CD28 bead | 3 | 6 | 18 |
|   | Medium | 3 | 6 | 18 |
| 4 | CD37-H1 (10 µM) | 3 | 6 | 18 |
|   | CD37-B1 (10 µM) | 3 | 6 | 18 |
|   | CD3/CD28 bead | 3 | 6 | 18 |
|   | Medium | 3 | 6 | 18 |
| 5 | TNFRSF13C-H1 (10 µM) | 3 | 6 | 18 |
|   | TNFRSF13C-B1 (10 µM) | 3 | 6 | 18 |
|   | CD3/CD28 bead | 3 | 6 | 18 |
|   | Medium | 3 | 6 | 18 |
| 6 | CD22-H1 (10 µM) | 3 | 6 | 18 |
|   | CD22-B1 (10 µM) | 3 | 6 | 18 |
|   | CD3/CD28 bead | 3 | 6 | 18 |
|   | Medium | 3 | 6 | 18 |
| 7 | TNFRSF13C-H1 (10 µM) | 3 | 6 | 18 |
|   | TNFRSF13C-B1 (10 µM) | 3 | 6 | 18 |
|   | CD3/CD28 bead | 3 | 6 | 18 |
|   | Medium | 3 | 6 | 18 |
| 8 | CD37-H1 (10 µM) | 3 | 6 | 18 |
|   | CD37-B1 (10 µM) | 3 | 6 | 18 |
|   | CD3/CD28 bead | 3 | 6 | 18 |
|   | Medium | 3 | 6 | 18 |
| 9 | MS4A1-B4 (10 µM) | 3 | 6 | 18 |
|   | MS4A1-H4 (10 µM) | 3 | 6 | 18 |
|   | CD3/CD28 bead | 3 | 6 | 18 |
|   | Medium | 3 | 6 | 18 |

Spots were counted on a CTL ELISpot reader. Data plotting and statistical analysis were performed with the Prism-5 software (GraphPad Software Inc.).

B. Results

All mice were aged of 8 to 13 weeks at the experiment starting date. Both males and females were used in the study. Animals have been housed in groups of 6 per cage at maximum. At time of sacrifice, the spleen T cell population was analysed by flow cytometry, showing that the large majority belonged to the CD4+ T cell subset.

After plating and incubation with the appropriate stimuli, the IFNγ-producing cells were revealed and counted. The data were provided as a number of spots per $1\cdot10^6$ total T cells. The individual average values (obtained from the triplicates) were next used to plot the group average values. Statistical analysis for comparison (to the medium condition) were performed using unpaired non-parametric test (Mann Whitney) (**: $p<0.01$; *: $p<0.05$).

Figure 12:
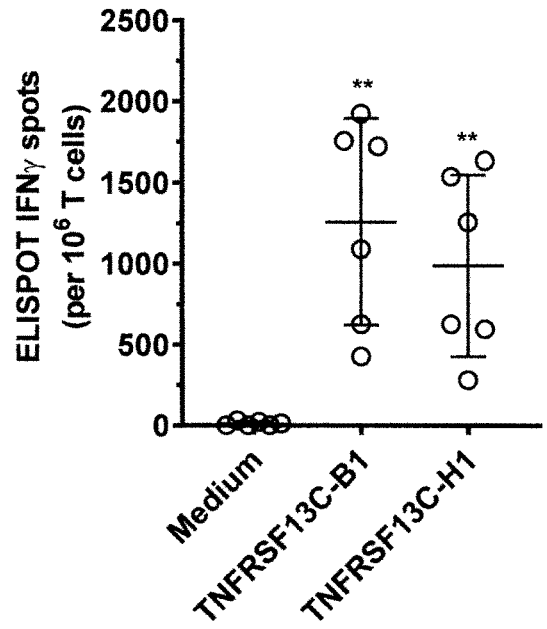
FIG. 12: shows for Example 2 ELISPOT results for HHD DRs HLA-A2 transgenic mice vaccinated with the antigenic peptide TNFRSF13C-B1 as indicated in the figure and cross-reactivity with the human corresponding peptide TNFRSF13C-H1. The data were provided as a number of spots per $1 \cdot 10^6$ total T cells.
Figure 13:
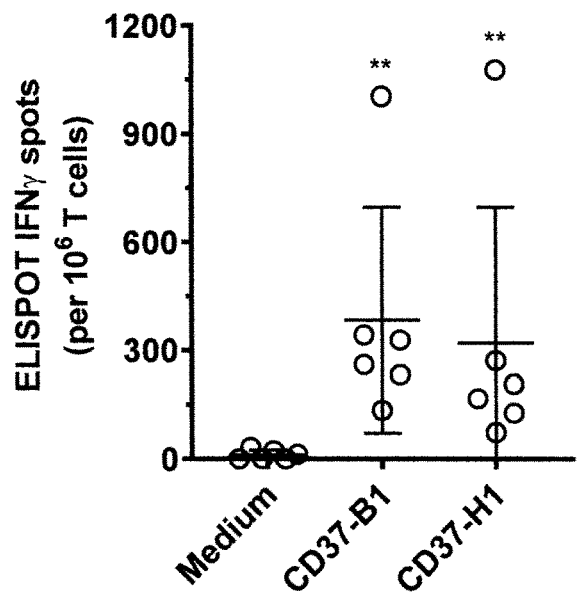
FIG. 13: shows for Example 2 ELISPOT results for HHD DRs HLA-A2 transgenic mice vaccinated with the antigenic peptide CD37-B1 as indicated in the figure and cross-reactivity with the human corresponding peptide CD37-H1. The data were provided as a number of spots per $1 \cdot 10^6$ total T cells.

Overall, vaccination with the antigenic peptides according to the present invention (CD19-B1, CD19-B2, CD22-B1, CD37-B1, TNFRSF13C-B1 and MS4A1-B4) induced significant T cell responses in the ELISPOT-IFNγ assay in HHD DR1 mice (FIGS. 6-10). Immunogenicity of CD22-B1, CD37-B1, TNFRSF13C-B1 and MS4A1-B4 were confirmed in HHD DR1 mice (FIGS. 11-13).

The results (FIG. 6) show that immunization of HHD-DR1 mice with CD22-B1 allows to induce T-cells that are able to react strongly after challenge with either CD22-B1 or the human corresponding peptide CD22-H1. Thus, CD22-B2 is strongly immunogenic and is able to drive an effective immune response against the corresponding human peptide.

Figure 11:
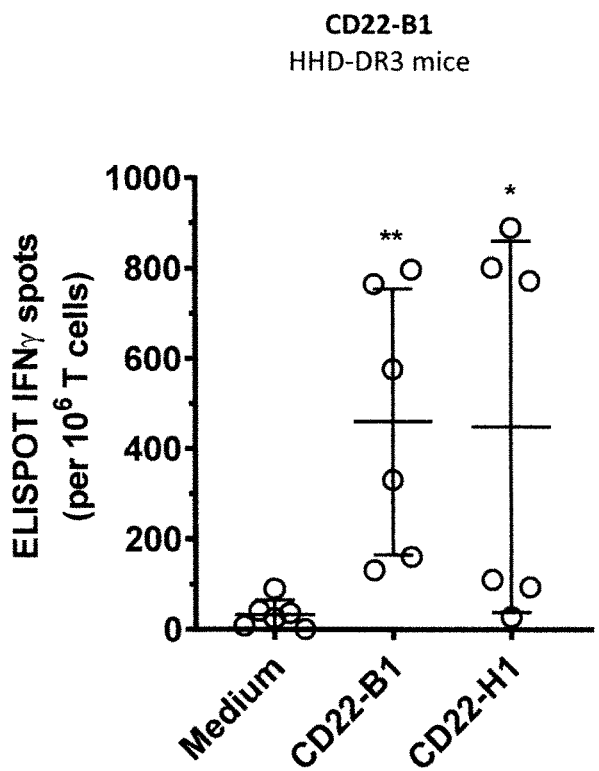
FIG. 11: shows for Example 2 ELISPOT results for HHD DRs HLA-A2 transgenic mice vaccinated with the antigenic peptide CD22-B1 as indicated in the figure and cross-reactivity with the human corresponding peptide CD22-H1. The data were provided as a number of spots per $1 \cdot 10^6$ total T cells.

These results were confirmed in HHD DR3 mice expressing human HLA-A2 and HLA-DRs MHC and lacking the murine H-2 class I and class II MHCs (FIG. 11).

The results (FIG. 7) show that immunization of HHD-DR1 mice with TNFRSF13C-B1 allows to induce T-cells that are able to react strongly after challenge with either TNFRSF13C-B1 or the human corresponding peptide TNFRSF13-H1. Thus, TNFRSF13C-B1 is strongly immunogenic and is able to drive an effective immune response against the corresponding human peptide.

These results were confirmed in HHD DR3 mice expressing human HLA-A2 and HLA-DRs MHC and lacking the murine H-2 class I and class II MHCs (FIG. 12).

The results (FIG. 8) show that immunization of HHD-DR1 mice with CD37-B1 allows to induce T-cells that are able to react strongly after challenge with either CD37-B1 or the human corresponding peptide CD37-H1. Thus, CD37-B2 is strongly immunogenic and is able to drive an effective immune response against the corresponding human peptide.

These results were confirmed in HHD DR3 mice expressing human HLA-A2 and HLA-DRs MHC and lacking the murine H-2 class I and class II MHCs (FIG. 13).

The results (FIG. 9) show that immunization of HHD-DR1 mice with CD19-B2 allows to induce T-cells that are able to react strongly after challenge with either CD19-B2 or the human corresponding peptide CD19-H2. Thus, CD19-B2 is strongly immunogenic and is able to drive an effective immune response against the corresponding human peptide.

The results (FIG. 10) show that immunization of HHD-DR1 mice with CD19-B1 allows to induce T-cells that are able to react strongly after challenge with either CD19-B1 or the human corresponding peptide CD19-H1. Thus, CD19-B1 is strongly immunogenic and is able to drive an effective immune response against the corresponding human peptide.

Figure 15:
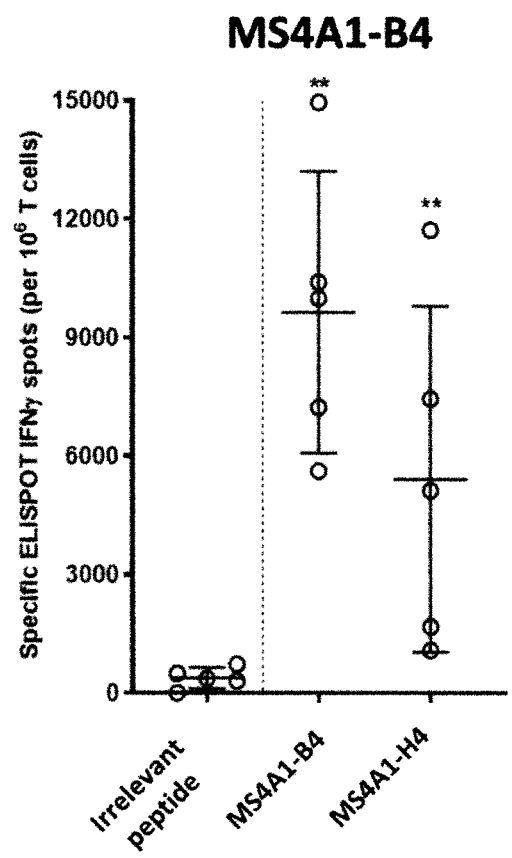
FIG. 15: shows for Example 2 ELISPOT results for HHD DR1 HLA-A2 transgenic mice vaccinated with the antigenic peptide MS4A1-B4 as indicated in the figure and cross-reactivity with the human corresponding peptide MS4A1-H4. The data were provided as a number of spots per $1 \cdot 10^6$ total T cells.

The results (FIG. 15) show that immunization of HHD-DR1 mice with MS4A1-B4 allows to induce T-cells that are able to react strongly after challenge with either MS4A1-B4 or the human corresponding peptide MS4A1-H4. Thus, MS4A1-B4 is strongly immunogenic and is able to drive an effective immune response against the corresponding human peptide.

Figure 16:
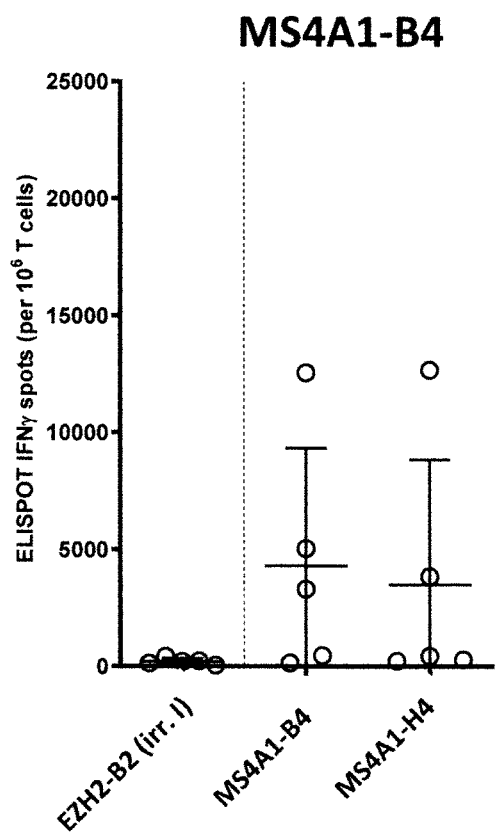
FIG. 16: shows for Example 2 ELISPOT results for HHD DRs HLA-A2 transgenic mice vaccinated with the antigenic peptide MS4A1-B4 as indicated in the figure and cross-reactivity with the human corresponding peptide MS4A1-H4. The data were provided as a number of spots per $1 \cdot 10^6$ total T cells.

These results were confirmed in HHD DR3 mice expressing human HLA-A2 and HLA-DRs MHC and lacking the murine H-2 class I and class II MHCs (FIG. 16).

Altogether, these immunogenicity studies described in Examples 2 performed in HHD DRs and HHD DR1 mice showed that the 6 antigenic peptides of the invention, CD19-B1, CD19-B2, CD22-B1, CD37-B1, TNFRSF13C-B1 and MS4A1-B4 induced strong immune responses. Cross-reactivity of the T cells generated against CD19-B1, CD19-B2, CD22-B1, CD37-B1, TNFRSF13C-B1 and MS4A1-B4 for the corresponding human peptides was shown in HHD DR3 and HHD DR1 mice.

Accordingly, those results provide experimental evidence that antigen-based immunotherapy is able to improve T cell response in vivo and that the antigenic peptides according to the present invention are particularly efficient for that purpose.

Example 3: Ex Vivo Cytotoxic Effects of CD22-B1, CD37B1, TNFRSF13C-B1 and MS4A1-B4 Specific CD8 Human T Cells Multiple investigations support the notion of presence of a repertoire of specific T cells against microbial peptides. The number of microbial specific T-cells against peptides is expected to be low, but sufficient to be re-activated by a vaccine challenge.

To identify and functionally characterize circulating CD22-B1, CD37B1, TNFRSF13C-B1 and MS4A1-B4 specific T cells in humans, an in vitro amplification protocol has been developed in order to detect T cells specific for each antigenic peptide and investigate their cytotoxic capacity.

3.1 Identification of Antigenic Peptide-Specific CD8 T Cells in Human

In vitro amplification method and specific pMHC multimers have been used for identification of CD22-B1, CD37-B1, TNFRSF13C-B1 and MS4A1-B4 specific T cells. pMHC multimers were generated for all the bacteria peptides and their respective human counterpart. PBMCs from several HLA-A*02 healthy donors (up to 19 donors) were collected, enriched after CD137 and CD8 selection and subjected to multiple rounds of in vitro amplification with EO2463 peptides loaded T2 cells to increase the number of specific T cell clones. Detection of OMP peptide specific CD8 T cells using cytometry analysis with the fluorescent multimer was performed on enriched CD8 T cell populations FIG. 17 exemplifies results obtained with one HLA-A2 healthy donor. For this donor, cell amplification allows detection of MS4A1-B4 specific cells (19.7%), TNFRSF13C-B1 specific cells (13%), CD22-B1 specific cells (4.6%) and CD37-B1 specific cells (2.5%).

In conclusion, these results demonstrate the presence of CD8 T cells in the blood of healthy HLA-A2 donors that can recognize the microbiome-derived peptides, and importantly also the human counterpart peptides.

3.2 Antigenic Peptide-Specific CD8 T Cytotoxicity Functions

Figure 17:
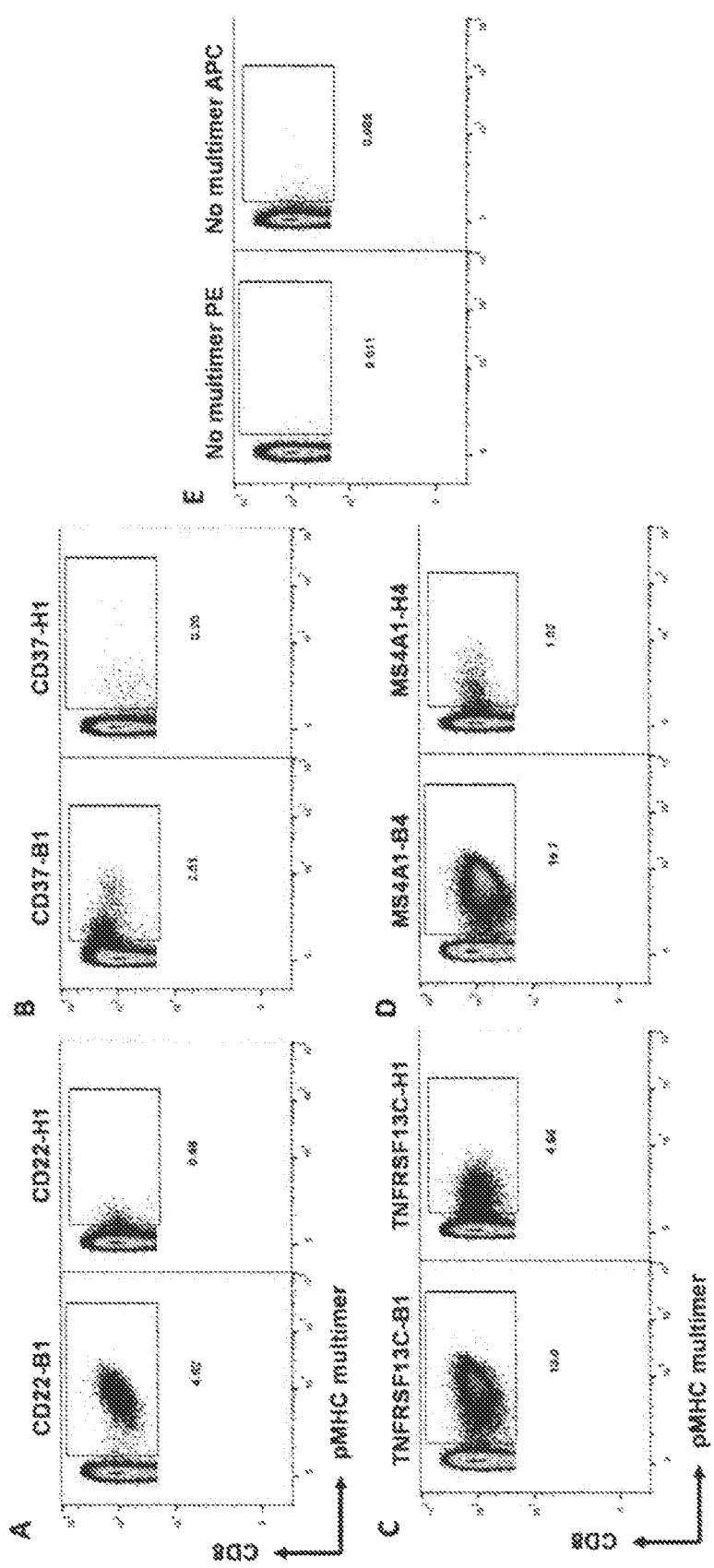
FIG. 17: shows for Example 3 the detection of CD22-B1, CD37B1, TNFRSF13C-B1 and MS4A1-B4 peptide-specific CD8+ T cells detected in peripheral blood from healthy donors (HLA-A2 positive).
Figure 18:
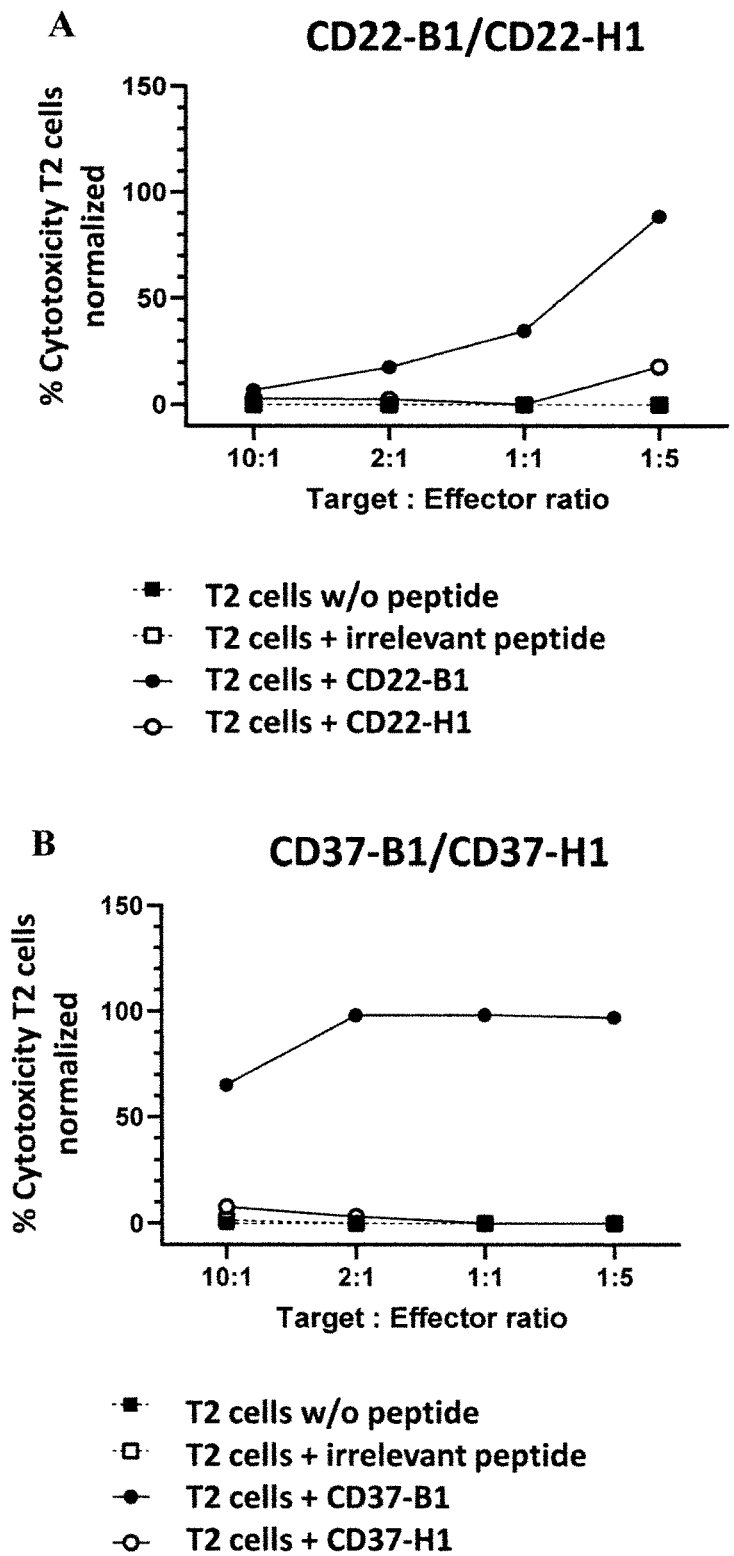
FIG. 18: shows for Example 3 the cytotoxic capacity of the CD22-B1, CD37B1, TNFRSF13C-B1 and MS4A1-B4 peptide-specific human T cells clone expanded in vitro by microbiome derived peptide stimulation. CD22-B1, CD37B1, TNFRSF13C-B1 and MS4A1-B4 peptide-specific T cells have the ability to kill T2 cells loaded with bacterial or human peptides.
Figure 18:
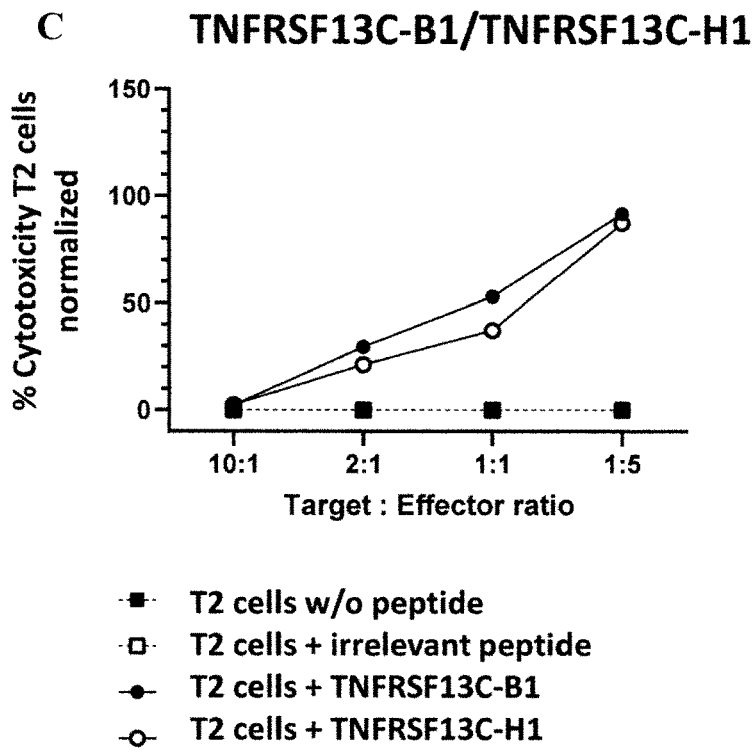
Figure 18:
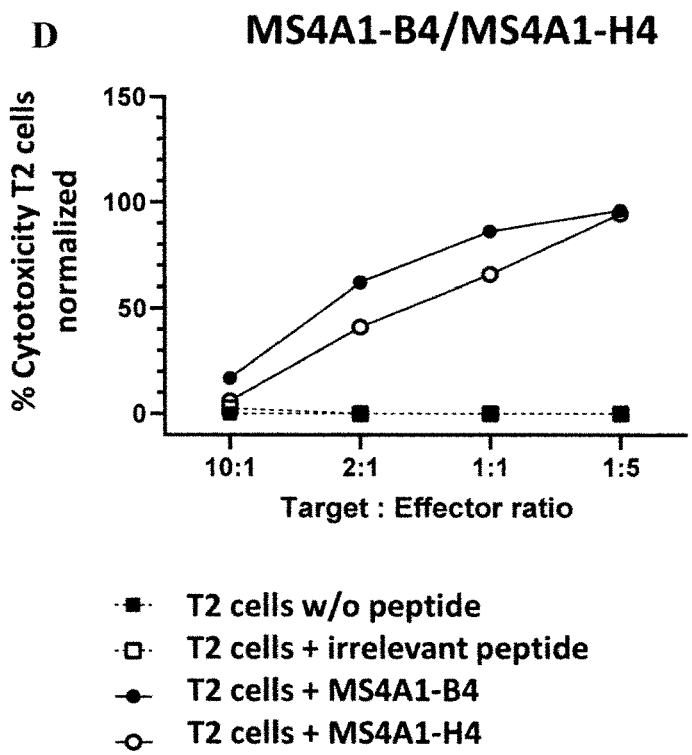
Figure 19:
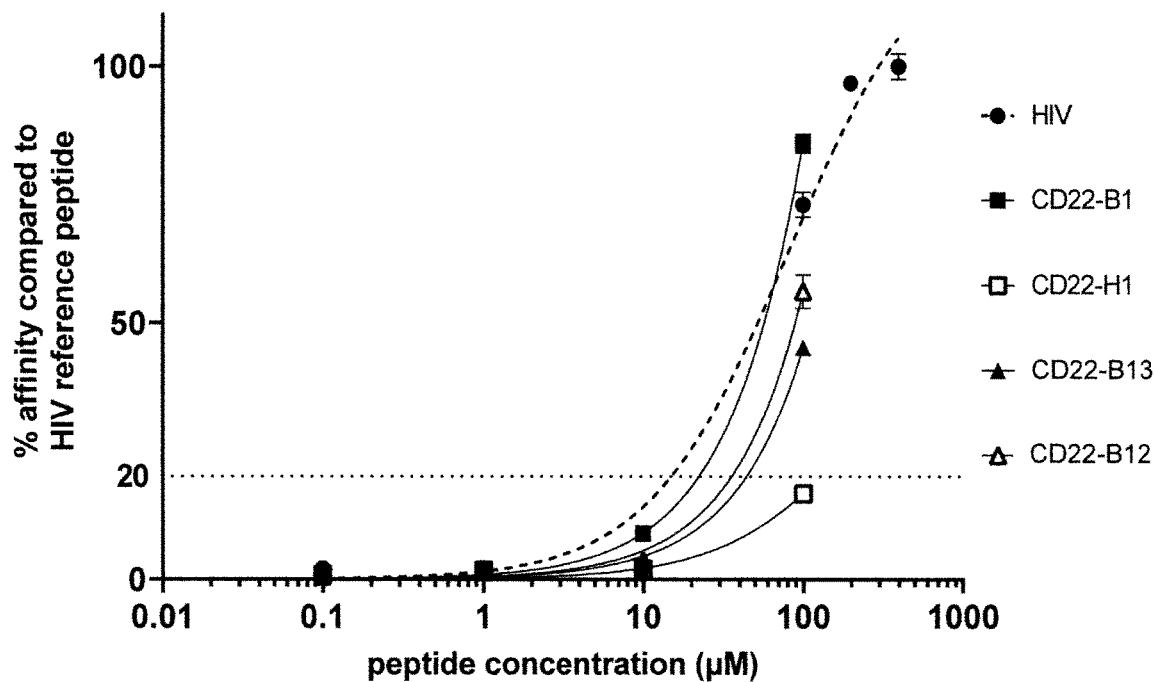
FIG. 19: shows for Example 4 in vitro affinity for the antigenic peptides CD22-B1, CD22-B12 and CD22-B13 in comparison to the corresponding human CD22 epitope CD22-H1.
Figure 20:
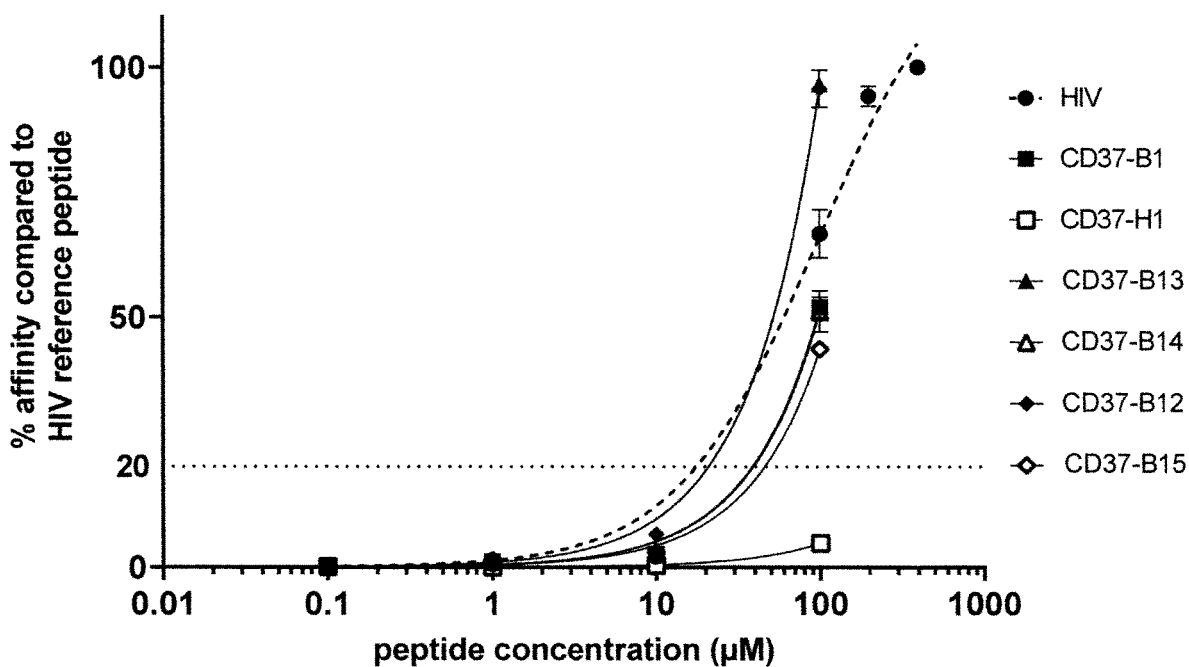
FIG. 20: shows for Example 4 in vitro affinity for the antigenic peptides CD37-B1, CD37-B12, CD37-B11, CD37-B14 and CD37-B15 in comparison to the corresponding human CD37 epitope CD37-H1.
Figure 21:
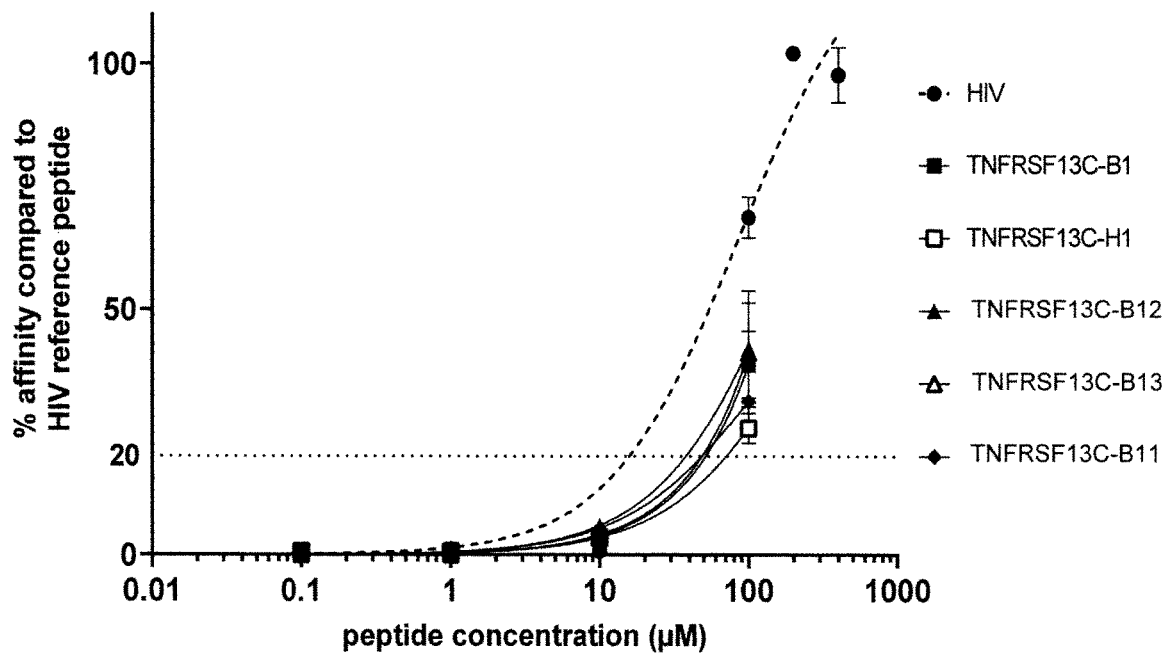
FIG. 21 shows for Example 4 in vitro affinity for the antigenic peptides TNFRSF13C-B1, TNFRSF13C-B11, TNFRSF13C-B12 and TNFRSF13C-B13 in comparison to the corresponding human TNFRSF13C epitope TNFRSF13C-H1.
Figure 22:
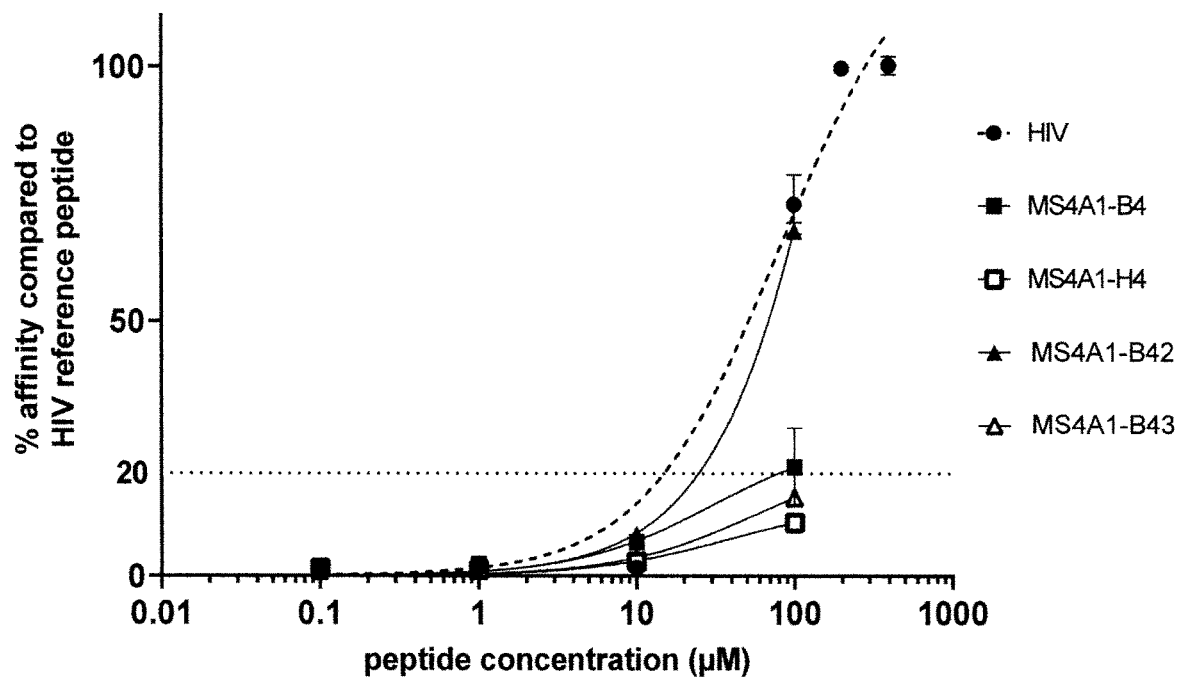
FIG. 22: shows for Example 4 in vitro affinity for the antigenic peptide MS4A1-B4, MS4A1-B42 and MS4A1-B43 in comparison to the corresponding human MS4A1 epitope MS4A1-H4.

CD8+ T cells expanded per above were used to perform cytotoxic assays in presence of different ratios of target and effector cells to assess their cytotoxic capacity, using flow cytometry readout. Target cells were T2 cell lines loaded with bacterial peptide or human counterpart peptide. Negative control was T2 cells unloaded and T2 cells loaded with irrelevant peptide. As shown in FIG. 18, antigenic peptide-specific human T cells clone expanded in vitro have the capacity to kill T2 cells loaded with all the bacteria peptide, CD22-B1, CD37B1, TNFRSF13C-B1 and MS4A1-B4. More importantly, CD22-B1, CD37B1, TNFRSF13C-B1 and MS4A1-B4-specific human T cells clones expanded in vitro were able to kill T2 cells loaded with the human TNFR13C (BAFF-R) or MS4A1 (CD20) peptide when cross-reactivity is observed with the staining (FIG. 17).

Overall, these results demonstrate the presence of T cell clones in healthy volunteers able to recognize microbial peptide and to kill target with microbial peptides and human counterparts. These data are particularly encouraging as T cell clones have been obtained in healthy donors, therefore we could expect that specific T cell clones could be efficiently amplified in patients exposed to the immunization by antigenic peptides of the invention.

Example 4: Further Antigenic Peptides have Superior Affinity to the HLA-A*0201 Allele Next, binding affinity of further selected antigenic peptides and of the corresponding fragments of human tumor antigens (human reference peptides) to the HLA-A*0201 allele was confirmed in vitro.

Namely, the antigenic peptides of sequence SEQ ID NO: 110 («YIFEHPELL» also referred to herein as CD22-B1), of sequence SEQ ID NO: 107 («LIFEHPERV» also referred to herein as CD22-B12), and of sequence SEQ ID NO: 108 («RVFEHPELV» also referred to herein as CD22-B13) were compared to the corresponding reference human peptide derived from CD22 («WVFEHPETL», SEQ ID NO: 270, also referred herein as CD22-H1).

Moreover, the antigenic peptides of sequence SEQ ID NO: 114 («FLAFVPLQL» also referred herein as CD37-B1), of sequence SEQ ID NO: 119 («ILAFVPLYL» also referred to herein as CD37-B12), of sequence SEQ ID NO: 120 («IMAFVPLAV» also referred to herein as CD37-B13), of sequence SEQ ID NO: 491 («FLAFVPLDV» also referred to herein as CD37-B14) and of sequence SEQ ID NO: 493 («VLAFVPLGV» also referred to herein as CD37-B15) were compared to the corresponding reference human peptide derived from CD37 («GLAFVPLQI», SEQ ID NO: 271, also referred herein as CD37-H1).

Furthermore, the antigenic peptides of sequence SEQ ID NO: 220 («LMFGAPALV» also referred herein as TNFRSF13C-B1), of sequence SEQ ID NO: 212 («FLFGAPASA» also referred to herein as TNFRSF13C-B11), of sequence SEQ ID NO: 217 («LLFGAPAGV» also referred to herein as TNFRSF13C-B12), and of sequence SEQ ID NO: 224 («VLFGAPAYL» also referred to herein as TNFRSF13C-B13) were compared to the corresponding reference human peptide derived from TNFRSF13C («LLFGAPALL», SEQ ID NO: 279, also referred herein as TNFRSF13C-H1).

In addition, the antigenic peptides of sequence SEQ ID NO: 65 («AMNSLSLYI» also referred herein as MS4A1-B4), of sequence SEQ ID NO: 70 («YMNSLSLAL» also referred to herein as MS4A1-B42) and of sequence SEQ ID NO: 477 («AMNSLSLTV» also referred to herein as MS4A1-B43) were compared to the corresponding reference human peptide derived from MS4A1 (also known as CD20) («IMNSLSLFA», SEQ ID NO: 264, also referred herein as MS4A1-H4).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30(12):3411-21). Affinity measurement of the peptides is achieved with the human tumoral cell T2 which expresses the HLA-A*0201 molecule, but which is TAP ½ negative and incapable of presenting endogenous peptides.

T2 cells (5.104 cells per well) are incubated with decreasing concentrations of peptides from 100 µM to 0.1 µM (4 points: 100 µM, 10 µM, 1 µM, 0.1 µM) in serum-free medium (TexMacs) supplemented with 100 ng/µl of 32 Microglobulin at 37° C. for 16 hours. Cells are then washed two times and marked with the anti-HLA-A2 antibody coupled to PE (clone BB7.2, BD Pharmagen).

The analysis is achieved by FACS (Macsquant analyzer 10-Miltenyi).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 µM.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

Results are shown in FIGS. 19-22. For each of the tested human reference epitopes CD22-H1 (FIG. 19), CD37-H1 (FIG. 20), TNFRSF13C-H1 (FIG. 21) and MS4A1-H4 (FIG. 22), the respective antigenic peptides according to the present invention show a stronger binding affinity to HLA-A*0201.

In summary, the results show that the antigenic peptides according to the present invention show stronger binding affinity to HLA-A*0201 than the corresponding human tumor antigen fragments. As outlined above, without being bound to any theory it is assumed that such a strong binding affinity of the antigenic peptides according to the present invention reflects their ability to raise an immune response (i.e., their immunogenicity).

The invention claimed is:

1. An antigenic peptide consisting of an amino acid sequence as set forth in any one of SEQ ID NO: 65, 70, 114, 119, 120, 477, 491, and 493.

2. The antigenic peptide according to claim 1, wherein the antigenic peptide consists of an amino acid sequence as set forth in SEQ ID NO: 114.

3. The antigenic peptide according to claim 1, wherein the antigenic peptide comprises or consists of an amino acid sequence as set forth in SEQ ID NO: 65.

4. An immunogenic compound comprising the antigenic peptide according to claim 1.

5. A cell loaded with the antigenic peptide according to claim 1 or with an immunogenic compound comprising the antigenic peptide.

6. A nucleic acid encoding an antigenic peptide consisting of an amino acid sequence as set forth in any one of SEQ ID NO: 65, 70, 114, 119, 120, 477, 491, and 493; or a polypeptide comprising the antigenic peptide.

7. A host cell comprising the nucleic acid according to claim 6, wherein the nucleic acid is a vector.

8. A pharmaceutical composition comprising
   an antigenic peptide consisting of an amino acid sequence as set forth in any one of SEQ ID NO: 65, 70, 114, 119, 120, 477, 491, and 493;
   and, optionally, one or more pharmaceutically acceptable excipients or carriers.

9. The pharmaceutical composition according to claim 8, wherein the composition comprises a first and a second antigenic peptide.

10. The pharmaceutical composition according to claim 9 further comprising a third and optionally a fourth antigenic peptide.

11. The pharmaceutical composition according to claim 10, wherein
the first antigenic peptide consists of an amino acid sequence as set forth in SEQ ID NO: 110;
the second antigenic peptide consists of an amino acid sequence as set forth in SEQ ID NO: 114;
the third antigenic peptide consists of an amino acid sequence as set forth in SEQ ID NO: 220; and
optionally, the fourth antigenic peptide consists of an amino acid sequence as set forth in SEQ ID NO: 65.

12. The pharmaceutical composition according to claim 8 further comprising a helper peptide.

13. A kit comprising
the antigenic peptide according to claim 1, or
a pharmaceutical composition comprising the antigenic peptide.

14. The kit according to claim 13, wherein the kit comprises at least two distinct antigenic peptides.

15. A combination of at least two distinct antigenic peptides according to claim 1.

16. A peptide-MHC (pMHC) multimer comprising the antigenic peptide according to claim 1.

17. The pharmaceutical composition according to claim 11, further comprising a peptide consisting of an amino acid sequence according to SEQ ID NO: 475.

18. The pharmaceutical composition according to claim 10, wherein the first antigenic peptide consists of an amino acid sequence as set forth in SEQ ID NO: 65 and the second antigenic peptide consists of an amino acid sequence as set forth in SEQ ID NO: 114.

19. The pharmaceutical composition according to claim 11, wherein the first antigenic peptide consists of an amino acid sequence as set forth in SEQ ID NO:
the second antigenic peptide consists of an amino acid sequence as set forth in SEQ ID 110;
the second antigenic peptide consists of an amino acid sequence as set forth in SEQ ID NO: 114;
the third antigenic peptide consists of an amino acid sequence as set forth in SEQ ID NO: 220; and
the fourth antigenic peptide consists of an amino acid sequence as set forth in SEQ ID NO: 65.

20. The pharmaceutical composition according to claim 19, wherein
the first antigenic peptide consists of an amino acid sequence as set forth in SEQ ID NO: 110;
the second antigenic peptide consists of an amino acid sequence as set forth in SEQ ID NO: 114;
the third antigenic peptide consists of an amino acid sequence as set forth in SEQ ID NO: 220; and
the fourth antigenic peptide consists of an amino acid sequence as set forth in SEQ ID NO: 65, and
a further peptide consisting of an amino acid sequence as set forth in SEQ ID NO: 475.

* * * * *

UNITED STATES PATENT AND TRADEMARK OFFICE
CERTIFICATE OF CORRECTION

PATENT NO. : 11,759,508 B2
APPLICATION NO. : 17/734694
DATED : September 19, 2023
INVENTOR(S) : Laurent Chene et al.

It is certified that error appears in the above-identified patent and that said Letters Patent is hereby corrected as shown below:

In the Claims

Column 229, Claim 3, Line 59, delete "comprises or"

Column 302, Claim 19, Line 5, delete the text beginning with "wherein the first" to and ending "in SEQ ID NO:" in Column 302, Claim 19, Line 6

Column 302, Claim 19, Line 7, replace "second" with --first--

Signed and Sealed this
Thirteenth Day of February, 2024

Katherine Kelly Vidal
*Director of the United States Patent and Trademark Office*